(12) United States Patent
Claremon et al.

(10) Patent No.: US 8,242,111 B2
(45) Date of Patent: Aug. 14, 2012

(54) CYCLIC INHIBITORS OF 11β-HYDROXYSTEROID DEHYDROGENASE 1

(75) Inventors: David A. Claremon, Maple Glen, PA (US); Linghang Zhuang, Chalfont, PA (US); Katerina Leftheris, Skillman, NJ (US); Colin M. Tice, Ambler, PA (US); Yuanjie Ye, Ambler, PA (US); Suresh B. Singh, Kendall Park, NJ (US)

(73) Assignee: Vitae Pharmaceuticals, Inc., Fort Washington, PA (US)

( * ) Notice: Subject to any disclaimer, the term of this patent is extended or adjusted under 35 U.S.C. 154(b) by 0 days.

(21) Appl. No.: 12/990,309

(22) PCT Filed: Apr. 30, 2009

(86) PCT No.: PCT/US2009/002629
§ 371 (c)(1),
(2), (4) Date: Feb. 10, 2011

(87) PCT Pub. No.: WO2009/134384
PCT Pub. Date: Nov. 5, 2009

(65) Prior Publication Data
US 2011/0124635 A1 May 26, 2011

Related U.S. Application Data

(60) Provisional application No. 61/206,825, filed on Feb. 4, 2009, provisional application No. 61/137,148, filed on Jul. 25, 2008, provisional application No. 61/049,650, filed on May 1, 2008.

(30) Foreign Application Priority Data

Jul. 25, 2008 (WO) ................ PCT/US2008/009017

(51) Int. Cl.
*C07D 417/14* (2006.01)
*C07D 413/14* (2006.01)
*A61K 31/5355* (2006.01)

(52) U.S. Cl. ...................... 514/228.8; 544/96
(58) Field of Classification Search ................ 544/96; 514/228.8
See application file for complete search history.

(56) References Cited

U.S. PATENT DOCUMENTS

| | | |
|---|---|---|
| 3,341,538 A | 9/1967 | Block et al. |
| 3,681,349 A | 8/1972 | Schwan et al. |
| 4,136,145 A | 1/1979 | Fuchs et al. |
| 4,136,162 A | 1/1979 | Fuchs et al. |
| 5,089,506 A | 2/1992 | Gray et al. |
| 5,098,916 A | 3/1992 | Gray et al. |
| 5,215,992 A | 6/1993 | Gray et al. |
| 5,393,735 A | 2/1995 | Lange et al. |
| 5,410,081 A | 4/1995 | Kunde et al. |
| 5,432,175 A | 7/1995 | Piwinski et al. |
| 5,480,899 A | 1/1996 | Yano et al. |
| 5,502,027 A | 3/1996 | Lange et al. |
| 5,631,209 A | 5/1997 | Lange et al. |
| 5,776,959 A | 7/1998 | Covey et al. |

(Continued)

FOREIGN PATENT DOCUMENTS

DE    1801556 A1    5/1970

(Continued)

OTHER PUBLICATIONS

Chalmers (TiPS vol. 17, pp. 166-172 Apr. 1996).*

(Continued)

*Primary Examiner* — Kahsay T Habte
(74) *Attorney, Agent, or Firm* — McCarter & English, LLP; Steven G. Davis; Michael DeGrazia

(57) ABSTRACT

This invention relates to novel compounds of a structural formula selected from:

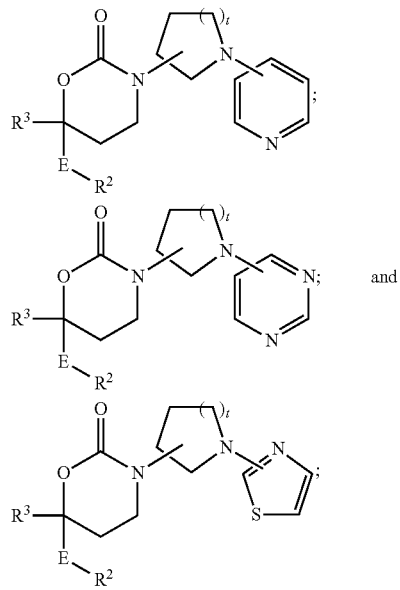

pharmaceutically acceptable salts thereof, and pharmaceutical compositions thereof, which are useful for the therapeutic treatment of diseases associated with the modulation or inhibition of 11β-HSD1 in mammals, e.g., diabetes mellitus and obesity. Values for the variables in the structural formulas are provided herein. The invention further relates to pharmaceutical compositions of the novel compounds and methods for their use in the reduction or control of the production of cortisol in a cell or the inhibition of the conversion of cortisone to cortisol in a cell.

24 Claims, No Drawings

U.S. PATENT DOCUMENTS

| | | |
|---|---|---|
| 5,780,466 A | 7/1998 | Emonds-Alt et al. |
| 5,811,422 A | 9/1998 | Lam et al. |
| 5,856,273 A | 1/1999 | Kay et al. |
| 5,866,702 A | 2/1999 | Mackman et al. |
| 5,936,124 A | 8/1999 | Hilborn et al. |
| 5,981,436 A | 11/1999 | Drewes et al. |
| 6,066,666 A | 5/2000 | Covey et al. |
| 6,159,990 A | 12/2000 | Lagu et al. |
| 6,242,637 B1 | 6/2001 | Emonds-Alt et al. |
| 6,251,897 B1 | 6/2001 | Ina et al. |
| 6,559,163 B2 | 5/2003 | Cai et al. |
| 6,620,815 B1 | 9/2003 | Lagu et al. |
| 6,635,630 B2 | 10/2003 | Shih et al. |
| 6,638,935 B2 | 10/2003 | Emig et al. |
| 6,653,315 B2 | 11/2003 | Tulshian et al. |
| 6,706,722 B2 | 3/2004 | Emig et al. |
| 6,794,390 B2 | 9/2004 | Lum et al. |
| 6,841,671 B2 | 1/2005 | Noe et al. |
| 6,890,926 B2 | 5/2005 | Emig et al. |
| 6,900,201 B2 | 5/2005 | Noe et al. |
| 6,916,807 B2 | 7/2005 | Freeman-Cook et al. |
| 6,936,615 B2 | 8/2005 | Emig et al. |
| 7,026,310 B2 | 4/2006 | Emig et al. |
| 7,056,912 B2 | 6/2006 | Emig et al. |
| 7,132,551 B2 | 11/2006 | Aquila et al. |
| 7,186,844 B2 | 3/2007 | Ikemoto |
| 7,208,487 B2 | 4/2007 | Bergnes et al. |
| 7,253,198 B2 | 8/2007 | Demont et al. |
| 7,256,005 B2 | 8/2007 | Zitzmann et al. |
| 7,262,212 B2 | 8/2007 | Tsubouchi et al. |
| 7,294,637 B2 | 11/2007 | Aquila et al. |
| 7,417,045 B2 | 8/2008 | Anilkumar et al. |
| 7,566,718 B2 | 7/2009 | Wong et al. |
| 2001/0039286 A1 | 11/2001 | Dinnell et al. |
| 2006/0063819 A1 | 3/2006 | Lanter et al. |
| 2006/0089349 A1 | 4/2006 | Gundertofte et al. |
| 2006/0116382 A1 | 6/2006 | Yao et al. |
| 2006/0194780 A1 | 8/2006 | Nargund et al. |
| 2006/0276457 A1 | 12/2006 | Yu et al. |
| 2006/0276479 A1 | 12/2006 | Kim et al. |
| 2006/0276480 A1 | 12/2006 | Wong et al. |
| 2007/0021611 A1 | 1/2007 | McGuinness et al. |
| 2007/0054919 A1 | 3/2007 | Rosenblum et al. |
| 2007/0082913 A1 | 4/2007 | Kim et al. |
| 2007/0129345 A1 | 6/2007 | Zhuo et al. |
| 2007/0208001 A1 | 9/2007 | Zhuo et al. |
| 2007/0219182 A1 | 9/2007 | Lubisch et al. |
| 2007/0254875 A1 | 11/2007 | Zhi et al. |
| 2007/0254901 A1 | 11/2007 | Bilodeau et al. |
| 2007/0259891 A1 | 11/2007 | Strobel et al. |
| 2008/0004300 A1 | 1/2008 | Strobel et al. |
| 2008/0021029 A1 | 1/2008 | Strobel et al. |
| 2008/0045518 A1 | 2/2008 | Commons et al. |
| 2008/0045578 A1 | 2/2008 | Commons et al. |
| 2008/0045579 A1 | 2/2008 | Commons et al. |
| 2008/0124384 A1 | 5/2008 | Blum |
| 2008/0188482 A1 | 8/2008 | Rice et al. |
| 2008/0249087 A1 | 10/2008 | Rotstein et al. |
| 2008/0269295 A1 | 10/2008 | Haurand et al. |
| 2008/0280933 A1 | 11/2008 | Efremov et al. |
| 2008/0312271 A1 | 12/2008 | Efremov et al. |
| 2009/0018054 A1 | 1/2009 | Ali et al. |
| 2009/0264650 A1 | 10/2009 | Cho et al. |
| 2010/0041637 A1 | 2/2010 | Claremon et al. |
| 2010/0197675 A1 | 8/2010 | Claremon et al. |
| 2010/0256363 A1 | 10/2010 | Xu |
| 2010/0324045 A1 | 12/2010 | Claremon et al. |
| 2011/0009402 A1 | 1/2011 | Himmelsbach |
| 2011/0015157 A1 | 1/2011 | Claremon et al. |
| 2011/0021512 A1 | 1/2011 | Claremon et al. |
| 2011/0028445 A1 | 2/2011 | Eckhardt et al. |
| 2011/0071139 A1 | 3/2011 | Claremon et al. |
| 2011/0098320 A1 | 4/2011 | Claremon et al. |
| 2011/0105504 A1 | 5/2011 | Claremon et al. |
| 2011/0112082 A1 | 5/2011 | Claremon et al. |
| 2011/0124635 A1 | 5/2011 | Claremon et al. |
| 2011/0190262 A1 | 8/2011 | Himmelsbach et al. |
| 2011/0224242 A1 | 9/2011 | Giethlen et al. |

FOREIGN PATENT DOCUMENTS

| | | |
|---|---|---|
| DE | 19918725 A1 | 10/2000 |
| DE | 19929348 A1 | 12/2000 |
| DE | 100 34 623 | 1/2002 |
| DE | 10034623 | 1/2002 |
| EP | 0415642 A1 | 3/1991 |
| EP | 0454444 A1 | 10/1991 |
| EP | 0640594 A1 | 3/1995 |
| EP | 0645387 A | 3/1995 |
| EP | 0471591 B1 | 5/1995 |
| EP | 0928789 A1 | 7/1999 |
| EP | 1156049 A | 11/2001 |
| EP | 1270724 A2 | 1/2003 |
| EP | 1852425 A | 11/2007 |
| EP | 1864971 A | 12/2007 |
| EP | 1935420 | 6/2008 |
| GB | 1077711 | 8/1967 |
| JP | 6092945 A | 4/1994 |
| JP | 7157681 | 6/1995 |
| JP | 2009110842 A2 | 4/1997 |
| JP | 09151179 | 6/1997 |
| JP | 2002179572 A2 | 6/2002 |
| JP | 2003096058 | 4/2003 |
| JP | 2003300884 A2 | 10/2003 |
| JP | 2005-206503 A | 8/2005 |
| JP | 2005239670 | 9/2005 |
| JP | 2005272321 A | 10/2005 |
| JP | 2007 140188 | 6/2007 |
| JP | 2007 254409 | 10/2007 |
| WO | WO 92/07838 | 5/1992 |
| WO | WO 93/07128 | 4/1993 |
| WO | WO 93/13103 | 7/1993 |
| WO | WO 95/31440 | 11/1995 |
| WO | WO 96/14297 A | 5/1996 |
| WO | WO 96/23787 | 8/1996 |
| WO | WO 97/36605 | 10/1997 |
| WO | WO 98/57940 | 12/1998 |
| WO | WO 99/05125 | 2/1999 |
| WO | WO 99/06395 | 2/1999 |
| WO | WO 01/00595 A1 | 1/2001 |
| WO | WO 01/44200 A2 | 6/2001 |
| WO | WO 01/55063 | 8/2001 |
| WO | WO 02/06244 A1 | 1/2002 |
| WO | WO 02/06277 A1 | 1/2002 |
| WO | WO 02/22572 A2 | 3/2002 |
| WO | WO 03/043988 A1 | 5/2003 |
| WO | WO 03/057673 A | 7/2003 |
| WO | WO 03/093261 A1 | 11/2003 |
| WO | WO 2004/004722 A1 | 1/2004 |
| WO | WO 2004/009559 A2 | 1/2004 |
| WO | WO 2004/014859 A2 | 2/2004 |
| WO | WO 2004/046137 A1 | 6/2004 |
| WO | WO 2004/094375 A | 11/2004 |
| WO | WO 2005/000845 | 1/2005 |
| WO | WO 2005/086700 A2 | 9/2005 |
| WO | WO 2005/108361 | 11/2005 |
| WO | WO 2005/108361 A | 11/2005 |
| WO | WO 2005/113525 A1 | 12/2005 |
| WO | WO 2006/003494 A2 | 1/2006 |
| WO | WO 2006/014357 A | 2/2006 |
| WO | WO 2006/024627 A2 | 3/2006 |
| WO | WO 2006/024628 A | 3/2006 |
| WO | WO 2006/031715 A | 3/2006 |
| WO | WO 2006/040329 | 4/2006 |
| WO | WO 2006/044174 | 4/2006 |
| WO | WO 2006/049952 A | 5/2006 |
| WO | WO 2006/066924 A2 | 6/2006 |
| WO | WO 2006/066948 A1 | 6/2006 |
| WO | WO 2006/090792 A1 | 8/2006 |
| WO | WO 2006/104280 A | 10/2006 |
| WO | WO 2006/109056 A1 | 10/2006 |
| WO | WO 2007/008529 A2 | 1/2007 |
| WO | WO 2007/048595 A1 | 5/2007 |
| WO | WO 2007/051810 | 5/2007 |
| WO | WO 2007/061661 A2 | 5/2007 |
| WO | WO 2007/068330 A1 | 6/2007 |
| WO | WO 2007/079186 A2 | 7/2007 |
| WO | WO 2007/081569 A2 | 7/2007 |
| WO | WO 2007/081570 A | 7/2007 |

| | | |
|---|---|---|
| WO | WO 2007/081571 A2 | 7/2007 |
| WO | WO 2007/084314 A2 | 7/2007 |
| WO | WO 2007/109456 A2 | 9/2007 |
| WO | WO 2007/118185 A2 | 10/2007 |
| WO | WO 2007/124254 | 11/2007 |
| WO | WO 2007/124329 A | 11/2007 |
| WO | WO 2007/124337 | 11/2007 |
| WO | WO 2007/127693 A | 11/2007 |
| WO | WO 2008/000951 | 1/2008 |
| WO | WO 2008/031227 A1 | 3/2008 |
| WO | WO 2008/036715 A1 | 3/2008 |
| WO | WO 2008/046758 A | 4/2008 |
| WO | WO 2008/059948 A | 5/2008 |
| WO | WO 2008/106128 | 9/2008 |
| WO | WO 2008/106128 A | 9/2008 |
| WO | WO 2008/118332 A2 | 10/2008 |
| WO | WO 2009/017664 | 2/2009 |
| WO | WO 2009/017664 A1 | 2/2009 |
| WO | WO 2009/017671 | 2/2009 |
| WO | WO 2009/061498 | 5/2009 |
| WO | WO 2009/063061 | 5/2009 |
| WO | WO 2009/075835 | 6/2009 |
| WO | WO 2009/088997 | 7/2009 |
| WO | WO 2009/094169 A | 7/2009 |
| WO | WO 2009/100872 | 8/2009 |
| WO | WO 2009/102428 | 8/2009 |
| WO | WO 2009/102460 | 8/2009 |
| WO | WO 2009/117109 | 9/2009 |
| WO | WO 2009/134384 | 11/2009 |
| WO | WO 2009/134387 | 11/2009 |
| WO | WO 2009/134392 | 11/2009 |
| WO | WO 2009/134400 | 11/2009 |
| WO | WO 2009/138386 | 11/2009 |
| WO | WO 2010/010149 | 1/2010 |
| WO | WO 2010/010150 A1 | 1/2010 |
| WO | WO 2010/010157 | 1/2010 |
| WO | WO 2010/010174 | 1/2010 |
| WO | WO 2010/011314 | 1/2010 |
| WO | WO 2010/023161 | 3/2010 |
| WO | WO 2010/046445 | 4/2010 |
| WO | WO 2010/091067 | 8/2010 |
| WO | WO 2010/127237 | 11/2010 |

OTHER PUBLICATIONS

Database CA [Online], Chemical Abstracts Service, Fukushima et al., "Preparation of Imidazolidinone Derivatives as 11.beta.-HSD1 Inhibitors", 2007, XP 002531878.
Gavezzotti, "Are Crystal Structures Predictable?", Accounts of Chemical Research, 1994, vol. 27, pp. 309-314.
Vippagunta, et al., "Crystalline Solids", Advanced Drug Deliver Reviews, 2001, vol. 48, pp. 3-26.
International Search Report and Written Opinion—(PCT/US2008/009048) Date of Mailing Dec. 4, 2008.
International Search Report—(PCT/US2009/004261) Date of Mailing Oct. 21, 2009.
Shibata, et al., "Cycloaddition of Oxetanes with Heterocumulenes Catalysed by Organotin Iodine-Lewis Base Complex", Journal of Heterocyclic Chemistry, vol. 24, 1987, pp. 361-363.
Ofice Action for U.S. Appl. No. 12/741,532, date of mailing Dec. 15, 2010.
Ofice Action for U.S. Appl. No. 12/771,449, date of mailing Dec. 21, 2010.
CA 154 : 284276, dated Aug. 10, 2009.
CA 1267843-31-1, dated Aug. 10, 2009.
Sullivan, John M. and Efner, Howard F., "The Preparation of 6-Aryltetrahydro-1,3-oxazin-2-ones and Their Hydrolysis to 3-Substituted Propylamines," The Journal of Organic Chemistry, 33 (5): 2134-2136 (1966).
Wolfling, Janos et al., "Neighboring Group Participation Part 15. Stereoselective Synthesis of Some Steroidal Tetrahydrooxaziin-2-ones, as Novel Presumed Inhibitors of Human 5α-Reductase," Steroids, 69: 451-460 (2004).
U.S. Appl. No. 12/670,205, filed Jul. 25, 2008, Vitae Pharmaceuticals, Inc.
U.S. Appl. No. 12/670,209, filed Jul. 25, 2008, Vitae Pharmaceuticals, Inc.
U.S. Appl. No. 12/741,522, filed Apr. 30, 2009, Vitae Pharmaceuticals, Inc.
U.S. Appl. No. 12/990,296, filed Apr. 30, 2009, Vitae Pharmaceuticals, Inc.
U.S. Appl. No. 12/745,663, filed Nov. 7, 2008, Vitae Pharmaceuticals, Inc.
U.S. Appl. No. 12/811,577, filed Jan. 7, 2009, Vitae Pharmaceuticals, Inc.
U.S. Appl. No. 12/747,391, filed Dec. 10, 2008, Vitae Pharmaceuticals, Inc.
U.S. Appl. No. 12/863,634, filed Jan. 21, 2009, Vitae Pharmaceuticals, Inc.
U.S. Appl. No. 12/867,374, filed Feb. 13, 2009, Vitae Pharmaceuticals, Inc.
U.S. Appl. No. 12/933,027, filed Mar. 18, 2009, Vitae Pharmaceuticals, Inc.
U.S. Appl. No. 12/741,532, filed Sep. 27, 2010, Vitae Pharmaceuticals, Inc.
U.S. Appl. No. 12/771,499, filed Apr. 30, 2010, Vitae Pharmaceuticals, Inc.
MS Bitar, "Glucocorticoid Dynamics and Impaired Wound Healing in Diabetes Mellitus", Am J Pathol., 1998, vol. 152, pp. 547-554.
MS Bitar, et al., "Heat-Shock Protein 72/73 and Impaired Wound Healing in Diabetic and Hypercortisolemic States", Sugery, 1999, vol. 125, pp. 594-601.
MS Bitar, et al., "Glucocorticoid-Dependent Impairment of Wound Healing in Experimental Diabetes: Amelioration by Adrenalectomy and RU 486", J Surg Res., 1999, vol. 82, pp. 234-243.
MS Bitar, "Insulin and Glucocorticoid-Dependent Suppression of the IGF-I System in Diabetic Wounds", Sugery, 2000, vol. 127, pp. 687-695.
Database Caplus [Online] Chemical Abstracts Service, Maillard et al., "Spiroheterocyclic Cycloalkane Compounds. II. Synthesis of 6-Substituted-Tetrahydro-2H-1,3-Oxazine-2-Ones", XP002516521, retrieved from STN Database accession No. 1969:68280 CAS RN: 20057-45-8 abstract.
Chimica Therapeutica, 1968, vol. 3(5), pp. 321-324, 1968.
Database Caplus [Online] Chemical Abstracts Service, Slyusarenko et al., "Synthesis based on Thionylamides.IV. 2-Alkoxy-5,6-Dihydro-1,3-Oxazines", XP002516522, retrieved from STN Database accession No. 1978:563520 CAS RN: 67868-26-2 abstract.
Zhurnal Organicheskoi Khimii, 1978, vol. 14(5), pp. 1092-1094.
"Khimiia Elementoorganicheskikh Soedineni", 1982, vol. 1982 pp. 22-26.
"Zhurnal Organicheskoi Khimii", 1982, vol. 18, PT 11, p. 2468.
Chemical Abstracts, vol. 98, No. 11, 1983, Columbus, Ohio, US; abstract No. 89280k, Lapkin, et al., "Synthesis of 1,3-oxazin-2,4-diones", p. 552 col. 1, XP002504063 abstract.
Chemical Abstracts, vol. 99, No. 23, 1983, Columbus, Ohio, US; abstract No. 195067b, Saitkulova, et al., "Synthesis involving bromozinc alcoholates of carboxylic acid esters", p. 764 col. 1, XP002504064 abstract.
Goubet, et al., "Conversion of a Thiohydantoin to the Corresponding Hydantoin via a Ring-Opening/Ring Closure Mechanism", Tetrahedron Letters, Elsevier, Amsterdam, 1996, vol. 37, pp. 7727-7730.
Ho-Jane Shue et al., "Cyclic Urea Derivatives as Potent NK1 Selective Antagonists", Bioorganic & Medicinal Chemistry Letters, 2005, vol. 15, pp. 3896-3899.
Ho-Jane Shue et al., "Cyclic Urea Derivatives as Potent NK1 Selective Antagonists. Part II: Effects of Fluoro and Benzylic Methyl Substitutions", Bioorganic & Medicinal Chemistry Letters, 2006, vol. 16, pp. 1065-1069.
Kashima, et al., "Preparation of N-Aryl-2,4-diaminopentanes by the Ring Opening Reaction of 1-Aryl-3,4,5,6-tetrahydro-2-(1H)pyrimidinones", Journal of Heterocyclic Chemistry, vol. 18, 1981, pp. 1595-1596, XP002517485.
Lohray et al., "Enantiospecific Synthesis of 6-Substituted N-Aryl-1,3-Oxazin-2-Ones", Tetrahedron Letters, 1998, vol. 39, pp. 6555-6556.
Malgorzata Wamil and Jonathan R. Seckl, "Inhibition of 11β-hydroxysteroid Dehydrogenase Type 1 as a Promising Therapeutic Target", Drug Discovery Today, 2007, vol. 12, pp. 504-520.

Muehlstadt, et al., "Cyclisation reactions of beta, gamma-unsaturated derivatives of carbonic acid. IX.", Journal Fuer Praktische Chemie, vol. 328, 1986, pp. 163-172, XP002504062 p. 164, compound 4j.

Schoellkopf, et al., "Umsetzungen Alphametallierter Isocyanide Mit Einigen 1,3-Dipolen//Reactions of Alpha-Metalated Osicyanides with Some 1,3-Dipoles", Liebigs Annalen Der Chemie, Verlag Chemie GMBH. Weinheim, DE, 1980, vol. 4, pp. 600-610.

Suga, Seiji et al., ""N-Acyliminium Ion Pool" as a Heterodiene in [4+2] Cycloaddition Reaction", Organic Letters, 2003, vol. 5, pp. 945-947.

Suga, Seiji et al., "Cycloaddition of "N-Acyliminium Ion Pools" with Carbon-Carbon Multiple Bonds", Bulletin of the Chemical Society of Japan, Chemical Society of Japan, 2005, vol. 78, pp. 1206-1217.

Tamaru et al., "Urea as the Most Reactive and Versatile Nitrogen Nucleophile for the Palladium(2+)-Catalyzed Cyclization of Unsaturated Amines", Journal of the American Chemical Society, 1988, vol. 110, pp. 3994-4002.

Yoshida, Masaaki et al., "Selective synthesis of five- and six-membered cyclic carbamates by the reaction of 2-(1-haloalkyl)oxiranes with carbon dioxide and aliphatic primary amines", Heterocycles, Elsevier Science Ltd., 1993, vol. 35 (2), pp. 623-626.

Yoshinao Tamaru, "Palladium(2+)-Catalyzed Intramolecular Aminocarbonylation of 3-Hydroxy-4-pentenylamines and 4-Hydroxy-5-hexenylamines", J. Org. Chem., 1988, pp. 5731-5741.

International Search Report & Written Opinion—(PCT/US2008/009017) Date of Mailing Apr. 12, 2008.

International Search Report & Written Opinion—(PCT/US2008/002517) Date of Mailing Dec. 29, 2008.

International Search Report—(PCT/US2009/002653) Date of Mailing Jul. 3, 2009.

International Search Report—(PCT/US2009/002641) Date of Mailing Jul. 3, 2009.

International Search Report—(PCT/US2009/002629) Date of Mailing Jul. 3, 2009.

International Search Report—(PCT/US2009/002633) Date of Mailing Jul. 3, 2009.

International Search Report—(PCT/US2008/012618) Date of Mailing Dec. 3, 2009.

International Search Report—(PCT/US2009/000057) Date of Mailing Mar. 25, 2009.

International Search Report—(PCT/US2008/013539) Date of Mailing Mar. 19, 2009.

International Search Report—(PCT/US2009/000853) Date of Mailing Sep. 2, 2009.

International Search Report—(PCT/US2009/000421) Date of Mailing Apr. 15, 2009.

International Search Report—(PCT/US2009/000908) Date of Mailing Sep. 17, 2009.

International Search Report—(PCT/US2009/001712) Date of Mailing Jul. 14, 2009.

Database File Registry [Online], Chemical Abstracts Service, Columbus, Ohio, US, 2007, Database accession No. 958700-63-5, Abstract, XP002556893.

Database File Registry [Online], Chemical Abstracts Service, Columbus, Ohio, US, 2007, Database accession No. 958696-39-4, Abstract, XP002556894.

Database File Registry [Online], Chemical Abstracts Service, Columbus, Ohio, US, 2007, Database accession No. 958696-32-7, Abstract, XP002556895.

Database File Registry [Online], Chemical Abstracts Service, Columbus, Ohio, US, 2007, Database accession No. 958629-39-5, Abstract, XP002556896.

Database File Registry [Online], Chemical Abstracts Service, Columbus, Ohio, US, 2007, Database accession No. 958629-22-6, Abstract, XP002556897.

Database File Registry [Online], Chemical Abstracts Service, Columbus, Ohio, US, 2007, Database accession No. 958629-14-6, Abstract, XP002556898.

Database File Registry [Online], Chemical Abstracts Service, Columbus, Ohio, US, 2007, Database accession No. 958625-83-7, Abstract, XP002556899.

Database File Registry [Online], Chemical Abstracts Service, Columbus, Ohio, US, 2007, Database accession No. 958599-31-0, Abstract, XP002556900.

International Search Report—(PCT/US2010/023021) Date of Mailing Aug. 5, 2010.

* cited by examiner

CYCLIC INHIBITORS OF 11β-HYDROXYSTEROID DEHYDROGENASE 1

RELATED APPLICATIONS

This application is the U.S. National Stage of PCT International Application Number PCT/US2009/002629, filed Apr. 30, 2009, which claims the benefit of U.S. Provisional Application No. 61/206,825, filed on Feb. 4, 2009, U.S. Provisional Application No. 61/137,148, filed on Jul. 25, 2008, and U.S. Provisional Application No. 61/049,650, filed May 1, 2008.

PCT/US2009/002629 also claims priority to International Application No. PCT/US2008/009017, which designated the United States and was filed on Jul. 25, 2008, published in English, which claims the benefit of U.S. Provisional Application No. 61/049,650, filed May 1, 2008.

The entire teachings of the above applications are incorporated herein by reference.

FIELD OF THE INVENTION

The present invention relates to inhibitors of 11β-hydroxysteroid dehydrogenase type 1 (11β-HSD1), pharmaceutical compositions thereof and methods of using the same.

BACKGROUND OF THE INVENTION

Glucocorticoids, such as cortisol (hydrocortisone), are steroid hormones that regulate fat metabolism, function and distribution, and play a role in carbohydrate, protein and fat metabolism. Glucocorticoids are also known to have physiological effects on development, neurobiology, inflammation, blood pressure, metabolism, and programmed cell death. Cortisol and other corticosteroids bind both the glucocorticoid receptor (GR) and the mineralocorticoid receptor (MR), which are members of the nuclear hormone receptor superfamily and have been shown to mediate cortisol function in vivo. These receptors directly modulate transcription via DNA-binding zinc finger domains and transcriptional activation domains.

Until recently, the major determinants of glucocorticoid action were attributed to three primary factors: (1) circulating levels of glucocorticoid (driven primarily by the hypothalamic-pituitary-adrenal (HPA) axis); (2) protein binding of glucocorticoids in circulation; and (3) intracellular receptor density inside target tissues. Recently, a fourth determinant of glucocorticoid function has been identified: tissue-specific pre-receptor metabolism by glucocorticoid-activating and -inactivating enzymes. These 11β-hydroxysteroid dehydrogenase (11β-HSD) pre-receptor control enzymes modulate activation of GR and MR by regulation of glucocorticoid hormones. To date, two distinct isozymes of 11-beta-HSD have been cloned and characterized: 11β-HSD1 (also known as 11-beta-HSD type 1, 11betaHSD1, HSD11B1, HDL, and HSD11L) and 11β-HSD2. 11β-HSD1 is a bi-directional oxidoreductase that regenerates active cortisol from inactive 11-keto forms, whereas 11β-HSD2 is a unidirectional dehydrogenase that inactivates biologically active cortisol by converting it into cortisone.

The two isoforms are expressed in a distinct tissue-specific fashion, consistent with the differences in their physiological roles. 11β-HSD1 is widely distributed in rat and human tissues; expression of the enzyme and corresponding mRNA have been detected in human liver, adipose tissue, lung, testis, bone and ciliary epithelium. In adipose tissue, increased cortisol concentrations stimulate adipocyte differentiation and may play a role in promoting visceral obesity. In the eye, 11β-HSD1 may regulate intraocular pressure and may contribute to glaucoma; some data suggest that inhibition of 11β-HSD1 may cause a drop in intraocular pressure in patients with intraocular hypertension (Kotelevstev et al. (1997), Proc. Natl. Acad. Sci. USA 94(26):14924-9). Although 11β-HSD1 catalyzes both 11-beta-dehydrogenation and the reverse 11-oxoreduction reaction, 11β-HSD1 acts predominantly as a NADPH-dependent oxoreductase in intact cells and tissues, catalyzing the formation of active cortisol from inert cortisone (Low et al. (1994) J. Mol. Endocrin. 13: 167-174). In contradistinction, 11β-HSD2 expression is found mainly in mineralocorticoid target tissues such as kidney (cortex and medulla), placenta, sigmoid and rectal colon, salivary gland and colonic epithelial cell lines. 11β-HSD2 acts as an NAD-dependent dehydrogenase catalyzing the inactivation of cortisol to cortisone (Albiston et al. (1994) Mol. Cell. Endocrin. 105: R11-R17), and has been shown to protect the MR from glucocorticoid excess (e.g., high levels of receptor-active cortisol) (Blum, et al. (2003) Prog. Nucl. Acid Res. Mol. Biol. 75:173-216).

Mutations in either the 11β-HSD1 or the 11β-HSD2 genes result in human pathology. For example, individuals with mutations in 11β-HSD2 are deficient in this cortisol-inactivation activity and, as a result, present with a syndrome of apparent mineralocorticoid excess (also referred to as 'SAME') characterized by hypertension, hypokalemia, and sodium retention (Edwards et al. (1988) Lancet 2: 986-989; Wilson et al. (1998) Proc. Natl. Acad. Sci. 95: 10200-10205). Similarly, mutations in 11β-HSD1 and in the gene encoding a co-localized NADPH-generating enzyme, hexose 6-phosphate dehydrogenase (H6PD), can result in cortisone reductase deficiency (CRD); these individuals present with ACTH-mediated androgen excess (hirsutism, menstrual irregularity, hyperandrogenism), a phenotype resembling polycystic ovary syndrome (PCOS) (Draper et al. (2003) Nat. Genet. 34: 434-439).

Notably, disruption of homeostasis in the HPA axis by either deficient or excess secretion or action results in Cushing's syndrome or Addison's disease, respectively (Miller and Chrousos (2001) Endocrinology and Metabolism, eds. Felig and Frohman (McGraw-Hill, New York), 4th Ed.: 387-524). Patients with Cushing's syndrome or receiving glucocorticoid therapy develop reversible visceral fat obesity. The phenotype of Cushing's syndrome patients closely resembles that of Reaven's metabolic syndrome (also known as Syndrome X or insulin resistance syndrome), the symptoms of which include visceral obesity, glucose intolerance, insulin resistance, hypertension, type 2 diabetes and hyperlipidemia (Reaven (1993) Ann. Rev. Med. 44: 121-131). Although the role of glucocorticoids in human obesity is not fully characterized, there is mounting evidence that 11β-HSD1 activity plays an important role in obesity and metabolic syndrome (Bujalska et al. (1997) Lancet 349: 1210-1213); (Livingstone et al. (2000) Endocrinology 131: 560-563; Rask et al. (2001) J. Clin. Endocrinol. Metab. 86: 1418-1421; Lindsay et al. (2003) J. Clin. Endocrinol. Metab. 88: 2738-2744; Wake et al. (2003) J. Clin. Endocrinol. Metab. 88: 3983-3988).

Data from studies in mouse transgenic models supports the hypothesis that adipocyte 11β-HSD1 activity plays a central role in visceral obesity and metabolic syndrome (Alberts et al. (2002) Diabetologia. 45(11): 1526-32). Over-expression in adipose tissue of 11β-HSD1 under the control of the aP2 promoter in transgenic mice produced a phenotype remarkably similar to human metabolic syndrome (Masuzaki et al. (2001) Science 294: 2166-2170; Masuzaki et al. (2003) J.

Clinical Invest. 112: 83-90). Moreover, the increased activity of 11β-HSD1 in these mice is very similar to that observed in human obesity (Rask et al. (2001) J. Clin. Endocrinol. Metab. 86: 1418-1421). In addition, data from studies with 11β-HSD1-deficient mice produced by homologous recombination demonstrate that the loss of 11β-HSD1 leads to an increase in insulin sensitivity and glucose tolerance due to a tissue-specific deficiency in active glucocorticoid levels (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938).

The published data supports the hypothesis that increased expression of 11β-HSD1 contributes to increased local conversion of cortisone to cortisol in adipose tissue and hence that 11β-HSD1 plays a role in the pathogenesis of central obesity and the appearance of the metabolic syndrome in humans (Engeli, et al., (2004) Obes. Res. 12: 9-17). Therefore, 11β-HSD1 is a promising pharmaceutical target for the treatment of the metabolic syndrome (Masuzaki, et al., (2003) Curr. Drug Targets Immune Endocr. Metabol. Disord. 3: 255-62). Furthermore, inhibition of 11β-HSD1 activity may prove beneficial in treating numerous glucocorticoid-related disorders. For example, 11β-HSD1 inhibitors could be effective in combating obesity and/or aspects of the metabolic syndrome cluster, including glucose intolerance, insulin resistance, hyperglycemia, hypertension, and/or hyperlipidemia (Kotelevstev et al. (1997) Proc. Natl. Acad. Sci. 94: 14924-14929; Morton et al. (2001) J. Biol. Chem. 276: 41293-41300; Morton et al. (2004) Diabetes 53: 931-938). In addition, inhibition of 11β-HSD1 activity may have beneficial effects on the pancreas, including the enhancement of glucose-stimulated insulin release (Billaudel and Sutter (1979) Horm. Metab. Res. 11: 555-560; Ogawa et al. (1992) J. Clin. Invest. 90: 497-504; Davani et al. (2000) J. Biol. Chem. 275: 34841-34844).

Furthermore, given that inter-individual differences in general cognitive function have been linked to variability in the long-term exposure to glucocorticoids (Lupien et al. (1998) Nat. Neurosci. 1: 69-73) and dysregulation of the HPA axis resulting in chronic exposure to glucocorticoid excess in certain brain subregions has been theorized to contribute to the decline of cognitive function (McEwen and Sapolsky (1995) Curr. Opin. Neurobiol. 5: 205-216), one might predict that inhibition of 11β-HSD1 could reduce exposure to glucocorticoids in the brain and thereby protect against deleterious glucocorticoid effects on neuronal function, including cognitive impairment, dementia, and/or depression. Notably, it is known that stress and glucocorticoids influence cognitive function (de Quervain et al. (1998) Nature 394: 787-790); and it has been shown that 11β-HSD1, through its control of glucocorticoid action in the brain, may have effects on neurotoxicity (Rajan et al. (1996) Neuroscience 16: 65-70; Seckl (2000) Neuroendocrinol. 18:49-99).

There is also evidence that glucocorticoids and 11β-HSD1 play a role in regulation of in intra-ocular pressure (IOP) (Stokes et al. (2000) Invest. Ophthalmol. Vis. Sci. 41: 1629-1683; Rauz et al. (2001) Invest. Ophthalmol. Vis. Sci. 42: 2037-2042); if left untreated, elevated IOP can lead to partial visual field loss and eventually blindness. Thus, inhibition of 11β-HSD1 in the eye could reduce local glucocorticoid concentrations and IOP, and 11β-HSD1 hence could potentially be used to treat glaucoma and other visual disorders.

Transgenic aP2-11βHSD1 mice exhibit high arterial blood pressure and have increased sensitivity to dietary salt. Moreover, plasma angiotensinogen levels are elevated in the transgenic mice, as are angiotensin II and aldosterone; and treatment of the mice with an angiotensin II antagonist alleviates the hypertension (Masuzaki et al. (2003) J. Clinical Invest. 112: 83-90). This suggests that hypertension may be caused or exacerbated by 11β-HSD1 activity. Thus, 11β-HSD1 inhibitors may be useful for treatment of hypertension and hypertension-related cardiovascular disorders. Inhibition of 11β-HSD1 in mature adipocytes is also expected to attenuate secretion of plasminogen activator inhibitor 1 (PAI-1), which is an independent cardiovascular risk factor (Halleux et al. (1999) J. Clin. Endocrinol. Metabl. 84: 4097-4105).

Glucocorticoids can have adverse effects on skeletal tissues; and prolonged exposure to even moderate glucocorticoid doses can result in osteoporosis (Cannalis (1996) J. Clin. Endocrinol. Metab. 81: 3441-3447). In addition, 11β-HSD1 has been shown to be present in cultures of human primary osteoblasts as well as cells from adult bone (Cooper et al. (2000) Bone 27: 375-381), and the 11β-HSD1 inhibitor carbenoxolone has been shown to attenuate the negative effects of glucocorticoids on bone nodule formation (Bellows et al. (1998) Bone 23: 119-125). Thus, inhibition of 11β-HSD1 is predicted to decrease the local glucocorticoid concentration within osteoblasts and osteoclasts, thereby producing beneficial effects in various forms of bone disease, including osteoporosis.

11β-HSD1 inhibitors may also be useful for immunomodulation. Although glucocorticoids are perceived to suppress the immune system, in actuality, there is a complex, dynamic interaction between the HPA axis and the immune system (Rook (1999) Baillier's Clin. Endocrinol. Metabl. 13: 576-581). Glucocorticoids play a role in modulating the balance between cell-mediated and humoral immune response, with high glucocorticoid activity normally associated with a humoral response. Inhibition of 11β-HSD1 therefore can be used a means of shifting the immune response towards a cell-mediated response. Certain disease states, such as tuberculosis, leprosy (Hansen's disease) and psoriasis, trigger immune responses that are biased towards a humoral response whereas the more effective immune response may be a cell-mediated response. Hence, 11β-HSD1 inhibitors may be useful for treating such diseases.

It has been reported that glucocorticoids inhibit wound healing, especially in diabetic patients with ulcers (Bitar et al. (1999) J. Surg. Res. 82: 234-243; Bitar et al. (1999) Surgery 125: 594-601; Bitar (2000) Surgery 127: 687-695; Bitar (1998) Am. J. Pathol. 152: 547-554). Patients that exhibit impaired glucose tolerance and/or type 2 diabetes often also have impaired wound healing. Glucocorticoids have been shown to increase the risk of infection and delay wound healing (Anstead (1998) Adv. Wound Care 11:277-285). Moreover, there is a correlation between elevated levels of cortisol in wound fluid and non-healing wounds (EP Patent App. No. 0 902 288). Recent published patent applications have suggested that certain 11β-HSD1 inhibitors may be useful for promoting wound healing (PCT/US2006/043, 951).

As evidenced herein, there is a continuing need for new and improved drugs that inhibit 11β-HSD1. The novel compounds of the instant invention are effective inhibitors of 11β-HSD1.

SUMMARY OF THE INVENTION

It has now been found that compounds of Formula I or pharmaceutically acceptable salts thereof, are effective inhibitors of 11β-HSD1.

The invention is a compound represented by Formula (I)

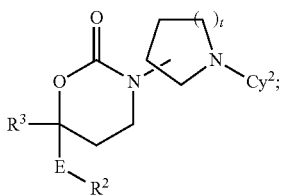

(I)

or a pharmaceutically acceptable salt, enantiomer or diastereomer thereof.

In a first embodiment of the invention, Formula I and its constituent members are defined herein as follows:

t is 1, 2 or 3;

the pyrrolidine, piperidine or azepane ring is optionally substituted with 1 or 2 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclylsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, $(C_3-C_6)$cycloalkylcarbonyl, $(C_3-C_6)$cycloalkylaminocarbonyl, {$(C_3-C_6)$cycloalkyl}{$(C_1-C_6)$alkyl}aminocarbonyl, di$(C_3-C_6)$cycloalkylaminocarbonyl, $(C_3-C_6)$cycloalkylaminosulfonyl, {$(C_3-C_6)$cycloalkyl}{$(C_1-C_6)$alkyl}aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, {$(C_3-C_6)$cycloalkyl}{$(C_1-C_6)$alkyl}aminocarbonyl$(C_1-C_6)$alkyl and di$(C_3-C_6)$cycloalkylaminocarbonyl$(C_1-C_6)$alkyl;

$Cy^2$ is a pyridyl, pyridazinyl, pyrimidinyl, pyrazinyl, thiadiazolyl, thiazolyl or pyrazolyl and is optionally substituted with 1 to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, E is (a) a bond or (b) $(C_1-C_3)$alkylene or $(C_1-C_2)$alkylenyloxy, wherein the O is attached to $R^2$, each of which is optionally substituted with 1 to 4 groups independently selected from methyl, ethyl, trifluoromethyl or oxo;

$R^2$ is $(C_1-C_6)$alkyl, aryl, heteroaryl, cycloalkyl or heterocyclyl and is optionally substituted with up to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_{C6})$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cyclo-alkylalkanesulfonyl, $(C_1-C_6)$alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2$NCO, $H_2$N$SO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclylsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy, ($C_1$-$C_6$)alkylcarbonyl, ($C_3$-$C_6$)cycloalkylcarbonyl, ($C_3$-$C_6$)cycloalkylaminocarbonyl, {($C_3$-$C_6$)cycloalkyl}{($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$)cycloalkyl}{($C_1$-$C_6$)alkyl}aminosulfonyl, di($C_3$-$C_6$)cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$)alkyl, ($C_3$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl and di($C_3$-$C_6$)cycloalkylaminocarbonyl($C_1$-$C_6$)alkyl;

$R^3$ is selected from ($C_1$-$C_6$)alkyl, ($C_2$-$C_6$)alkenyl, ($C_2$-$C_6$)alkynyl, ($C_3$-$C_6$)cycloalkyl($C_1$-$C_4$)alkyl, ($C_1$-$C_3$)alkoxy($C_1$-$C_3$)alkoxy, or ($C_1$-$C_3$)alkoxy($C_1$-$C_3$)alkyl and is optionally substituted with up to four groups independently selected from fluorine, cyano, oxo, $R^4$, $R^4$O—, $(R^4)_2$N—, $R^4O_2$C—, $R^4$C(=O)O—, $R^4$S, $R^4$S(=O)—, $R^4$S(=O)$_2$—, $R^4$C(=O)N$R^4$—, $(R^4)_2$NC(=O)—, $(R^4)_2$NC(=O)O—, $(R^4)_2$NC(=O)N$R^4$—, $R^4$OC(=O)N$R^4$—, $(R^4)_2$NC(=NCN)N$R^4$—, $(R^4$O$)_2$P(=O)O—, $(R^4$O$)_2$P(=O)N$R^4$—, $R^4$OS(=O)$_2$N$R^4$—, $(R^4)_2$NS(=O)$_2$O—, $(R^4)_2$NS(=O)$_2$N$R^4$—, $R^4$S(=O)$_2$N$R^4$—, $R^4$S(=O)$_2$NHC(=O)—, $R^4$S(=O)$_2$NHC(=O)O—, $R^4$S(=O)$_2$NHC(=O)N$R^4$—, $R^4$OS(=O)$_2$NHC(=O)—, $R^4$OS(=O)$_2$NHC(=O)O—, $R^4$OS(=O)$_2$NHC(=O)N$R^4$—, $(R^4)_2$NS(=O)$_2$NHC(=O)—, $(R^4)_2$NS(=O)$_2$NHC(=O)O—, $(R^4)_2$NS(=O)$_2$NHC(=O)N$R^4$—, $R^4$C(=O)NHS(=O)$_2$—, $R^4$C(=O)NHS(=O)$_2$O—, $R^4$C(=O)NHS(=O)$_2$N$R^4$—, $R^4$OC(=O)NHS(=O)$_2$—, $R^4$OC(=O)NHS(=O)$_2$O—, $R^4$OC(=O)NHS(=O)$_2$N$R^4$—, $(R^4)_2$NC(=O)NHS(=O)$_2$—, $(R^4)_2$NC(=O)NHS(=O)$_2$O—, $(R^4)_2$NC(=O)NHS(=O)$_2$N$R^4$—, spirocycloalkyl; heterocyclyl (which in turn may be optionally substituted with alkyl, haloalkyl, halogen or oxo), heteroaryl (which in turn may be optionally substituted with alkyl, haloalkyl, alkoxy, alkylthio, alkylsulfonyl, halogen, trifluoromethyl, dialkylamino, nitro, cyano, $CO_2$H, CON$H_2$, N-monoalkyl-substituted amido, N,N-dialkyl-substituted amido, or oxo), arylamino (which in turn may be optionally substituted with alkyl, alkoxy, alkylthio, alkylsulfonyl, halogen, trifluoromethyl, dialkylamino, nitro, cyano, $CO_2$H, CON$H_2$, N-monoalkyl-substituted amido and N,N-dialkyl-substituted amido) and heteroarylamino (which in turn may be optionally substituted with alkyl, haloalkyl, alkoxy, alkylthio, alkylsulfonyl, halogen, trifluoromethyl, dialkylamino, nitro, cyano, $CO_2$H, CON$H_2$, N-monoalkyl-substituted amido, N,N-dialkyl-substituted amido, or oxo); and $R^4$ is independently selected from H, ($C_1$-$C_6$)alkyl, halo($C_1$-$C_6$)alkyl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl, hydroxy($C_1$-$C_6$)alkyl and ($C_1$-$C_6$)alkoxy($C_1$-$C_6$)alkyl.

Another embodiment of the invention is a pharmaceutical composition comprising i) a pharmaceutically acceptable carrier or diluent, and ii) a compound of Formulas I, II, Iu$^{1-20}$, Iv$^{1-20}$, Iw$^{1-20}$ or Ix$^{1-7}$, or a pharmaceutically acceptable salt, enantiomer or diastereomer thereof.

Another embodiment of the invention is a method of inhibiting 11β-HSD1 activity comprising the step of administering to a mammal in need of such treatment an effective amount of a compound of Formulas I, II, Iu$^{1-20}$, Iv$^{1-20}$, Iw$^{1-20}$ or Ix$^{1-7}$, or a pharmaceutically acceptable salt, enantiomer or diastereomer thereof.

Another embodiment of the invention is a method of treating a subject with a disease associated with the activity or expression of 11β-HSD1, comprising the step of administering to the subject an effective amount of a compound of Formulas I, II, Iu$^{1-20}$, Iv$^{1-20}$, Iw$^{1-20}$ or Ix$^{1-7}$, or a pharmaceutically acceptable salt, enantiomer or diastereomer thereof.

Another embodiment of the invention is the use of a compound of Formulas I, II, Iu$^{1-20}$, Iv$^{1-20}$, Iw$^{1-20}$ or Ix$^{1-7}$, or a pharmaceutically acceptable salt, enantiomer or diastereomer thereof for the manufacture of a medicament for inhibiting 11β-HSD1 activity in a mammal in need of such treatment.

Another embodiment of the invention is the use of a compound of Formulas I, II, Iu$^{1-20}$, Iv$^{1-20}$, Iw$^{1-20}$ or Ix$^{1-7}$, or a pharmaceutically acceptable salt, enantiomer or diastereomer thereof for the manufacture of a medicament for treating a subject with a disease associated with the activity or expression of 11β-HSD1.

Another embodiment of the invention is a compound of Formulas I, II, Iu$^{1-20}$, Iv$^{1-20}$, Iw$^{1-20}$ or Ix$^{1-7}$, or a pharmaceutically acceptable salt, enantiomer or diastereomer thereof for use in inhibiting 11β-HSD1 activity in a mammal in need of such treatment.

Another embodiment of the invention is a compound of I, II, Iu$^{1-20}$, Iv$^{1-20}$, Iw$^{1-20}$ or Ix$^{1-7}$, or a pharmaceutically acceptable salt, enantiomer or diastereomer thereof for use in for treating a subject with a disease associated with the activity or expression of 11β-HSD1.

DETAILED DESCRIPTION OF THE INVENTION

Another embodiment of the invention is a compound of Formula II:

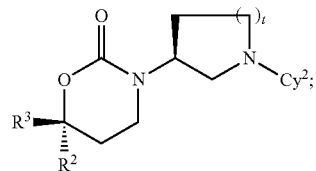

or a pharmaceutically acceptable salt, enantiomer or diastereomer thereof;

t is 1, 2 or 3;

$Cy^2$ is pyridyl optionally substituted by 1 to 4 groups independently selected from halo, hydroxy, methoxy, hydroxymethyl, methoxycarbonyl, amino, carbamoyl, methylcarbamoyl, dimethylcarbamoyl, (2-methoxyethyl)aminocarbonyl, acetylaminomethyl, methylsulfonyl, methylsulfonylamino, methylaminosulfonyl, isopropylaminosulfonyl, dimethylaminosulfonyl, pyrrolidine-1-sulfonyl, methylsulfonylaminomethyl, tetrazolyl, methyl, trifluoromethyl, acetyl, 2-hydroxyethyl and 1-aminoethyl;

R² is phenyl, thienyl, pyridyl or isopropyl each optionally substituted with halo, methyl, methylthio or (4-morpholino) methyl; and R³ is methyl, ethyl, propyl, butyl, vinyl, allyl or ethoxyethyl each optionally substituted with up to two groups independently selected from methyl, HO—, MeO—, H₂N—, MeC(=O)NH—, MeS(=O)₂NH—, H₂NC(=O)—, MeNHC(=O)—, HO₂C—, (HO)₂P(=O)O—, H₂NS(=O)₂O—, H₂NS(=O)₂NH—, MeNHC(=O)NH—, MeNHC(=O)O—, oxo, cyano, HO₂C—, HOCH₂CH₂NH—, 4-morpholino, HOCH₂C(=O)NH—, H₂NCH₂C(=O)NH—, EtNHC(=O)NH, MeOC(=O)NH—, MeNHC(=NCaN)NH—, Me-, MeS—, MeSO₂-MeSO₂N(Me)-, MeS(=O)₂NHC(=O)—, imidazolylamino-, imidazolyl, tetrazolyl, H₂NCONH—, H₂NCO₂—, HOCH₂CH₂O—, MeNH—, Me₂N— and MeCONMe.

Another embodiment of the invention is a compound of Formula II, or a pharmaceutically acceptable salt, enantiomer or diastereomer thereof; t is 1, 2, or 3; Cy² is optionally substituted pyridazinyl or thiazolyl; R² is (C₁-C₆)alkyl, aryl, heteroaryl, cycloalkyl or heterocyclyl and is optionally substituted with up to 4 groups independently selected from fluorine, chlorine, bromine, iodine, cyano, nitro, amino, hydroxy, carboxy, (C₁-C₆)alkyl, hydroxy(C₁-C₆)alkyl, (C₃-C₆)cycloalkyl, hydroxy(C₃-C₆)cycloalkyl, (C₄-C₇)cycloalkylalkyl, (C₂-C₆)alkenyl, halo(C₂-C₆)alkenyl, hydroxy(C₂-C₆)alkenyl, (C₂-C₆)alkynyl, (C₃-C₆)cycloalkyl(C₂-C₄)alkynyl, halo(C₁-C₆)alkyl, halo(C₃-C₆)cycloalkyl, halo(C₄-C₇)cycloalkylalkyl, (C₁-C₆)alkoxy, (C₃-C₆)cycloalkoxy, (C₄-C₇)cycloalkylalkoxy, halo(C₁-C₆)alkoxy, halo(C₃-C₆)cycloalkoxy, halo(C₄-C₇)cycloalkylalkoxy, (C₁-C₆)alkylthio, (C₃-C₆)cycloalkythio, (C₄-C₇)cycloalkylalkylthio, halo(C₁-C₆)alkylthio, halo(C₃-C₆)cycloalkythio, halo(C₄-C₇)cycloalkylalkylthio, (C₁-C₆)alkanesulfinyl, (C₃-C₆)cycloalkanesulfinyl, (C₄-C₇)cycloalkylalkanesulfinyl, halo(C₁-C₆)alkanesulfinyl, halo(C₃-C₆)cycloalkanesulfinyl, halo(C₄-C₇)cycloalkylalkanesulfinyl, (C₁-C₆)alkanesulfonyl, (C₃-C₆)cycloalkanesulfonyl, (C₄-C₇)cycloalkylalkanesulfonyl, halo(C₁-C₆)alkanesulfonyl, halo(C₃-C₆)cycloalkanesulfonyl, halo(C₄-C₇)cycloalkylalkanesulfonyl, (C₁-C₆)alkylamino, di(C₁-C₆)alkylamino, (C₁-C₆)alkoxy(C₁-C₆)alkoxy, halo(C₁-C₆)alkoxy(C₁-C₆)alkoxy, (C₁-C₆)alkoxycarbonyl, H₂NCO, H₂NSO₂, (C₁-C₆)alkylaminocarbonyl, di(C₁-C₆)alkylaminocarbonyl, (C₁-C₃)alkoxy(C₁-C₃alkyl-aminocarbonyl, heterocyclylcarbonyl, (C₁-C₆)alkylaminosulfonyl, di(C₁-C₆)alkylaminosulfonyl, heterocyclylsulfonyl, (C₁-C₆)alkylcarbonylamino, (C₁-C₆)alkylcarbonylamino(C₁-C₆)alkyl, (C₁-C₆)alkylsulfonylamino, (C₁-C₆)alkylsulfonylamino(C₁-C₆)alkyl, (C₁-C₆)alkoxycarbonyl(C₁-C₆)alkoxy, (C₁-C₆)alkoxy(C₁-C₆)alkyl, halo(C₁-C₆)alkoxy(C₁-C₆)alkyl, hydroxy(C₁-C₆)alkoxy, heteroaryl, oxo, amino(C₁-C₆)alkyl, (C₁-C₆)alkylamino(C₁-C₆)alkyl, di(C₁-C₆)alkylamino(C₁-C₆)alkyl amino(C₂-C₆)alkoxy, (C₁-C₆)alkylamino(C₂-C₆)alkoxy, di(C₁-C₆)alkylamino(C₂-C₆)alkoxy and (C₁-C₆)alkylcarbonyl; and R³ is as defined above in the first embodiment.

Another embodiment of the invention is a compound of any one of Formulas Iu$^{1-20}$ or a pharmaceutically acceptable salt, enantiomer or diastereomer thereof:

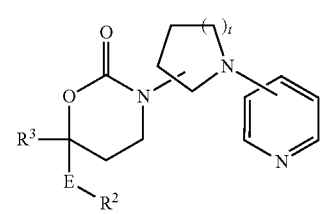

Iu¹

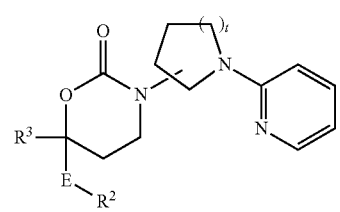

Iu²

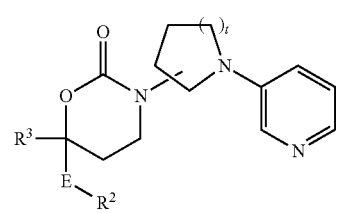

Iu³

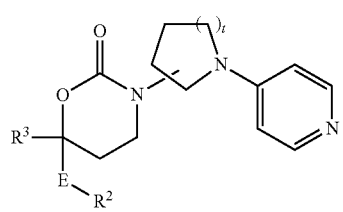

Iu⁴

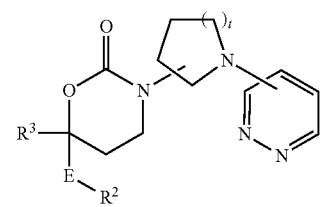

Iu⁵

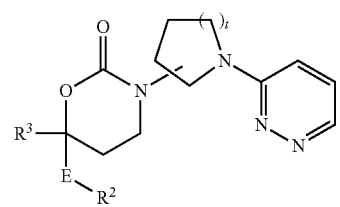

Iu⁶

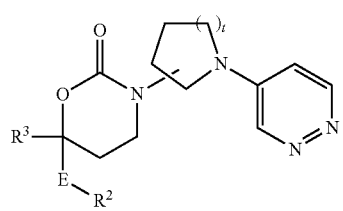

Iu⁷

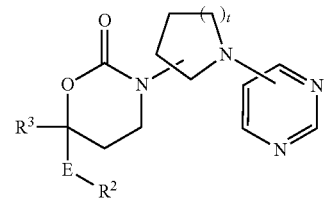 Iu⁸

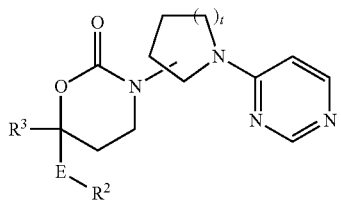 Iu⁹

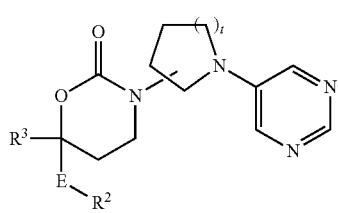 Iu¹⁰

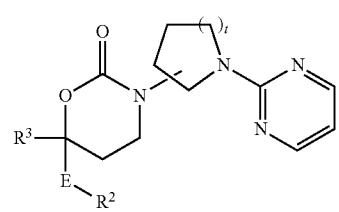 Iu¹¹

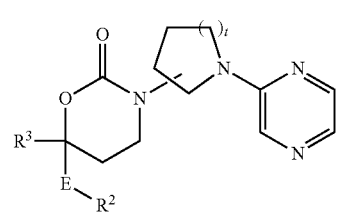 Iu¹²

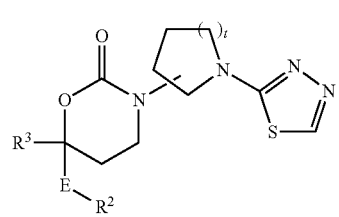 Iu¹³

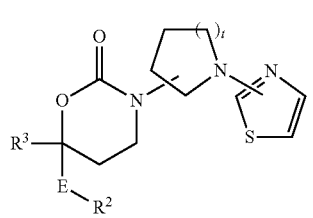 Iu¹⁴

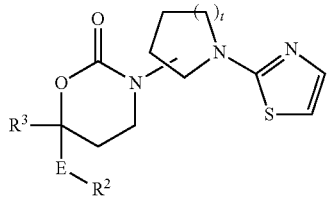 Iu¹⁵

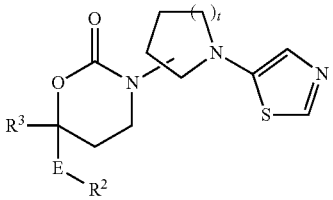 Iu¹⁶

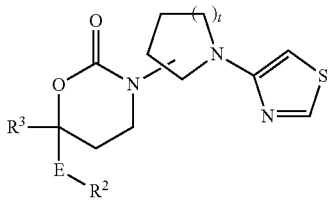 Iu¹⁷

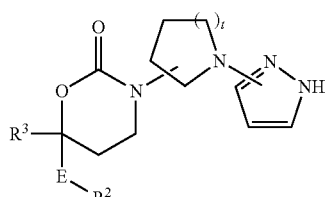 Iu¹⁸

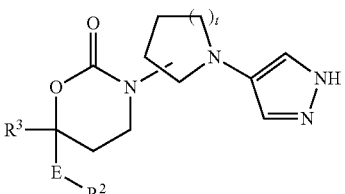 Iu¹⁹

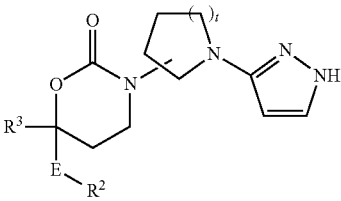 Iu²⁰

In Formulas Iu$^{1-20}$, the pyridine, pyridazine, pyrimidine, pyrazine, pyrazole, thiazole and thiadiazole rings are optionally substituted (substitution at ring carbons bonded to hydrogen and ring nitrogen atoms bonded to hydrogen atoms are encompassed, i.e., a "substitutable ring nitrogen atom") with up to four substituents as described for Cy² in the first embodiment; and the pyrrolidine, piperidine and azepane rings are optionally substituted with 0, 1 or 2 substituents as described in the first embodiment. Suitable substituents for pyrrolidine, piperidine and azepane rings and Cy² and suitable values for R², R³ and E are as defined above in the first embodiment; and t is 1, 2 or 3. Alternatively, suitable substituents for the pyrrolidine, piperidine and azepane rings and the pyridine, pyridazine, pyrimidine, pyrazine, pyrazole, thiazole and thiadiazole rings in Formulas Iu$^{1-20}$ are independently fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclylsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, $(C_3-C_6)$cycloalkylcarbonyl, $(C_3-C_6)$cycloalkylaminocarbonyl, $\{(C_3-C_6)$cycloalkyl$\}\{(C_1-C_6)$alkyl$\}$aminocarbonyl, di$(C_3-C_6)$cycloalkylaminocarbonyl, $(C_3-C_6)$cycloalkylaminosulfonyl, $\{(C_3-C_6)$cycloalkyl$\}\{(C_1-C_6)$alkyl$\}$aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, $\{(C_3-C_6)$cycloalkyl$\}\{(C_1-C_6)$alkyl$\}$aminocarbonyl$(C_1-C_6)$alkyl and di$(C_3-C_6)$cycloalkylaminocarbonyl$(C_1-C_6)$alkyl; values for $R^2$, $R^3$ and E are as defined above in the first embodiment; and t is 1, 2 or 3. Alternatively, suitable substituents for the pyrrolidine, piperidine and azepane rings include oxo, $(C_1-C_4)$alkyl, $(C_1-C_4)$alkoxy, $(C_1-C_4)$haloalkyl, $(C_1-C_4)$haloalkoxy, halogen, cyano and nitro; suitable substituents for a substitutable ring nitrogen atom in the pyrazole rings in Formulas Iu$^{18-20}$ include $(C_1-C_4)$alkyl, $(C_3-C_4)$cycloalkyl, $(C_3-C_4)$cycloalkyl$(C_1-C_2)$alkyl, and $(C_1-C_4)$haloalkyl; suitable substituents for a ring carbon atom in the pyridine, pyridazine, pyrimidine, pyrazine, pyrazole, thiazole and thiadiazole rings in Formulas Iu$^{1-20}$ include fluorine, chlorine, cyano, hydroxy, amino, $(C_1-C_4)$alkyl, $(C_3-C_4)$cycloalkyl, $(C_3-C_4)$cycloalkyl$(C_1-C_2)$alkyl, halo$(C_1-C_4)$alkyl, $(C_1-C_4)$alkoxy, $(C_1-C_4)$haloalkoxy, $CONH_2$, $(C_1-C_4)$alkylaminocarbonyl, di$(C_1-C_4)$alkylaminocarbonyl, $(C_3-C_4)$cycloalkylaminocarbonyl, $\{(C_1-C_4)$alkyl$\}\{(C_3-C_4)$cycloalkyl$\}$aminocarbonyl and $(C_1-C_4)$alkylcarbonylamino; the ring nitrogen in the pyridine rings in Formulas Iu$^{1-4}$ is optionally substituted by oxo; t is 1, 2 or 3; and suitable values for $R^2$, $R^3$ and E are as defined above in the first embodiment.

Alternatively, for each of the embodiments described in the paragraph immediately following Formulas Iu$^{1-20}$, $R^3$ is preferably $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

Alternatively, for each of the embodiments described in the paragraph immediately following Formulas Iu$^{1-20}$, $R^3$ is preferably $H_2NC(=O)CMe_2CH_2$, 3-hydroxy-3-methylbutyl, 2-hydroxy-2-methylpropyl or 2-cyano-2-methylpropyl.

Alternatively, for each of the embodiments described in the paragraph immediately following Formulas Iu$^{1-20}$, $R^2$ is preferably phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is preferably $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

Alternatively, for each of the embodiments described in the paragraph immediately following Formulas Iu$^{1-23}$, $R^2$ is preferably phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is preferably $H_2NC(=O)CMe_2CH_2$, 3-hydroxy-3-methylbutyl, 2-hydroxy-2-methylpropyl or 2-cyano-2-methylpropyl.

Alternatively, for each of the embodiments described in the paragraph immediately following Formulas Iu$^{1-20}$, t is preferably 2; $R^2$ is preferably phenyl or fluorophenyl; and $R^3$ is preferably 2-hydroxy-2-methylpropyl or 2-cyano-2-methylpropyl.

Alternatively, for each of the embodiment described in the paragraph immediately following Formulas Iu$^{1-20}$, wherein t is 2; $R^2$ is preferably phenyl or fluorophenyl; $R^3$ preferably is 2-hydroxy-2-methylpropyl or 2-cyano-2-methylpropyl; one or two ring carbon atoms in the pyridine, pyridazine, pyrimidine, pyrazine, pyrazole, thiazole and thiadiazole rings in Formulas Iu$^{1-20}$ are optionally substituted with fluoro, chloro, cyano, $CONH_2$, $CONHMe$, $CONMe_2$, $CONHc$-Pr, methyl, ethyl or $CF_3$; the substitutable ring nitrogen atom in the pyrazole rings in Formulas Iu$^{18-20}$ are optionally substituted with $(C_1-C_4)$alkyl, $(C_3-C_4)$cycloalkyl, $(C_3-C_4)$cycloalkyl$(C_1-C_2)$alkyl, and $(C_1C_2)$haloalkyl; the ring nitrogen in the pyridine rings in Formulas Iu$^{1-4}$ are optionally substituted by oxo.

Another embodiment of the invention is a compound of any one of Formulas Iv$^{1-20}$, or a pharmaceutically acceptable salt, enantiomer or diastereomer thereof:

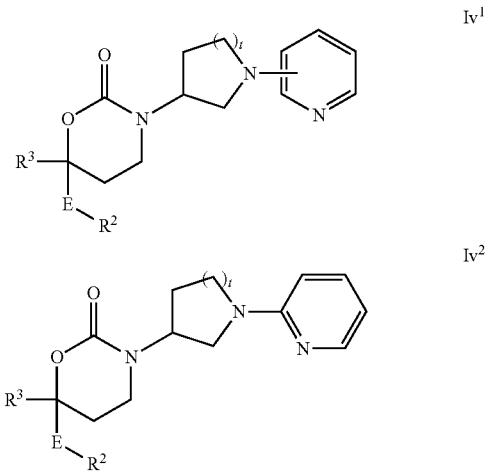

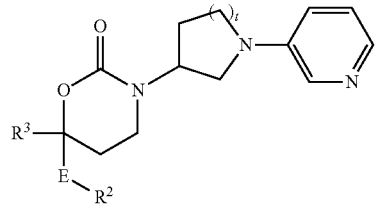 Iv³
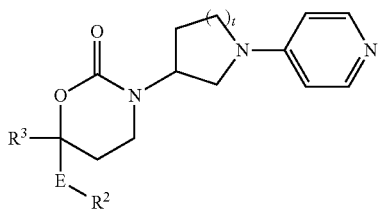 Iv⁴
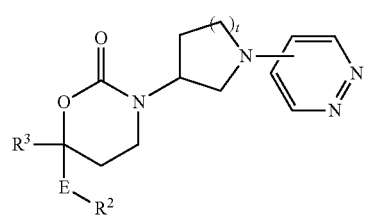 Iv⁵
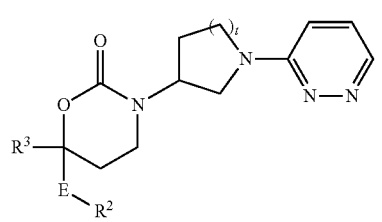 Iv⁶
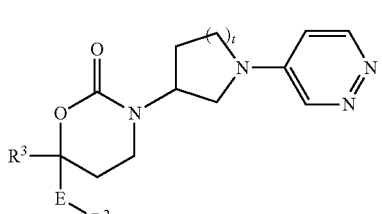 Iv⁷
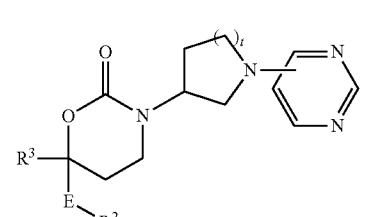 Iv⁸
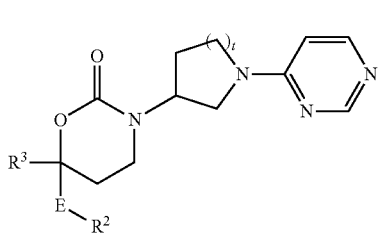 Iv⁹
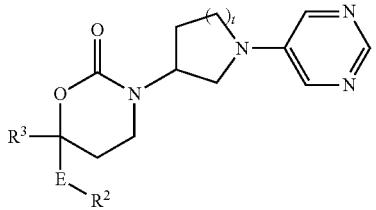 Iv¹⁰
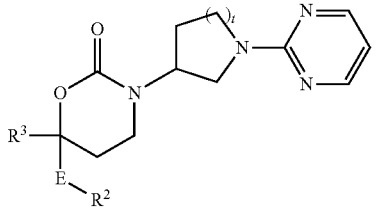 Iv¹¹
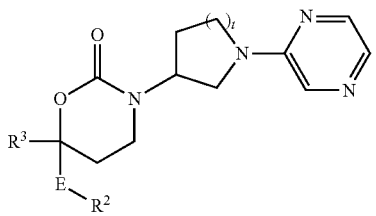 Iv¹²
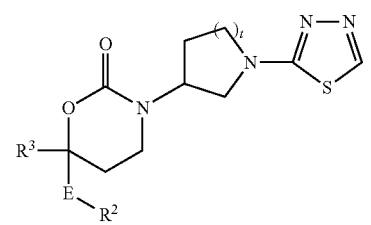 Iv¹³
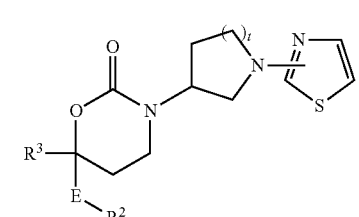 Iv¹⁴
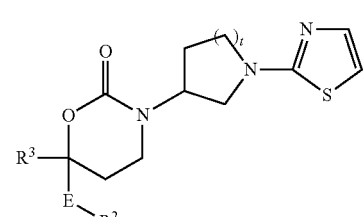 Iv¹⁵
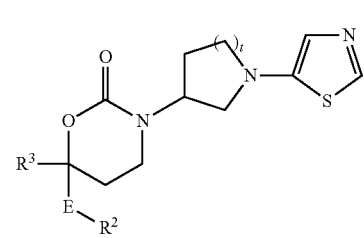 Iv¹⁶

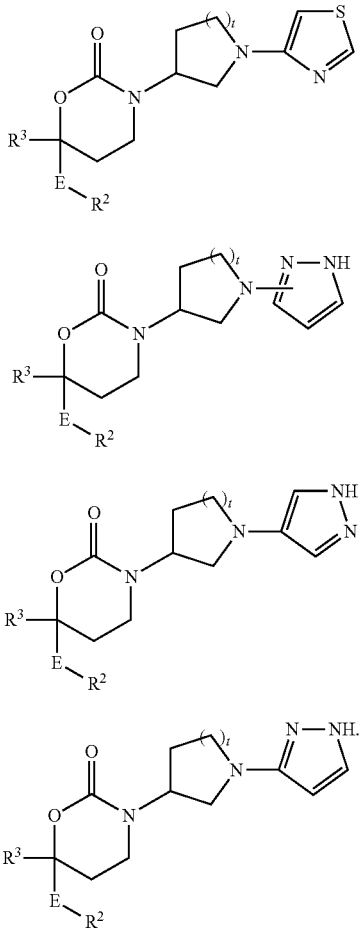

In Formulas Iv$^{1-20}$, the pyridine, pyridazine, pyrimidine, pyrazine, pyrazole, thiazole and thiadiazole rings are optionally substituted (substitution at ring carbons bonded to hydrogen and ring nitrogen atoms bonded to hydrogen atoms are encompassed, i.e., a "substitutable ring nitrogen atom") with up to four substituents as described for Cy$^2$ in the first embodiment. Suitable substituents for Cy$^2$ and suitable values for R$^2$, R$^3$ and E are as defined above in the first embodiments. t is 1, 2 or 3. Alternatively, suitable substituents for the pyrrolidine, piperidine and azepane rings and the pyridine, pyridazine, pyrimidine, pyrazine, pyrazole, thiazole and thiadiazole rings in Formulas Iv$^{1-20}$ are independently fluorine, chlorine, bromine, iodine, cyano, nitro, amino, hydroxy, carboxy, (C$_1$-C$_6$)alkyl, hydroxy(C$_1$-C$_6$)alkyl, (C$_3$-C$_6$)cycloalkyl, hydroxy(C$_3$-C$_6$)cycloalkyl, (C$_4$-C$_7$)cycloalkylalkyl, (C$_2$-C$_6$)alkenyl, halo(C$_2$-C$_6$)alkenyl, hydroxy(C$_2$-C$_6$)alkenyl, (C$_2$-C$_6$)alkynyl, (C$_3$-C$_6$)cycloalkyl(C$_2$-C$_4$)alkynyl, halo(C$_1$-C$_6$)alkyl, halo(C$_3$-C$_6$)cycloalkyl, halo(C$_4$-C$_7$)cycloalkylalkyl, (C$_1$-C$_6$)alkoxy, (C$_3$-C$_6$)cycloalkoxy, (C$_4$-C$_7$)cycloalkylalkoxy, halo(C$_1$-C$_6$)alkoxy, halo(C$_3$-C$_6$)cycloalkoxy, halo(C$_4$-C$_7$)cycloalkylalkoxy, (C$_1$-C$_6$)alkylthio, (C$_3$-C$_6$)cycloalkythio, (C$_4$-C$_7$)cycloalkylalkylthio, halo(C$_1$-C$_6$)alkylthio, halo(C$_3$-C$_6$)cycloalkythio, halo(C$_4$-C$_7$)cycloalkylalkylthio, (C$_1$-C$_6$)alkanesulfinyl, (C$_3$-C$_6$)cycloalkanesulfinyl, (C$_4$-C$_7$)cycloalkylalkanesulfinyl, halo(C$_1$-C$_6$)alkanesulfinyl, halo(C$_3$-C$_6$)cycloalkanesulfinyl, halo(C$_4$-C$_7$)cycloalkylalkanesulfinyl, (C$_1$-C$_6$)alkanesulfonyl, (C$_3$-C$_6$)cycloalkanesulfonyl, (C$_4$-C$_7$)cycloalkylalkanesulfonyl, halo (C$_1$-C$_6$)alkanesulfonyl, halo(C$_3$-C$_6$)cycloalkanesulfonyl, halo(C$_4$-C$_7$)cycloalkylalkanesulfonyl, (C$_1$-C$_6$)alkylamino, di(C$_1$-C$_6$)alkylamino, (C$_1$-C$_6$)alkoxy(C$_1$-C$_6$)alkoxy, halo (C$_1$-C$_6$)alkoxy(C$_1$-C$_6$)alkoxy, (C$_1$-C$_6$)alkoxycarbonyl, H$_2$NCO, H$_2$NSO$_2$, (C$_1$-C$_6$)alkylaminocarbonyl, di(C$_1$-C$_6$) alkylaminocarbonyl, (C$_1$-C$_3$)alkoxy(C$_1$-C$_3$)alkylaminocarbonyl, heterocyclylcarbonyl, (C$_1$-C$_6$)alkylaminosulfonyl, di(C$_1$-C$_6$)alkylaminosulfonyl, heterocyclylsulfonyl, (C$_1$-C$_6$) alkylcarbonylamino, (C$_1$-C$_6$)alkylcarbonylamino(C$_1$-C$_6$) alkyl, (C$_1$-C$_6$)alkylsulfonylamino, (C$_1$-C$_6$)alkylsulfonylamino(C$_1$-C$_6$)alkyl, (C$_1$-C$_6$)alkoxycarbonyl(C$_1$-C$_6$)alkoxy, (C$_1$-C$_6$)alkoxy(C$_1$-C$_6$)alkyl, halo(C$_1$-C$_6$)alkoxy(C$_1$-C$_6$) alkyl, hydroxy(C$_1$-C$_6$)alkoxy, heteroaryl, amino(C$_1$-C$_6$) alkyl, (C$_1$-C$_6$)alkylamino(C$_1$-C$_6$)alkyl, di(C$_1$-C$_6$)alkylamino (C$_1$-C$_6$)alkyl amino(C$_2$-C$_6$)alkoxy, (C$_1$-C$_6$)alkylamino(C$_2$-C$_6$)alkoxy, di(C$_1$-C$_6$)alkylamino(C$_2$-C$_6$)alkoxy, (C$_1$-C$_6$) alkylcarbonyl, (C$_3$-C$_6$)cycloalkylcarbonyl, (C$_3$-C$_6$) cycloalkylaminocarbonyl, {(C$_3$-C$_6$)cycloalkyl}{(C$_1$-C$_6$) alkyl}aminocarbonyl, di(C$_3$-C$_6$)cycloalkylaminocarbonyl, (C$_3$-C$_6$)cycloalkylaminosulfonyl, {(C$_3$-C$_6$)cycloalkyl}{(C$_1$-C$_6$)alkyl}aminosulfonyl, di(C$_3$-C$_6$)cycloalkylaminosulfonyl, cyano(C$_1$-C$_6$)alkyl, aminocarbonyl(C$_1$-C$_6$)alkyl, (C$_1$-C$_6$)alkylaminocarbonyl(C$_1$-C$_6$)alkyl, di(C$_1$-C$_6$) alkylaminocarbonyl(C$_1$-C$_6$)alkyl, (C$_3$-C$_6$) cycloalkylaminocarbonyl(C$_1$-C$_6$)alkyl, {(C$_3$-C$_6$) cycloalkyl}{(C$_1$-C$_6$)alkyl}aminocarbonyl(C$_1$-C$_6$)alkyl and di(C$_3$-C$_6$)cycloalkylaminocarbonyl(C$_1$-C$_6$)alkyl; t is 1, 2 or 3 and values for R$^2$, R$^3$ and E are as defined above in the first embodiment. Alternatively, suitable substituents for the pyrrolidine, piperidine and azepane rings include oxo, (C$_1$-C$_4$) alkyl, (C$_1$-C$_4$)alkoxy, (C$_1$-C$_4$)haloalkyl, (C$_1$-C$_4$)haloalkoxy, halogen, cyano and nitro; suitable substituents for a substitutable ring nitrogen atom in the pyrazole rings in Formulas Iv$^{18-20}$ include (C$_1$-C$_4$)alkyl, (C$_3$-C$_4$)cycloalkyl, (C$_3$-C$_4$)cycloalkyl(C$_1$-C$_2$)alkyl, and (C$_1$-C$_4$)haloalkyl; suitable substituents for a ring carbon atom in the pyridine, pyridazine, pyrimidine, pyrazine, pyrazole, thiazole and thiadiazole rings in Formulas Iv$^{1-20}$ include fluorine, chlorine, cyano, hydroxy, amino, (C$_1$-C$_4$)alkyl, (C$_3$-C$_4$)cycloalkyl, (C$_3$-C$_4$)cycloalkyl (C$_1$-C$_2$)alkyl, halo(C$_1$-C$_4$)alkyl, (C$_1$-C$_4$)alkoxy, (C$_1$-C$_4$)haloalkoxy, CONH$_2$, (C$_1$-C$_4$)alkylaminocarbonyl, di(C$_1$-C$_4$) alkylaminocarbonyl, (C$_3$-C$_4$)cycloalkylaminocarbonyl, {(C$_1$-C$_4$)alkyl}{(C$_3$-C$_4$)cycloalkyl}aminocarbonyl and (C$_1$-C$_4$)alkylcarbonylamino; the ring nitrogen in the pyridine rings in Formulas Iv$^{1-4}$ is optionally substituted by oxo; t is 1, 2 or 3; and suitable values for R$^2$, R$^3$ and E are as defined above in the first embodiment.

For each of the embodiments described in the paragraph immediately following Formulas Iv$^{1-20}$, R$^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas Iv$^{1-20}$, R$^3$ is H$_2$NC(=O) CMe$_2$CH$_2$, 3-hydroxy-3-methylbutyl, 2-hydroxy-2-methylpropyl or 2-cyano-2-methylpropyl.

For each of the embodiments described in the paragraph immediately following Formulas Iv$^{1-20}$, R$^2$ is phenyl optionally substituted with 1, 2 or 3 substituents selected from halo, cyano, CONH$_2$, (C$_1$-C$_4$)alkyl, (C$_1$-C$_4$)haloalkyl and SO$_2$Me; and R$^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

For each of the embodiments described in the paragraph immediately following Formulas Iv$^{1-20}$, R$^2$ is phenyl optionally substituted with 1, 2 or 3 substituents selected from halo, cyano, $CONH_2$, $(C_1-C_4)$alkyl, $(C_1-C_4)$haloalkyl and $SO_2Me$; and $R^3$ is $H_2NC(\!=\!O)CMe_2CH_2$, 3-hydroxy-3-methylbutyl, 2-hydroxy-2-methylpropyl or 2-cyano-2-methylpropyl.

For each of the embodiments described in the paragraph immediately following Formulas $Iv^{1-20}$, t is preferably 2; $R^2$ is phenyl or fluorophenyl; and $R^3$ is 2-hydroxy-2-methylpropyl or 2-cyano-2-methylpropyl.

For each of the embodiments described in the paragraph immediately following Formulas $IV^{1-20}$, t is preferably 2; $R^2$ is phenyl or fluorophenyl; $R^3$ is 2-hydroxy-2-methylpropyl or 2-cyano-2-methylpropyl; one or two ring carbon atoms in the pyridine, pyridazine, pyrimidine, pyrazine, pyrazole, thiazole and thiadiazole rings in Formulas $Iv^{1-20}$ are optionally substituted with fluoro, chloro, cyano, $CONH_2$, CONHMe, $CONMe_2$, CONHc-Pr, methyl, ethyl or $CF_3$; the substitutable ring nitrogen atom in the pyrazole rings in Formulas $Iv^{18-20}$ is optionally substituted with $(C_1-C_4)$alkyl, $(C_3-C_4)$cycloalkyl, $(C_3-C_4)$cycloalkyl$(C_1-C_2)$alkyl, and $(C_1-C_2)$haloalkyl; the ring nitrogen in the pyridine rings in Formulas $IV^{1-4}$ is optionally substituted by oxo.

Another embodiment of the invention is a compound of any one of Formulas $Iw^{1-20}$ or a pharmaceutically acceptable salt thereof:

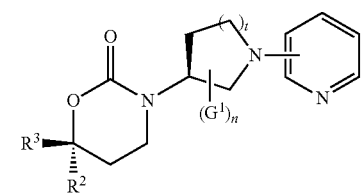

$Iw^1$

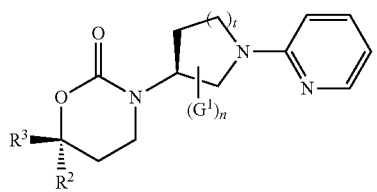

$Iw^2$

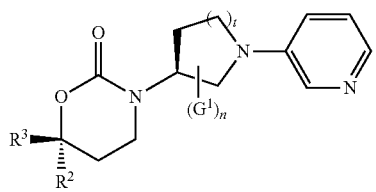

$Iw^3$

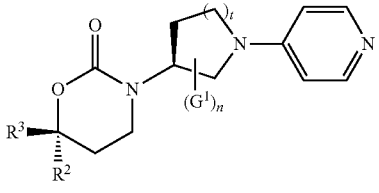

$Iw^4$

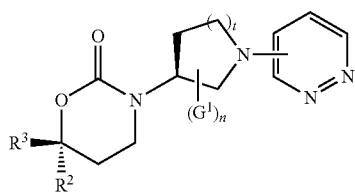

$Iw^5$

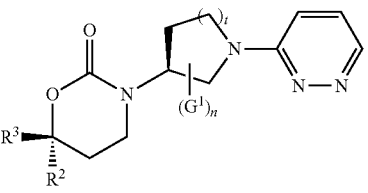

$Iw^6$

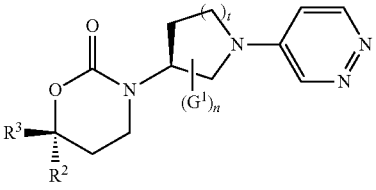

$Iw^7$

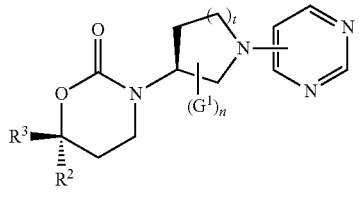

$Iw^8$

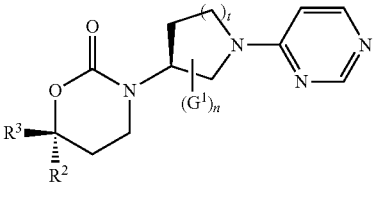

$Iw^9$

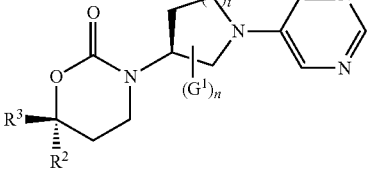

$Iw^{10}$

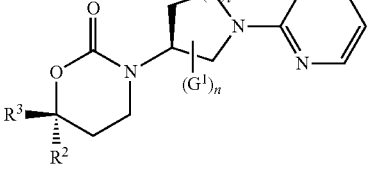

$Iw^{11}$

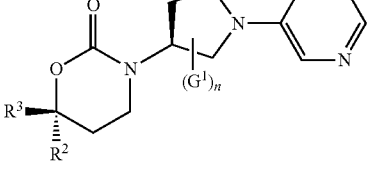

$Iw^{12}$

-continued

Iw[13]

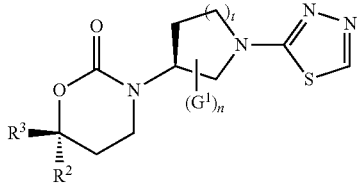

Iw[14]

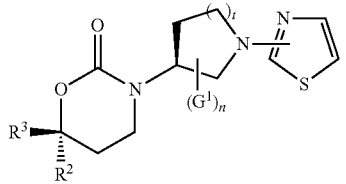

Iw[15]

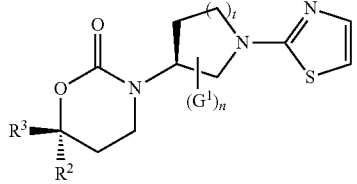

Iw[16]

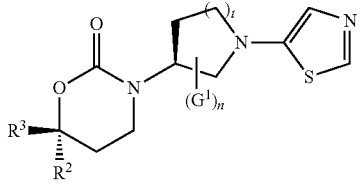

Iw[17]

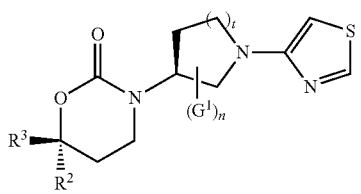

Iw[18]

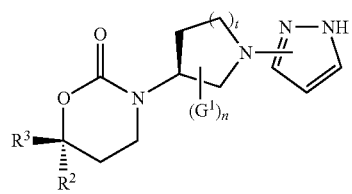

Iw[19]

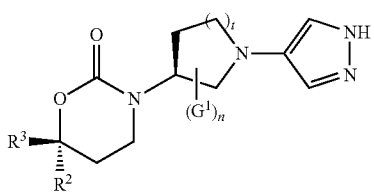

-continued

Iw[20]

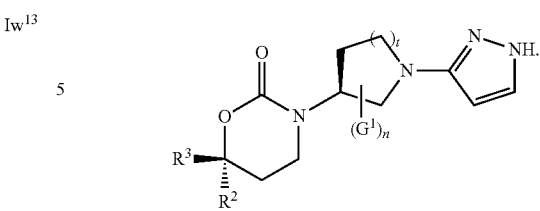

In Formulas Iw[1-20], the pyridine, pyridazine, pyrimidine, pyrazine, pyrazole, thiazole and thiadiazole rings are optionally substituted (substitution at ring carbons bonded to hydrogen and ring nitrogen atoms bonded to hydrogen atoms are encompassed, i.e., a "substitutable ring nitrogen atom") with up to four substituents as described for $Cy^2$ in the first embodiment. Suitable substituents for $Cy^2$ and suitable values for $R^2$ and $R^3$ are as defined above in the first embodiment; suitable values for $G^1$ are independently fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclylsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, $(C_3-C_6)$cycloalkylcarbonyl, $(C_3-C_6)$cycloalkylaminocarbonyl, {$(C_3-C_6)$cycloalkyl}{$(C_1-C_6)$alkyl}aminocarbonyl, di$(C_3-C_6)$cycloalkylaminocarbonyl, $(C_3-C_6)$cycloalkylaminosulfonyl, {$(C_3-C_6)$cycloalkyl}{$(C_1-C_6)$alkyl}aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, {$(C_3-C_6)$cycloalkyl}{$(C_1-C_6)$alkyl}aminocarbonyl$(C_1-C_6)$alkyl and di$(C_3-C_6)$cycloalkylaminocarbonyl$(C_1-C_6)$alkyl; n is 0, 1 or 2; and t is 1, 2 or 3. Alternatively, suitable values for $G^1$ are independently fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkylalkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2$NCO, $H_2$N$SO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclylsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy and ($C_1$-$C_6$)alkylcarbonyl; substituents for the pyridine, pyridazine, pyrimidine, pyrazine, pyrazole, thiazole and thiadiazole rings in Formulas Iw$^{1-20}$ are independently fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkylalkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cyclo-alkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2$NCO, $H_2$N$SO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclylsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy, and ($C_1$-$C_6$)alkylcarbonyl; n is 0, 1 or 2; t is 1, 2 or 3; and values for $R^2$ and $R^3$ are as defined above in the first embodiment. Alternatively, suitable values for $G^1$ include oxo, ($C_1$-$C_4$)alkyl, ($C_1$-$C_4$)alkoxy, ($C_1$-$C_4$)haloalkyl, ($C_1$-$C_4$)haloalkoxy, halogen, cyano and nitro; suitable substituents for a substitutable ring nitrogen atom in the pyrazole rings in Formulas Iw$^{18-20}$ include ($C_1$-$C_4$)alkyl, ($C_3$-$C_4$)cycloalkyl, ($C_3$-$C_4$)cycloalkyl($C_1$-$C_2$)alkyl, and ($C_1$-$C_4$)haloalkyl; suitable substituents for a ring carbon atom in the pyridine, pyridazine, pyrimidine, pyrazine, pyrazole, thiazole and thiadiazole rings in Formulas Iw$^{1-20}$ include fluorine, chlorine, cyano, hydroxy, amino, ($C_1$-$C_4$)alkyl, ($C_3$-$C_4$)cycloalkyl, ($C_3$-$C_4$)cycloalkyl($C_1$-$C_2$)alkyl, halo($C_1$-$C_4$)alkyl, ($C_1$-$C_4$)alkoxy, ($C_1$-$C_4$)haloalkoxy, $CONH_2$, ($C_1$-$C_4$)alkylaminocarbonyl, di($C_1$-$C_4$)alkylaminocarbonyl, ($C_3$-$C_4$)cycloalkylaminocarbonyl, {($C_1$-$C_4$)alkyl}{($C_3$-$C_4$)cycloalkyl}aminocarbonyl and ($C_1$-$C_4$)alkylcarbonylamino; the ring nitrogen in the pyridine rings in Formulas Iw$^{1-4}$ is optionally substituted by oxo; n is 0, 1 or 2; t is 1, 2 or 3; and suitable values for $R^2$ and $R^3$ are as defined above in the first embodiment.

Alternatively, for each of the embodiments described in the paragraph immediately following Formulas Iw$^{1-20}$, $R^3$ is preferably MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

Alternatively, for each of the embodiments described in the paragraph immediately following Formulas Iw$^{1-20}$, $R^3$ is preferably H$_2$NC(=O)CMe$_2$CH$_2$, 3-hydroxy-3-methylbutyl, 2-hydroxy-2-methylpropyl or 2-cyano-2-methylpropyl.

Alternatively, for each of the embodiments described in the paragraph immediately following Formulas Iw$^{1-20}$, $R^2$ is preferably phenyl optionally substituted with 1, 2 or 3 substituents selected from halo, cyano, CONH$_2$, ($C_1$-$C_4$)alkyl, ($C_1$-$C_4$)haloalkyl and SO$_2$Me; and $R^3$ is preferably MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

Alternatively, for each of the embodiments described in the paragraph immediately following Formulas Iw$^{1-20}$, $R^2$ is preferably phenyl optionally substituted with 1, 2 or 3 substituents selected from halo, cyano, CONH$_2$, ($C_1$-$C_4$)alkyl, ($C_1$-$C_4$)haloalkyl and SO$_2$Me; and $R^3$ is preferably H$_2$NC(=O)CMe$_2$CH$_2$, 3-hydroxy-3-methylbutyl, 2-hydroxy-2-methylpropyl or 2-cyano-2-methylpropyl.

Alternatively, for each of the embodiments described in the paragraph immediately following Formulas Iw$^{1-20}$, t is preferably 2; $R^2$ is preferably phenyl or fluorophenyl; and $R^3$ is preferably 2-hydroxy-2-methylpropyl or 2-cyano-2-methylpropyl.

Alternatively, for each of the embodiments described in the paragraph immediately following Formulas Iw$^{1-20}$ or a pharmaceutically acceptable salt thereof: wherein t is 2; $R^2$ is phenyl or fluorophenyl; $R^3$ is 2-hydroxy-2-methylpropyl or 2-cyano-2-methylpropyl; one or two ring carbon atoms in the pyridine, pyridazine, pyrimidine, pyrazine, pyrazole, thiazole and thiadiazole rings in Formulas Iw$^{1-20}$ are optionally substituted with fluoro, chloro, cyano, CONH$_2$, CONHMe, CONMe$_2$, CONHc-Pr, methyl, ethyl or CF$_3$; the substitutable ring nitrogen atom in the pyrazole rings in Formulas Iw$^{18-20}$ is optionally substituted with ($C_1$-$C_4$)alkyl, ($C_3$-$C_4$)cycloalkyl, ($C_3$-$C_4$)cycloalkyl($C_1$-$C_2$)alkyl, and ($C_1$-$C_2$)haloalkyl; the ring nitrogen in the pyridine rings in Formulas Iw$^{14}$ is optionally substituted by oxo.

Another embodiment of the invention (referred to herein as the "First Alternate Embodiment") is a compound represented by Structural Formulas Iw$^{1-20}$, wherein: n is 0 or 1, preferably 0; each $G^1$ is independently ($C_1$-$C_4$)alkyl, ($C_1$-$C_4$)

alkoxy, (C$_1$-C$_4$)haloalkyl, (C$_1$-C$_4$)haloalkoxy, halogen, cyano or nitro; the pyrazole ring is substituted at its substitutable ring nitrogen atom with hydroxy(C$_1$-C$_6$)alkyl, (C$_1$-C$_6$)alkylcarbonylamino(C$_1$-C$_6$)alkyl, (C$_1$-C$_6$)alkylsulfonylamino(C$_1$-C$_6$)alkyl, (C$_1$-C$_6$)alkoxy(C$_1$-C$_6$)alkyl, amino(C$_1$-C$_6$)alkyl, (C$_1$-C$_6$)alkylamino(C$_1$-C$_6$)alkyl, di(C$_1$-C$_6$)alkylamino(C$_1$-C$_6$)alkyl, cyano(C$_1$-C$_6$)alkyl, aminocarbonyl(C$_1$-C$_6$)alkyl, (C$_1$-C$_6$)alkylaminocarbonyl(C$_1$-C$_6$)alkyl, di(C$_1$-C$_6$)alkylaminocarbonyl(C$_1$-C$_6$)alkyl, (C$_3$-C$_6$)cycloalkylaminocarbonyl(C$_1$-C$_6$)alkyl, {(C$_3$-C$_6$)cycloalkyl}{(C$_1$-C$_6$)alkyl}aminocarbonyl(C$_1$-C$_6$)alkyl or di(C$_3$-C$_6$)cycloalkylaminocarbonyl(C$_1$-C$_6$)alkyl; the pyridine, pyridazine, pyrimidine, pyrazine, pyrazole, thiazole and thiadiazole rings are optionally substituted at one or more substitutable ring carbon atoms with a group independently selected from fluorine, chlorine, cyano, hydroxy, amino, (C$_1$-C$_4$)alkyl, (C$_3$-C$_4$)cycloalkyl, (C$_3$-C$_4$)cycloalkyl(C$_1$-C$_2$)alkyl, halo(C$_1$-C$_4$)alkyl, (C$_1$-C$_4$)alkoxy, (C$_1$-C$_4$)haloalkoxy, CONH$_2$, (C$_1$-C$_4$)alkylaminocarbonyl, di(C$_1$-C$_4$)alkylaminocarbonyl and (C$_1$-C$_4$)alkylcarbonylamino; R$^1$ is methyl or ethyl; R$^2$ is phenyl, thienyl, pyridyl or isopropyl each optionally substituted with up to three groups independently selected from halo, methyl, methylthio or (4-morpholino) methyl; and R$^3$ is methyl, ethyl, propyl, butyl, vinyl, allyl or ethoxyethyl each optionally substituted with up to two groups independently selected from methyl, HO—, MeO—, H$_2$N—, MeC(=O)NH—, MeS(=O)$_2$NH—, H$_2$NC(=O)—, MeNHC(=O)—, HO$_2$C—, (HO)$_2$P(=O)O—, H$_2$NS(=O)$_2$O—, H$_2$NS(=O)$_2$NH—, MeNHC(=O)NH—, MeNHC(=O)O—, oxo, cyano, HO$_2$C—, HOCH$_2$CH$_2$NH—, 4-morpholino, HOCH$_2$C(=O)NH—, H$_2$NCH$_2$C(=O)NH—, EtNHC(=O)NH, MeOC(=O)NH—, MeNHC(=NC≡N)NH—, Me-, MeS—, MeSO$_2$-MeSO$_2$N(Me)-, MeS(=O)$_2$NHC(=O)—, imidazolylamino-, imidazolyl, tetrazolyl, H$_2$NCONH—, H$_2$NCO$_2$—, HOCH$_2$CH$_2$O—, MeNH—, Me$_2$N— and MeCONMe.

Alternatively for Structural Formulas Iw$^{1-20}$, R$^2$ is phenyl optionally substituted with 1, 2 or 3 substituents independently selected from halo, cyano, CONH$_2$, (C$_1$-C$_4$)alkyl, (C$_1$-C$_4$)haloalkyl and SO$_2$Me; and R$^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl; and the remainder of the variables are as described above for the First Alternate Embodiment.

Alternatively for Structural Formulas Iw$^{1-20}$, R$^3$ is H$_2$NC(=O)CMe$_2$CH$_2$, 3-hydroxy-3-methylbutyl, 2-hydroxy-2-methylpropyl or 2-cyano-2-methylpropyl; and the remainder of the variables are as described above for the First Alternate Embodiment.

Alternatively for Structural Formulas Iw$^{1-20}$, R$^2$ is phenyl optionally substituted with 1, 2 or 3 substituents independently selected from halo, cyano, CONH$_2$, (C$_1$-C$_4$)alkyl, (C$_1$-C$_4$)haloalkyl and SO$_2$Me; and R$^3$ is H$_2$NC(=O)CMe$_2$CH$_2$, 3-hydroxy-3-methylbutyl, 2-hydroxy-2-methylpropyl or 2-cyano-2-methylpropyl; and the remainder of the variables are as described in the First Alternate Embodiment.

Alternatively for Structural Formulas Iw$^{1-20}$, R$^3$ is 2-hydroxy-2-methylpropyl or 2-cyano-2-methylpropyl; and the remainder of the variables are as described in the First Alternate Embodiment.

Alternatively for Structural Formulas Iw$^{1-20}$, R$^2$ is phenyl or fluorophenyl; and R$^3$ is 2-hydroxy-2-methylpropyl or 2-cyano-2-methylpropyl; and the remainder of the variables are as described in the First Alternate Embodiment.

Alternatively for Structural Formulas Iw$^{1-20}$, R$^2$ is phenyl or fluorophenyl; R$^3$ is 2-hydroxy-2-methylpropyl or 2-cyano-2-methylpropyl; one or two substitutable ring carbon atoms in the pyridine, pyridazine, pyrimidine, pyrazine, pyrazole, thiazole and thiadiazole rings are optionally substituted with methyl or ethyl; and the remainder of the variables are as described in the First Alternate Embodiment.

For the embodiment described in the previous seven paragraphs, n is 0 and all of the substitutable ring carbons in the pyridine, pyridazine, pyrimidine, pyrazine, pyrazole, thiazole and thiadiazole rings are preferably unsubstituted.

Another embodiment of the invention is a compound represented by any one of Formulas It$^{1-6}$, or a pharmaceutically acceptable salt thereof:

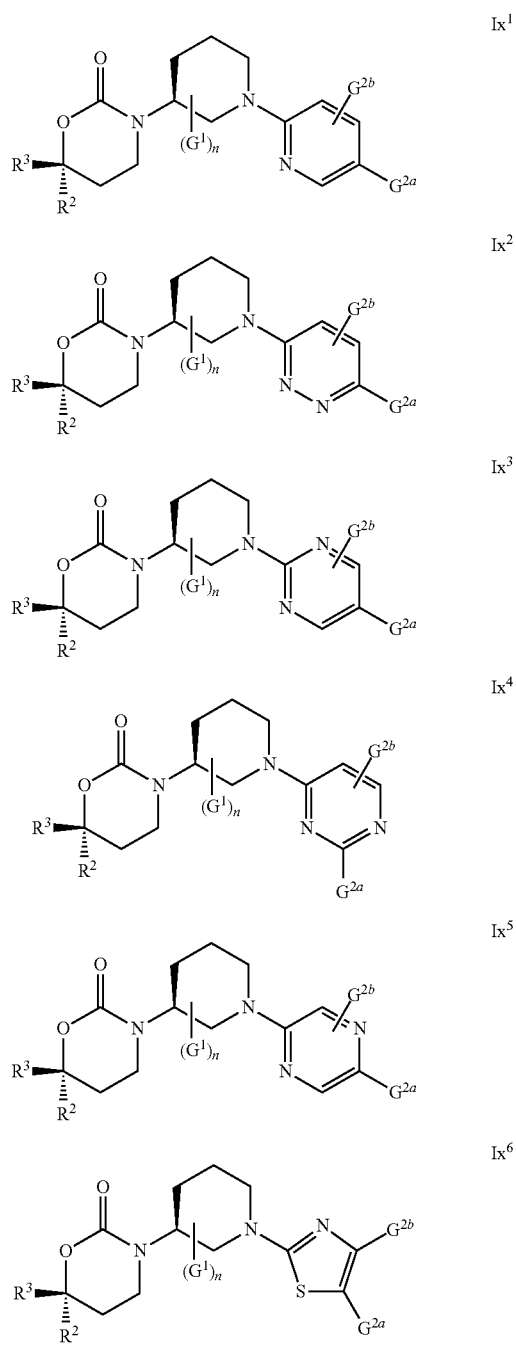

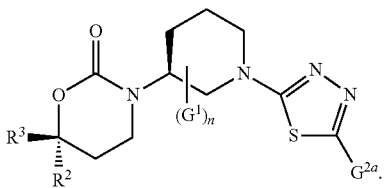

In Formulas Ix$^{1-7}$, G$^1$ is oxo, (C$_1$-C$_4$)alkyl, (C$_1$-C$_4$)alkoxy, (C$_1$-C$_4$)haloalkyl, (C$_1$-C$_4$)haloalkoxy, halogen, cyano and nitro; n is 0, 1 or 2; G$^{2a}$ and G$^{2b}$ are independently selected from hydrogen, fluorine, chlorine, cyano, hydroxy, amino, (C$_1$-C$_4$)alkyl, (C$_3$-C$_4$)cycloalkyl, (C$_3$-C$_4$)cycloalkyl(C$_1$-C$_2$)alkyl, halo(C$_1$-C$_4$)alkyl, (C$_1$-C$_4$)alkoxy, (C$_1$-C$_4$)haloalkoxy, CONH$_2$, (C$_1$-C$_4$)alkylaminocarbonyl, di(C$_1$-C$_4$)alkylaminocarbonyl, (C$_3$-C$_4$)cycloalkylaminocarbonyl, {(C$_1$-C$_4$)alkyl}{(C$_3$-C$_4$)cycloalkyl}aminocarbonyl and (C$_1$-C$_4$)alkylcarbonylamino; and suitable values for R$^2$ and R$^3$ are as defined in the first, second, third, fourth, fifth, sixth, seventh, eighth, ninth, tenth, eleventh or twelfth embodiments.

Alternatively, for each of the embodiments described in the paragraph immediately following Formulas Ix$^{1-7}$, R$^3$ is preferably MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

Alternatively, for each of the embodiments described in the paragraph immediately following Formulas Ix$^{1-7}$, R$^3$ is preferably H$_2$NC(=O)CMe$_2$CH$_2$, 3-hydroxy-3-methylbutyl, 2-hydroxy-2-methylpropyl or 2-cyano-2-methylpropyl.

Alternatively, for each of the embodiments described in the paragraph immediately following Formulas Ix$^{1-7}$, R$^2$ is preferably phenyl optionally substituted with 1, 2 or 3 substituents selected from halo, cyano, CONH$_2$, (C$_1$-C$_4$)alkyl, (C$_1$-C$_4$)haloalkyl and SO$_2$Me; and R$^3$ is preferably MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

Alternatively, for each of the embodiments described in the paragraph immediately following Formulas Ix$^{1-7}$, R$^2$ is preferably phenyl optionally substituted with 1, 2 or 3 substituents selected from halo, cyano, CONH$_2$, (C$_1$-C$_4$)alkyl, (C$_1$-C$_4$)haloalkyl and SO$_2$Me; and R$^3$ is preferably H$_2$NC(=O)CMe$_2$CH$_2$, 3-hydroxy-3-methylbutyl, 2-hydroxy-2-methylpropyl or 2-cyano-2-methylpropyl.

In another alternative for each of the embodiments described in the paragraph immediately following Formulas Ix$^{1-7}$, R$^2$ is preferably phenyl or fluorophenyl; and R$^3$ preferably is 2-hydroxy-2-methylpropyl or 2-cyano-2-methylpropyl.

Another embodiment of the invention (referred to herein as the "Second Alternate Embodiment") is a compound represented by Structural Formulas Ix$^{1-7}$, wherein: n is 0 or 1, preferably 0; each G$^1$ is independently (C$_1$-C$_4$)alkyl, (C$_1$-C$_4$)alkoxy, (C$_1$-C$_4$)haloalkyl, (C$_1$-C$_4$)haloalkoxy, halogen, cyano or nitro; G$^{2a}$ is hydrogen, hydroxy(C$_1$-C$_6$)alkyl, (C$_1$-C$_6$)alkylcarbonylamino(C$_1$-C$_6$)alkyl, (C$_1$-C$_6$)alkylsulfonylamino(C$_1$-C$_6$)alkyl, (C$_1$-C$_6$)alkoxy(C$_1$-C$_6$)alkyl, amino(C$_1$-C$_6$)alkyl, (C$_1$-C$_6$)alkylamino(C$_1$-C$_6$)alkyl, di(C$_1$-C$_6$)alkylamino(C$_1$-C$_6$)alkyl, cyano(C$_1$-C$_6$)alkyl, aminocarbonyl(C$_1$-C$_6$)alkyl, (C$_1$-C$_6$)alkylaminocarbonyl(C$_1$-C$_6$)alkyl, di(C$_1$-C$_6$)alkylaminocarbonyl(C$_1$-C$_6$)alkyl, (C$_3$-C$_6$)cycloalkylaminocarbonyl(C$_1$-C$_6$)alkyl, {(C$_3$-C$_6$)cycloalkyl}{(C$_1$-C$_6$)alkyl}aminocarbonyl(C$_1$-C$_6$)alkyl or di(C$_3$-C$_6$)cycloalkylaminocarbonyl(C$_1$-C$_6$)alkyl; G$^{2b}$ is hydrogen, fluorine, chlorine, cyano, hydroxy, amino, (C$_1$-C$_4$)alkyl, (C$_3$-C$_4$)cycloalkyl, (C$_3$-C$_4$)cycloalkyl(C$_1$-C$_2$)alkyl, halo(C$_1$-C$_4$)alkyl, (C$_1$-C$_4$)alkoxy, (C$_1$-C$_4$)haloalkoxy, CONH$_2$, (C$_1$-C$_4$)alkylaminocarbonyl, di(C$_1$-C$_4$)alkylaminocarbonyl or (C$_1$-C$_4$)alkylcarbonylamino; R$^1$ is methyl or ethyl; R$^2$ is phenyl, thienyl, pyridyl or isopropyl each optionally substituted with up to three groups independently selected from halo, methyl, methylthio or (4-morpholino)methyl; and R$^3$ is methyl, ethyl, propyl, butyl, vinyl, allyl or ethoxyethyl each optionally substituted with up to two groups independently selected from methyl, HO—, MeO—, H$_2$N—, MeC(=O)NH—, MeS(=O)$_2$NH—, H$_2$NC(=O)—, MeNHC(=O)—, HO$_2$C—, (HO)$_2$P(=O)O—, H$_2$NS(=O)$_2$O—, H$_2$NS(=O)$_2$NH—, MeNHC(=O)NH—, MeNHC(=O)O—, oxo, cyano, HO$_2$C—, HOCH$_2$CH$_2$NH—, 4-morpholino, HOCH$_2$C(=O)NH—, H$_2$NCH$_2$C(=O)NH—, EtNHC(=O)NH, MeOC(=O)NH—, MeNHC(=NC—N)NH—, Me-, MeS—, MeSO$_2$-MeSO$_2$N(Me)-, MeS(=O)$_2$NHC(=O)—, imidazolylamino-, imidazolyl, tetrazolyl, H$_2$NCONH—, H$_2$NCO$_2$—, HOCH$_2$CH$_2$O—, MeNH—, Me$_2$N— and MeCONMe.

Alternatively for Structural Formulas Ix$^{1-7}$, R$^2$ is phenyl optionally substituted with 1, 2 or 3 substituents independently selected from halo, cyano, CONH$_2$, (C$_1$-C$_4$)alkyl, (C$_1$-C$_4$)haloalkyl and SO$_2$Me; and R$^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl; and the remainder of the variables are as described above for the Second Alternate Embodiment.

Alternatively for Structural Formulas Ix$^{1-7}$, R$^3$ is H$_2$NC(=O)CMe$_2$CH$_2$, 3-hydroxy-3-methylbutyl, 2-hydroxy-2-methylpropyl or 2-cyano-2-methylpropyl; and the remainder of the variables are as described above for the Second Alternate Embodiment.

Alternatively for Structural Formulas Ix$^{1-7}$, R$^2$ is phenyl optionally substituted with 1, 2 or 3 substituents independently selected from halo, cyano, CONH$_2$, (C$_1$-C$_4$)alkyl, (C$_1$-C$_4$)haloalkyl and SO$_2$Me; and R$^3$ is H$_2$NC(=O)CMe$_2$CH$_2$, 3-hydroxy-3-methylbutyl, 2-hydroxy-2-methylpropyl or 2-cyano-2-methylpropyl; and the remainder of the variables are as described in the Second Alternate Embodiment.

Alternatively for Structural Formulas Ix$^{1-7}$, R$^3$ is 2-hydroxy-2-methylpropyl or 2-cyano-2-methylpropyl; and the remainder of the variables are as described in the Second Alternate Embodiment.

Alternatively for Structural Formulas Ix$^{1-7}$, R$^2$ is phenyl or fluorophenyl; and R$^3$ is 2-hydroxy-2-methylpropyl or 2-cyano-2-methylpropyl; and the remainder of the variables are as described in the Second Alternate Embodiment.

Alternatively for Structural Formulas Ix$^{1-7}$, R$^2$ is phenyl or fluorophenyl; R$^3$ is 2-hydroxy-2-methylpropyl or 2-cyano-2-methylpropyl; one or two substitutable ring carbon atoms in the pyridyl, pyridazinyl, pyrimidinyl, pyrazinyl, thiadiazolyl and thiazolyl rings are optionally substituted with methyl or ethyl; and the remainder of the variables are as described in the Second Alternate Embodiment.

For the embodiment described in the previous seven paragraphs, n is 0 and G$^{2b}$ is preferably —H.

Compounds of the invention are also disclosed in Cyclic Inhibitors Of 11β-Hydroxysteroid Dehydrogenase 1, U.S. Provisional Application No. 61/137,148, filed Jul. 25, 2008; and Cyclic Inhibitors Of 11β-Hydroxysteroid Dehydrogenase 1, International Application No. PCT/US2008/009017, filed Jul. 25, 2008; the entire teachings of these applications are incorporated herein by reference in their entirety.

Definitions

The term "alkyl" means a straight or branched hydrocarbon radical having 1-10 carbon atoms and includes, for example, methyl, ethyl, n-propyl, isopropyl, n-butyl, sec-butyl, isobutyl, tert-butyl, n-pentyl, n-hexyl, n-heptyl, n-octyl, n-nonyl, n-decyl and the like.

The term "cycloalkyl" means a monocyclic, bicyclic or tricyclic, saturated hydrocarbon ring having 3-10 carbon atoms and includes, for example, cyclopropyl (c-Pr), cyclobutyl, cyclopentyl, cyclohexyl, cycloheptyl, cyclooctyl, bicyclo[2.2.2]octyl, bicyclo[2.2.1]heptyl, spiro[4.4]nonane, adamantyl and the like.

The term "aryl" means an aromatic radical which is a phenyl group, a naphthyl group, an indanyl group or a tetrahydronaphthalene group. An aryl group is optionally substituted with 1-4 substituents. Exemplary substituents include alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido.

The term "heteroaryl" means a 5- and 6-membered heteroaromatic radical which may optionally be fused to a saturated or unsaturated ring containing 0-4 heteroatoms selected from N, O, and S and includes, for example, a heteroaromatic radical which is 2- or 3-thienyl, 2- or 3-furanyl, 2- or 3-pyrrolyl, 2-,3-, or 4-pyridyl, 2-pyrazinyl, 2-, 4-, or 5-pyrimidinyl, 3- or 4-pyridazinyl, 1H-indol-6-yl, 1H-indol-5-yl, 1H-benzimidazol-6-yl, 1H-benzimidazol-5-yl, 2-, 4-, 5-, 6-, 7- or 8-quinazolinyl, 2-, 3-, 5-, 6-, 7- or 8-quinoxalinyl, 2-, 3-, 4-, 5-, 6-, 7- or 8-quinolinyl, 1-, 3-, 4-, 5-, 6-, 7- or 8-isoquinolinyl, 2-, 4-, or 5-thiazolyl, 2-, 3-, 4-, or 5-pyrazolyl, 2-, 3-, 4-, or 5-imidazolyl. A heteroaryl is optionally substituted. Exemplary substituents include alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido, or by oxo to form an N-oxide.

The term "heterocyclyl" means a 4-, 5-, 6- and 7-membered saturated or partially unsaturated heterocyclic ring containing 1 to 4 heteroatoms independently selected from N, O, and S. Exemplary heterocyclyls include pyrrolidine, pyrrolidin-2-one, 1-methylpyrrolidin-2-one, piperidine, piperidin-2-one, dihydropyridine, tetrahydropyridine, piperazine, 1-(2, 2,2-trifluoroethyl)piperazine, 1,2-dihydro-2-oxopyridine, 1,4-dihydro-4-oxopyridine, piperazin-2-one, 3,4,5,6-tetrahydro-4-oxopyrimidine, 3,4-dihydro-4-oxopyrimidine, tetrahydrofuran, tetrahydropyran, tetrahydrothiophene, tetrahydrothiopyran, isoxazolidine, 1,3-dioxolane, 1,3-dithiolane, 1,3-dioxane, 1,4-dioxane, 1,3-dithiane, 1,4-dithiane, oxazolidin-2-one, imidazolidin-2-one, imidazolidine-2,4-dione, tetrahydropyrimidin-2(1H)-one, morpholine, N-methylmorpholine, morpholin-3-one, 1,3-oxazinan-2-one, thiomorpholine, thiomorpholine 1,1-dioxide, tetrahydro-1,2,5-thiaoxazole 1,1-dioxide, tetrahydro-2H-1,2-thiazine 1,1-dioxide, hexahydro-1,2,6-thiadiazine 1,1-dioxide, tetrahydro-1,2,5-thiadiazole 1,1-dioxide isothiazolidine 1,1-dioxide, 6-oxo-1, 6-dihydropyridazin-3-yl, 6-oxo-1,6-dihydropyridazin-4-yl, 5-oxo-4,5-dihydro-1H-1,2,4-triazol-3-yl and 5-oxo-4,5-dihydro-1H-imidazol-2-yl. A heterocyclyl can be optionally substituted with 1-4 substituents. Exemplary substituents include lkyl, haloalkyl, halogen and oxo.

The term "spirocycloalkyl" means a cycloalkyl group which shares one ring carbon with another alkyl or cycloalkyl group.

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject is a human in need of treatment.

When a disclosed compound or its pharmaceutically acceptable salt is named or depicted by structure, it is to be understood that solvates or hydrates of the compound or its pharmaceutically acceptable salts are also included. "Solvates" refer to crystalline forms wherein solvent molecules are incorporated into the crystal lattice during crystallization. Solvate may include water or nonaqueous solvents such as ethanol, isopropanol, DMSO, acetic acid, ethanolamine, and EtOAc. Solvates, wherein water is the solvent molecule incorporated into the crystal lattice, are typically referred to as "hydrates." Hydrates include stoichiometric hydrates as well as compositions containing variable amounts of water. Some of the compounds disclosed in the exemplification may be in the anhydrous form.

The term "compound" also includes labeling at one or more positions with deuterium. "Labeled with deuterium at a position" means that the amount deuterium at the position is greater than the amount that is present at natural abundance. In certain instances, the deuterium at each position in a "compound" is at natural abundance.

Certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms. The symbol "*" in a structural formula represents the presence of a chiral carbon center. "R" and "S" represent the configuration of substituents around one or more chiral carbon atoms. Thus, "R*" and "S*" denote the relative configurations of substituents around one or more chiral carbon atoms. "Racemate" or "racemic mixture" means a compound of equimolar quantities of two enantiomers, wherein such mixtures exhibit no optical activity; i.e., they do not rotate the plane of polarized light.

"Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration.

"R," "S," "S*," "R*," "E," "Z," "cis," and "trans," indicate configurations relative to the core molecule.

The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods.

When the stereochemistry of a disclosed compound is named or depicted by structure, the named or depicted stereoisomer is at least 60%, 70%, 80%, 90%, 99% or 99.9% by weight pure relative to the other stereoisomers. When a single enantiomer is named or depicted by structure, the depicted or named enantiomer is at least 60%, 70%, 80%, 90%, 99% or 99.9% by weight optically pure. Percent optical purity by weight is the ratio of the weight of the enantiomer over the weight of the enantiomer plus the weight of its optical isomer.

When a disclosed compound is named or depicted by structure without indicating the stereochemistry, and the compound has at least one chiral center, it is to be understood that the name or structure encompasses one enantiomer of compound free from the corresponding optical isomer, a racemic mixture of the compound and mixtures enriched in one enantiomer relative to its corresponding optical isomer.

When a disclosed compound is named or depicted by structure without indicating the stereochemistry and has at least two chiral centers, it is to be understood that the name or structure encompasses a diastereomer free of other diastereomers, a pair of diastereomers free from other diastereomeric pairs, mixtures of diastereomers, mixtures of diastereomeric pairs, mixtures of diastereomers in which one diastereomer is enriched relative to the other diastereomer(s) and mixtures of diastereomeric pairs in which one diastereomeric pair is enriched relative to the other diastereomeric pair(s).

The compounds of the invention may be present in the form of pharmaceutically acceptable salts. For use in medicines, the salts of the compounds of the invention refer to non-toxic "pharmaceutically acceptable salts." Pharmaceutically acceptable salt forms include pharmaceutically acceptable acidic/anionic or basic/cationic salts.

Pharmaceutically acceptable basic/cationic salts include, the sodium, potassium, calcium, magnesium, diethanolamine, n-methyl-D-glucamine, L-lysine, L-arginine, ammonium, ethanolamine, piperazine and triethanolamine salts.

Pharmaceutically acceptable acidic/anionic salts include, the acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrobromide, hydrochloride, hydroxynaphthoate, iodide, isethionate, lactate, lactobionate, malate, maleate, malonate, mandelate, mesylate, methylsulfate, mucate, napsylate, nitrate, pamoate, pantothenate, phosphate/diphospate, polygalacturonate, salicylate, stearate, subacetate, succinate, sulfate, hydrogensulfate, tannate, tartrate, teoclate, tosylate, and triethiodide salts.

The following abbreviations have the indicated meanings:

| Abbreviation | Meaning |
| --- | --- |
| A% | Area percentage |
| Boc | tert-butoxy carbonyl or t-butoxy carbonyl |
| (Boc)$_2$O | di-tert-butyl dicarbonate |
| Cbz | Benzyloxycarbonyl |
| CbzCl | Benzyl chloroformate |
| c-Pr | cyclopropyl |
| DAST | diethylaminosulfur trifluoride |
| DBU | 1,8-diazabicyclo+5.4.0+undec-7-ene |
| DCC | N,N'-dicyclohexylcarbodiimide |
| DCU | N,N'-dicyclohexylurea |
| DIAD | diisopropyl azodicarboxylate |
| DIBAL-H | diisobutylaluminum hydride |
| DIEA | N,N-diisopropylethylamine |
| DMAP | 4-(dimethylamino)pyridine |
| DMF | N,N-dimethylformamide |
| DMPU | 1,3-dimethyl-3,4,5,6-tetrahydro-2(1H)-pyrimidinone |
| 2,4-DNP | 2,4-dinitrophenyihydrazine |
| DPTBS | Diphenyl-t-butylsilyl |
| dr | diastereomer ratio |
| EDC.HCl, EDCI | 1-[3-(dimethylamino)propyl]-3-ethylcarbodiimide hydrochloride |
| Equiv | equivalents |
| EtOAc | Ethyl acetate |
| Fmoc | 1-[[(9H-fluoren-9-ylmethoxy)carbonyl]oxy]- |
| Fmoc-OSu | 1-[[(9H-fluoren-9-ylmethoxy)carbonyl]oxy]-2,5-pyrrolidinedione |
| h, hr | hour(s) |
| HOBt | 1-hydroxybenzotriazole |
| HATU | 2-(7-Aza-1H-benzotriazole-1-y1)-1,1,3,3-tetramethyluronium hexafluorophosphate |
| HBTU | 2-(1H-Benzotriazol-1-yl)-1,1,3,3-tetramethyluronium hexafluorophosphate |
| KHMDS | potassium hexamethyldisilazane |
| LAH or LiAlH$_4$ | lithium aluminum hydride |
| LC-MS | liquid chromatography-mass spectroscopy |
| LHMDS | lithium hexamethyldisilazane |
| m-CPBA | meta-chloroperoxybenzoic acid |
| Me | methyl |
| MsCl | methanesulfonyl chloride |
| Min | minute |
| MS | mass spectrum |
| NaH | sodium hydride |
| NaHCO$_3$ | sodium bicarbonate |
| NaN$_3$ | sodium azide |
| NaOH | sodium hydroxide |
| Na$_2$SO$_4$ | sodium sulfate |
| NMM | N-methylmorpholine |
| NMP | N-methylpyrrolidinone |
| Pd$_2$(dba)$_3$ | tris(dibenzylideneacetone)dipalladium(0) |
| PE | petroleum ether |
| Quant | quantitative yield |
| rt | room temperature |
| Satd | saturated |
| SOCl$_2$ | thionyl chloride |
| SFC | supercritical fluid chromatography |
| SPA | scintillation proximity assay |
| SPE | solid phase extraction |
| TBAF | tetrabutylammonium fluoride |
| TBS | t-butyldimethylsilyl |
| TBDPS | t-butyldiphenylsilyl |
| TBSCl | t-butyldimethylsilyl chloride |
| TBDPSCl | t-butyldiphenylsilyl chloride |
| TEA | triethylamine or Et$_3$N |
| TEMPO | 2,2,6,6-tetramethyl-1-piperidinyloxy free radical |
| Teoc | 1-[2-(trimethylsilyl)ethoxycarbonyloxy]- |
| Teoc-OSu | 1-[2-(trimethylsilyl)ethoxycarbonyloxy]pyrrolidin-2,5-dione |
| $T_{ext}$ | External temperature |
| $T_{int}$ | Internal temperature |
| TFA | trifluoroacetic acid |
| Tlc, TLC | thin layer chromatography |
| TMS | trimethylsilyl |
| TMSCl | chlorotrimethylsilane or trimethylsilyl chloride |
| $t_R$ | retention time |
| TsOH | p-toluenesulfonic acid |

General Description of Synthetic Methods

Compounds of Formula I can be prepared by several processes. In the discussion below, E, $R^2$, $R^3$, and t have the meanings indicated above unless otherwise noted. $Cy^2$ is an optionally substituted pyridyl, pyridazinyl, pyrimidinyl, pyrazinyl, thiadiazolyl, thiazolyl or pyrazolyl group. In cases where the synthetic intermediates and final products of Formulas I described below contain potentially reactive functional groups, for example amino, hydroxyl, thiol and carboxylic acid groups, that may interfere with the desired reaction, it may be advantageous to employ protected forms of the intermediate. Methods for the selection, introduction and subsequent removal of protecting groups are well known to those skilled in the art. (T. W. Greene and P. G. M. Wuts "Protective Groups in Organic Synthesis" John Wiley & Sons, Inc., New York 1999). Such protecting group manipulations are assumed in the discussion below and not described explicitly. Generally, reagents in the reaction schemes are used in equimolar amounts; however, in certain cases it may be desirable to use an excess of one reagent to drive a reaction to completion. This is especially the case when the excess reagent can be readily removed by evaporation or extraction. Bases employed to neutralize HCl in reaction mixtures are generally used in slight to substantial excess (1.05-5 equivalents).

In a first process a compound of Formula I*, can be prepared by reaction of an aminoalcohol intermediate of Formula II with a reagent of Formula III, wherein $Z^1$ and $Z^2$ are leaving groups such as chloride, 1-imidazolyl or aryloxide in an inert solvent such as THF, $CH_2Cl_2$, toluene or MeCN, usually in the presence of an organic or inorganic base such as triethylamine or $NaHCO_3$ respectively, at −10° C. to 120° C.:

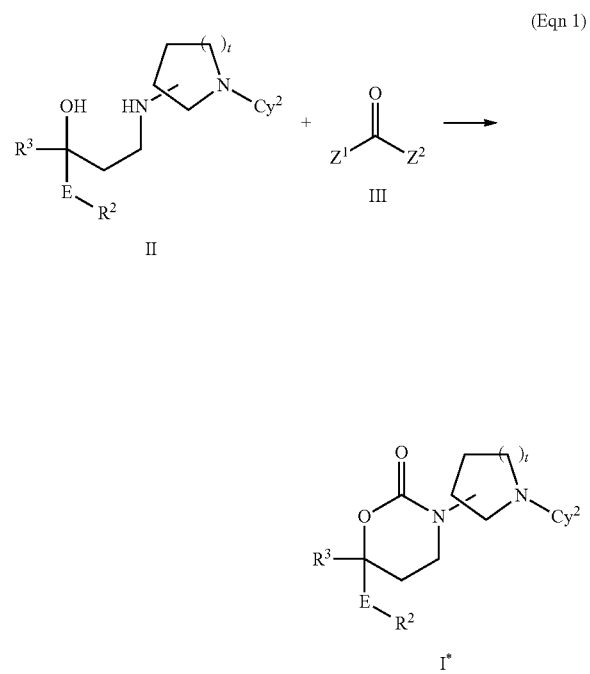

(Eqn 1)

Certain instances of reagent III are especially convenient because they are commercially available. For example when $Z^1$ and $Z^2$ are both chloride, III is phosgene. When $Z^1$ and $Z^2$ are both 1-imidazolyl, III is carbonyl diimidazole. When $Z^1$ is chloride and $Z^2$ is p-nitrophenoxide, III is p-nitrophenyl chloroformate. When $Z^1$ and $Z^2$ are both $OCCl_3$, III is triphosgene and as little as one third of molar equivalent can be used.

Aminoalcohol intermediates of Formula II can be prepared by reduction of amides of Formula IV using a hydride reagent such as $BH_3$.THF solution, $BH_3.Me_2S$ or $LiAlH_4$ in an inert solvent ethereal such as THF or DME at 20° C. to 100° C. for between 1 h and 48 h:

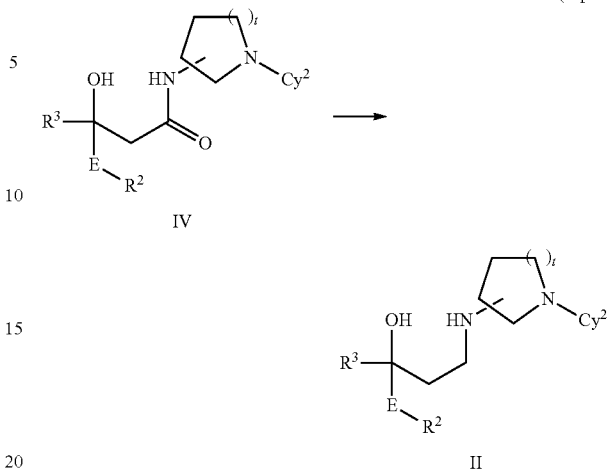

(Eqn 2)

Intermediates of Formula IV can be prepared by coupling a β-hydroxyacid of Formula V with an amine of Formula VI using standard peptide coupling reagents such as EDC in the presence of HOBt and N,N-diisopropylethylamine in an inert solvent such as $CH_2Cl_2$ at 0-30° C. for between 1 h and 24 h:

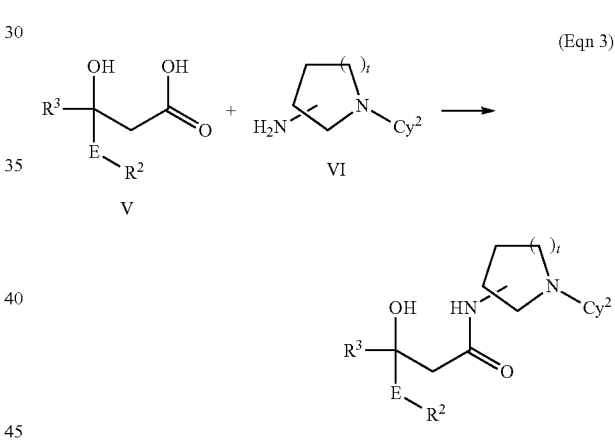

(Eqn 3)

Amine intermediates of Formula VI can be prepared by reduction of amides of Formula VII using a hydride reagent such as $BH_3$.THF solution, $BH_3.Me_2S$ or $LiAlH_4$ in an inert solvent ethereal such as THF or DME at 20° C. to 100° C. for between 1 h and 48 h:

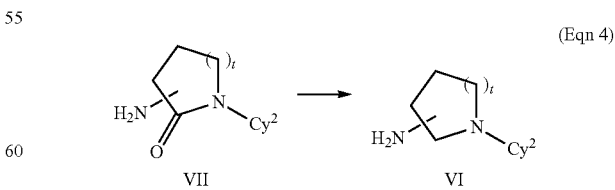

(Eqn 4)

Amine intermediates of Formula VI can be prepared from ketones of formula VIII via oximes of Formula IX or by reductive amination of a ketone of Formula VIII with ammonia:

(Eqn 5)

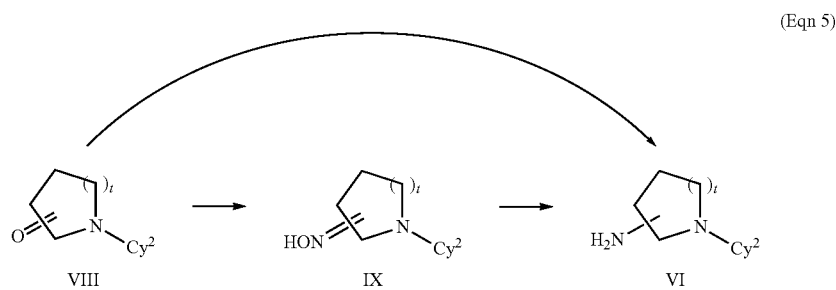

Methods for the conversion of ketones to oximes are described in Smith, M. B. and March, J. "March's Advanced Organic Chemistry" pp 1194-1195, 5$^{th}$ Edition, Wiley, New York, N.Y., 2001. Methods for the reduction of oximes to primary amines are described in Smith, M. B. and March, J. "March's Advanced Organic Chemistry" p 1555, 5th Edition, Wiley, New York, N.Y., 2001. Methods for the reductive amination of ketones are described in Baxter, E. W. and Reitz, A. B. "Organic Reactions" Volume 59, Ed. Overman, L. E., Wiley Interscience, 2002.

Intermediates of Formula II can be prepared by reaction of oxetanes of Formula X with amines of Formula VI as described in Smith, M. B. and March, J. "March's Advanced Organic Chemistry" p 505, 5$^{th}$ Edition, Wiley, New York, N.Y., 2001:

(Eqn 6)

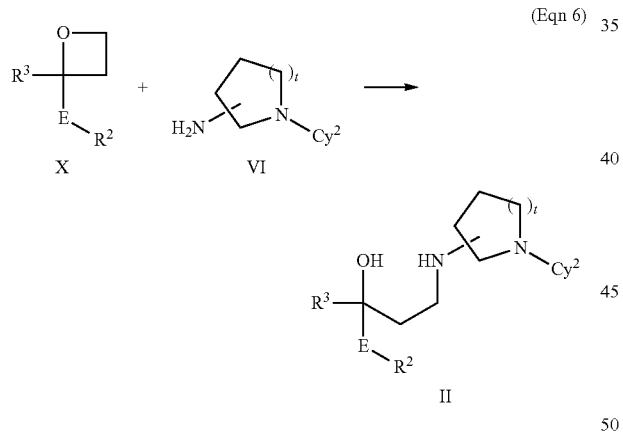

Intermediates of Formula II can also be prepared by reductive amination of β-hydroxyaldehydes of Formula XI with amines of Formula VI. Methods for the reductive amination of aldehydes are described in Baxter, E. W. and Reitz, A. B. "Organic Reactions" Volume 59, Ed. Overman, L. E., Wiley Interscience, 2002.

(Eqn 7)

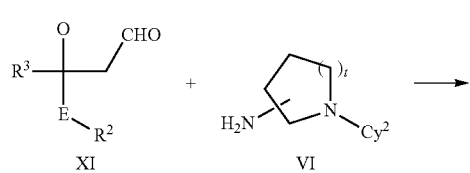

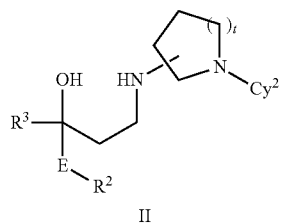

Aldehydes of Formula XI can be prepared from homoallylic alcohols of Formula XXI by treatment with $OsO_4$ and $NaIO_4$.

Aminoalcohol intermediates of Formula II can also be prepared by reaction of aminoalcohols of Formula XII with ketones of Formula VIII in the presence of a reducing agent such as $NaCNBH_3$ or $Na(OAc)_3BH$:

(Eqn 8)

Methods for the reductive amination of aldehydes and ketones are described in Baxter, E. W. and Reitz, A. B. "Organic Reactions" Volume 59, Ed. Overman, L. E., Wiley Interscience, 2002.

Amino-alcohol intermediates of Formula XII can be prepared by treatment of sulfonate intermediates of Formula XVII, wherein $R^4$ is for example methyl, trifluoromethyl or p-methylphenyl, with sodium azide to give an azide intermediate of Formula XVIII, followed by catalytic hydrogenation or by Staudinger reduction with $PPh_3$ in wet THF:

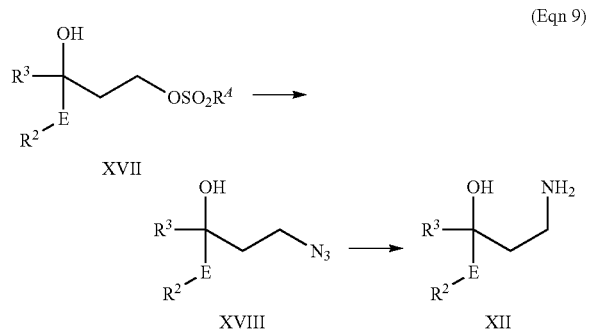
(Eqn 9)

Sulfonate intermediates of Formula XVII can be prepared from diol intermediates of Formula XIX with a sulfonyl chloride $R^A SO_2 Cl$:

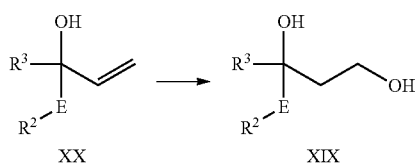
(Eqn 10)

Diol intermediates of Formula XIX can be prepared by hydroboration of allyl alcohols of Formula XX:

(Eqn 11)
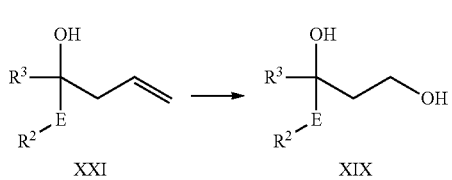

Diol intermediates of Formula XIX can be prepared by ozonolysis and reduction of homoallyl alcohols of Formula XXI:

(Eqn 12)

In a second process a compound of Formula I* can be prepared by reaction of a ketocarbamate of Formula XXIV, wherein $R^D$ is an alkyl or arylalkyl group such as methyl, t-butyl or benzyl, with an organometallic reagent of Formula XXV wherein M includes, but is not limited to, MgCl, MgBr, MgI or Li:

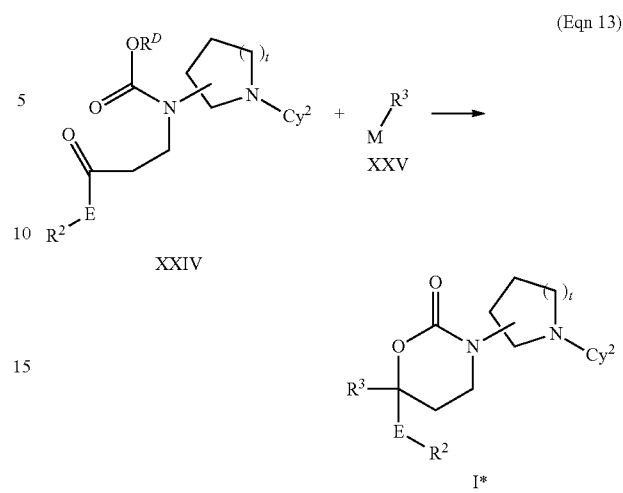
(Eqn 13)

In specific examples, organometallic reagent XXV is allylmagnesium bromide, allylzinc(II) bromide, (2-methylallyl) magnesium chloride or (2-methoxy-2-oxoethyl)zinc(II) bromide. In certain cases when M is MgCl, MgBr or MgI, it is advantageous to add $CeCl_3$ to the reaction mixture.

Ketocarbamates of Formula XXIV can be prepared by reaction of aminoketones of Formula XXVI with intermediates of Formula XXVII wherein $R^E$ is a leaving group such as chloride, succinyloxy, imidazolyl or t-butoxycarboxycarbonyl:

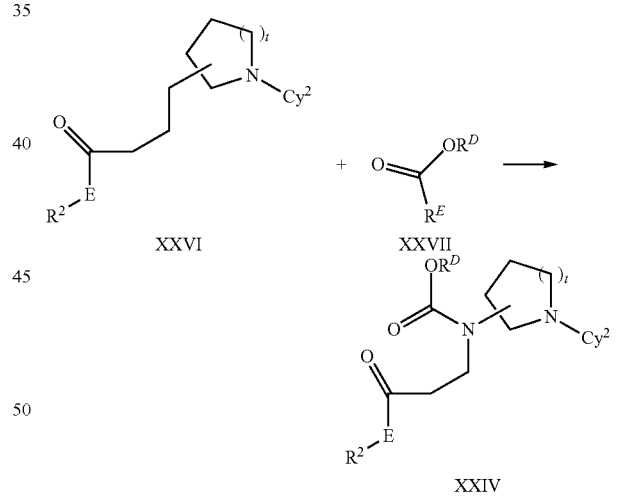
(Eqn 14)

Aminoketones of Formula XXVI can be prepared by reaction of α,β-unsaturated ketones of Formula XXVIII with amines of Formula VI:

(Eqn 15)
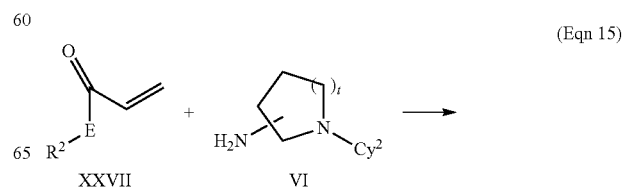

-continued

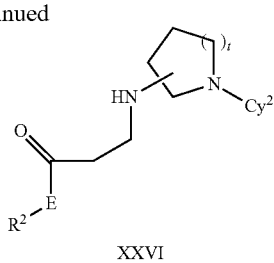
XXVI

Aminoketones of Formula XXVI can be prepared by reaction of β-dialkylaminoketones of Formula XXVIII, wherein $R^F$ is lower alkyl especially methyl, with amines of Formula VI:

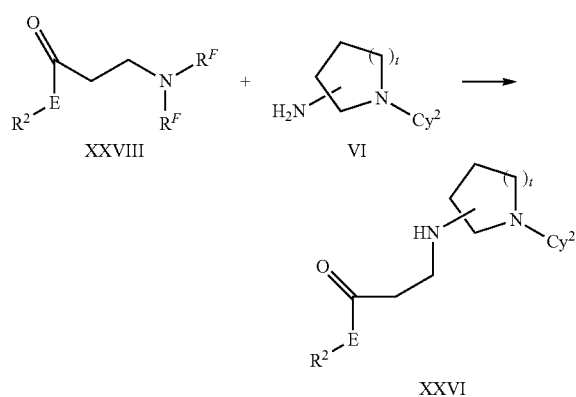

(Eqn 16)

β-Dialkylaminoketones of Formula XXVIII are in turn derived from α, β-unsaturated ketones of Formula XXVII with dialkylamines of Formula $R^F NHR^F$.

In a third process a compound of Formula I* can be prepared by reaction of a compound of Formula XVII with an isocyanate of Formula XXIX in the presence of a base:

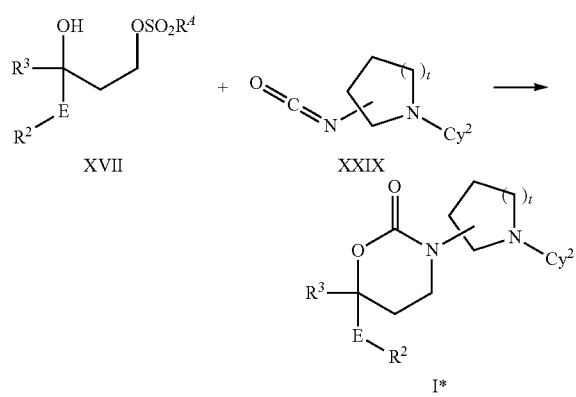

(Eqn 17)

Isocyanates of Formula XXIX can be prepared from amines of Formula VI by treatment with phosgene, diphosgene or triphosgene.

In a fourth process a compound of Formula I* can be prepared by reaction of a halo compound of Formula, wherein Hal is chlorine or bromine, with an isocyanate of Formula XXIX in the presence of a base:

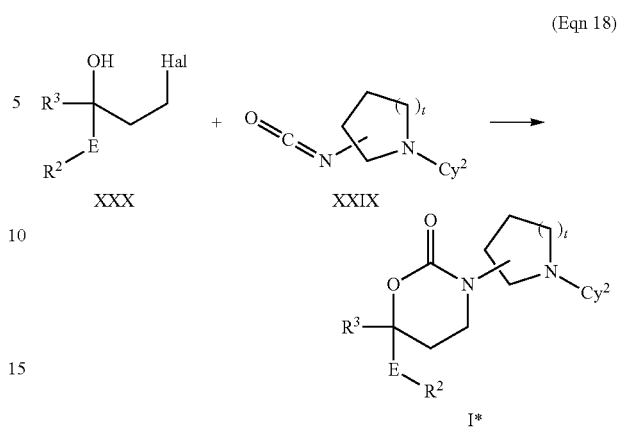

(Eqn 18)

Halo compounds of Formula XXX can be prepared by reaction of β-haloketones of Formula XXXI with organometallic reagents of Formula XXV wherein M is a metal containing radical including MgCl, MgBr, MgI or Li. The reaction is optionally carried out in the presence of anhydrous cerium trichloride:

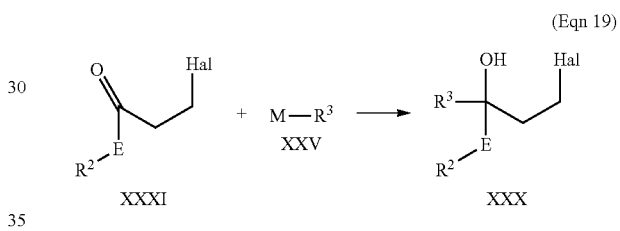

(Eqn 19)

In a fifth process a compound of Formula I* can be prepared by reaction of a cyclic amine of Formula XXXIV with various heterocyclic compounds of Formula XXXV.

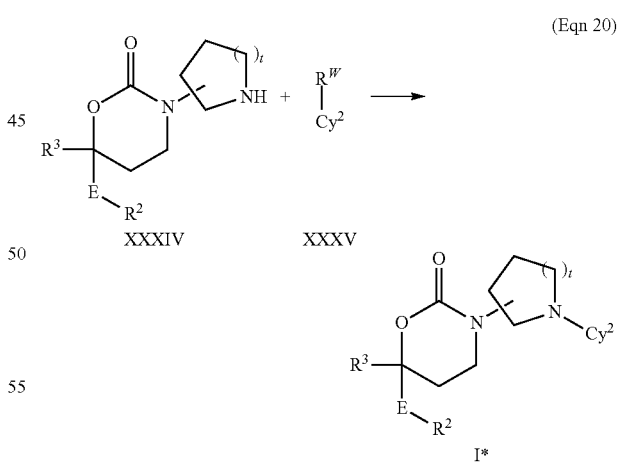

(Eqn 20)

In one modification, $R^W$ is fluoro, chloro, bromo, iodo, $SO_2Me$, $SO_2CF_3$, $OSO_2Me$ or $OSO_2CF_3$ and the reaction is carried out thermally in the presence of a suitable base such as i-$Pr_2NEt$. In a second modification, $R^W$ is iodo or bromo and the reaction is carried out in the presence of a palladium or copper catalyst. In a third modification, $R^W$ is $B(OR^Y)2$, wherein $R^Y$ is hydrogen or ($C_1$-$C_6$)alkyl, or the two groups $R^Y$ taken together form a ($C_1$-$C_{12}$)alkylene group, and the reaction is carried out in the presence of a copper catalyst. Often the second and third modifications can be performed at lower temperature than the first modification.

Cyclic amine compounds of Formula XXXIV can be prepared from protected cyclic amine compounds of Formula XXXIVa, wherein PG is an amine protecting group such t-butoxycarbonyl or benzyloxycarbonyl.

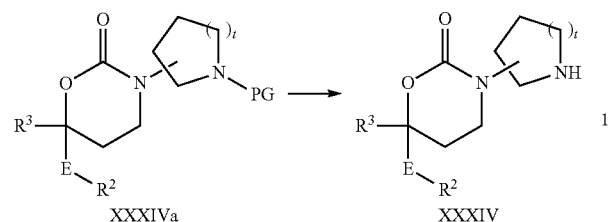
(Eqn 21)

Protected cyclic amines of Formula XXXIVa can be prepared using certain processes analogous to those shown for Compounds of Formula I*. Thus, in the first process, in Eqns 1, 2, 3, 5, 6, and 7, structures of intermediates containing $Cy^2$ are replaced with the analogous structures in which $Cy^2$ is replaced by PG. In the second process, in Eqns 13, 14, 15 and 16, structures of intermediates containing $Cy^2$ are replaced with the analogous structures in which $Cy^2$ is replaced by PG. In the third process, in Eqn 17, structures of intermediates containing $Cy^2$ are replaced with the analogous structures in which $Cy^2$ is replaced by PG. In the fourth process, in Eqn 18, structures of intermediates containing $Cy^2$ are replaced with the analogous structures in which $Cy^2$ is replaced by PG. In the sixth process, in Eqns 23 and 24, structures of intermediates containing $Cy^2$ are replaced with the analogous structures in which $Cy^2$ is replaced by PG.

In a sixth process, a compound of Formula I is prepared from a hydroxycarbamate of Formula XXXVI by treatment with a strong base, such as sodium hydride, in an inert solvent such as THF.

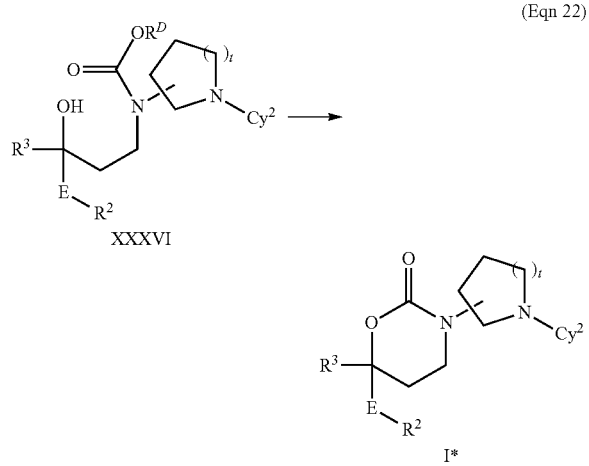
(Eqn 22)

Hydroxycarbamates of Formula XXXVI, wherein $R^D$ is an alkyl or arylalkyl group such as methyl, t-butyl or benzyl, can be prepared by reaction of aminoalcohols of II with intermediates of Formula XXVII wherein $R^D$ is $R^E$ is a leaving group such as chloride, succinyloxy, imidazolyl or t-butoxycarboxycarbonyl:

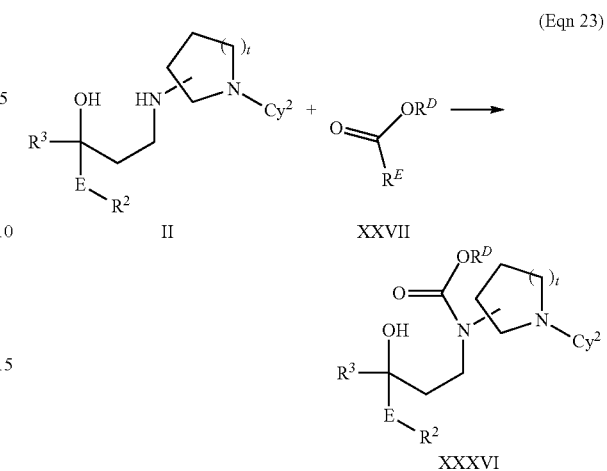
(Eqn 23)

In addition to the methods described above aminoalcohols of Formula II can also be prepared by reaction of chloroalcohols of Formula XXX with amines of Formula VI:

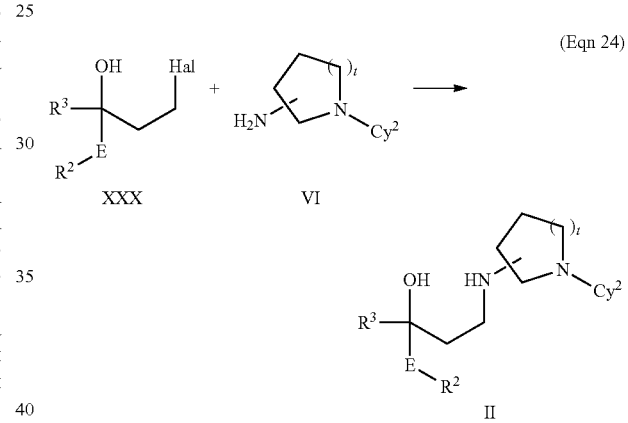
(Eqn 24)

In a seventh process a compound of Formula I* can be prepared from another compound of Formula I*. For example:

(1) a compound of Formula I*, wherein $R^3$ is ω-hydroxy $(C_2-C_6)$alkyl, can be oxidized to a compound of Formula I*, wherein $R^3$ is ω-carboxy$(C_1-C_6)$alkyl, using Jones reagent.

(2) a compound of Formula I*, wherein $R^3$ is ω-carboxy $(C_1-C_6)$alkyl, can be coupled with ammonia or a $(C_1-C_6)$ alkylamine using a standard peptide coupling reagent such as EDC to afford a compound of Formula I*, wherein $R^3$ is ω-$H_2NC(=O)(C_1-C_6)$alkyl or ω-$\{(C_1-C_6)alkylNHC(=O)\}$ $(C_1-C_6)$alkyl.

(3) a compound of Formula I*, wherein $R^3$ is β-hydroxy $(C_1-C_6)$alkyl, can be converted to its methanesulfonate or trifluoromethanesulfonate, treated with sodium azide and reduced to give a compound of Formula I*, wherein $R^3$ is ω-amino$(C_1-C_6)$alkyl.

(4) a compound of Formula I*, wherein $R^3$ is amino$(C_1-C_6)$alkyl, can be reacted with acetic anhydride or acetyl chloride to give a compound of Formula I*, wherein $R^3$ is {acetylamino}$(C_1-C_6)$alkyl.

(5) a compound of Formula I*, wherein $R^3$ is amino$(C_1-C_6)$alkyl, can be reacted with methanesulfonyl chloride to give a compound of Formula I*, wherein $R^3$ is {methanesulfonylamino}$(C_1-C_6)$alkyl.

(6) a compound of Formula I*, wherein $R^3$ is $(C_2\text{-}C_6)$ alkenyl, is hydroborated to afford a compound of Formula I*, wherein $R^3$ is hydroxy$(C_2\text{-}C_6)$alkyl.

(7) a compound of Formula I*, wherein $R^3$ is $(C_2\text{-}C_6)$ alkenyl, can be reacted with osmium tetroxide and N-methylmorpholine-N-oxide to afford a vicinal diol compound of Formula I*, wherein $R^3$ is vicinal dihydroxy$(C_2\text{-}C_6)$alkyl.

(8) a compound of Formula I*, wherein $R^3$ is $(C_2\text{-}C_6)$ alkenyl, can be reacted with ozone followed by $NaBH_4$ to give a compound of Formula I*, wherein $R^3$ is ω-hydroxy$(C_1\text{-}C_6)$ alkyl.

(9) a compound of Formula I*, wherein $R^3$ is amino$(C_1\text{-}C_6)$alkyl, can be reacted with an $(C_1\text{-}C_6)$alkyl isocyanate to give a compound of Formula I*, wherein $R^3$ is $(C_1\text{-}C_6)$alkylaminocarbonylamino$(C_1\text{-}C_6)$alkyl.

(10) a compound of Formula I*, wherein $R^3$ is amino$(C_1\text{-}C_6)$alkyl, can be reacted with an $(C_1\text{-}C_6)$alkyl chloroformate to give a compound of Formula I*, wherein $R^3$ is $(C_1\text{-}C_6)$ alkoxycarbonylamino$(C_1\text{-}C_6)$alkyl.

(11) a compound of Formula I*, wherein $R^3$ is amino$(C_1\text{-}C_6)$alkyl, can be reacted with chlorosulfonyl isocyanate or sulfamide to give a compound of Formula I*, wherein $R^3$ is aminosulfonylamino$(C_1\text{-}C_6)$alkyl.

(12) a compound of Formula I*, wherein $R^3$ is amino$(C_1\text{-}C_6)$alkyl, can be reacted with a $(C_1\text{-}C_6)$alkylsulfamoyl chloride to give a compound of Formula I*, wherein $R^3$ is $(C_1\text{-}C_6)$alkylaminosulfonylamino$(C_1\text{-}C_6)$alkyl.

(13) a compound of Formula I*, wherein $R^3$ is hydroxy$(C_1\text{-}C_6)$alkyl, can be reacted with chlorosulfonyl isocyanate to give a compound of Formula I*, wherein $R^3$ is aminosulfonyloxy$(C_1\text{-}C_6)$alkyl.

(14) a compound of Formula I*, wherein $R^3$ is hydroxy$(C_1\text{-}C_6)$alkyl, can be reacted with p-nitrophenyl chloroformate, pentafluorophenyl chloroformate or carbonyl diimidazole, followed by ammonia, a $(C_1\text{-}C_6)$alkylamine or a di$(C_1\text{-}C_6)$ alkylamine to give a compound of Formula I*, wherein $R^3$ is aminocarboxy$(C_1\text{-}C_6)$alkyl, $(C_1\text{-}C_6)$alkyl aminocarboxy$(C_1\text{-}C_6)$alkyl or di$(C_1\text{-}C_6)$alkyl aminocarboxy$(C_1\text{-}C_6)$alkyl.

(15) a compound of Formula I*, wherein $R^3$ is hydroxy$(C_1\text{-}C_6)$alkyl, can be reacted with $POCl_3$ to give a compound of Formula I*, wherein $R^3$ is $(HO)_2P(\!=\!O)O(C_1\text{-}C_6)$alkyl.

(16) a compound of Formula I*, wherein $R^3$ is allyl or homoallyl, can be reacted with oxygen in the presence of $PdCl_2$ and CuCl to afford a compound of Formula I*, wherein $R^3$ is 2-oxopropyl or 3-oxobutyl respectively.

(17) a compound of Formula I*, wherein $R^3$ is 2-oxopropyl or 3-oxobutyl, can be reacted with MeMgX, wherein X is Cl, Br or I, to give a compound of Formula I*, wherein $R^3$ is 2-hydroxy-2-methylpropyl or 3-hydroxy-3-methylpropyl respectively.

(18) a compound of Formula I*, wherein $R^3$ is —$CH_2CO_2Me$ can be treated with MeMgX, wherein X is Cl, Br or I, to give a compound of Formula I*, wherein $R^3$ is 2-hydroxy-2-methylpropyl.

(19) a compound of Formula I*, wherein $R^3$ is allyl or —$CH_2C(Me)\!=\!CH_2$, can be hydrocyanated with TsCN in the presence of triphenylsilane and various cobalt catalysts to afford compounds of Formula I*, wherein $R^3$ is —$CH_2CH$ (CN)Me or —$CH_2CMe_2CN$ respectively.

(20) a compound of Formula I*, wherein $R^3$ is $CH_2C(Me)_2$ CN, can be treated with acetamide in the presence of $PdCl_2$ to give a compound of Formula I*, wherein $R^3$ is $CH_2CMe_2CONH_2$.

(21) a compound of Formula I*, wherein $R^3$ is —$CH_2C$ (Me)=$CH_2$ can be treated with m-CPBA followed by lithium triethylborohydride to afford a compound of Formula I*, wherein $R^3$ is 2-hydroxy-2-methylpropyl.

In an eighth process, certain compounds of the invention of Formula I are prepared as follows. A β-chloroethyl phenyl ketone of Formula L is reacted with the Grignard or organozinc derivative of a methylallyl halide of Formula LI to afford a chloroalcohol of Formula LII which reacted with a mono-Boc protected diamine of Formula LIII to give and aminoalcohol of Formula LIV. Reaction with methyl chloroformate leads to a hydroxycarbamate of Formula LV. Treatment of LV with sodium hydride affords oxazinone LVI. The methylallyl side chain of LVI is epoxidized with m-CPBA and LVII, the resulting epoxide, is reduced with lithium triethylborohydride to give tertiary alcohol LVIII. Removal of the Boc protecting group from LVIII yields amine LIX which is reacted with various heterocyclic compounds of Formula XXXV as described in the fifth process above to afford compounds of Formula I.

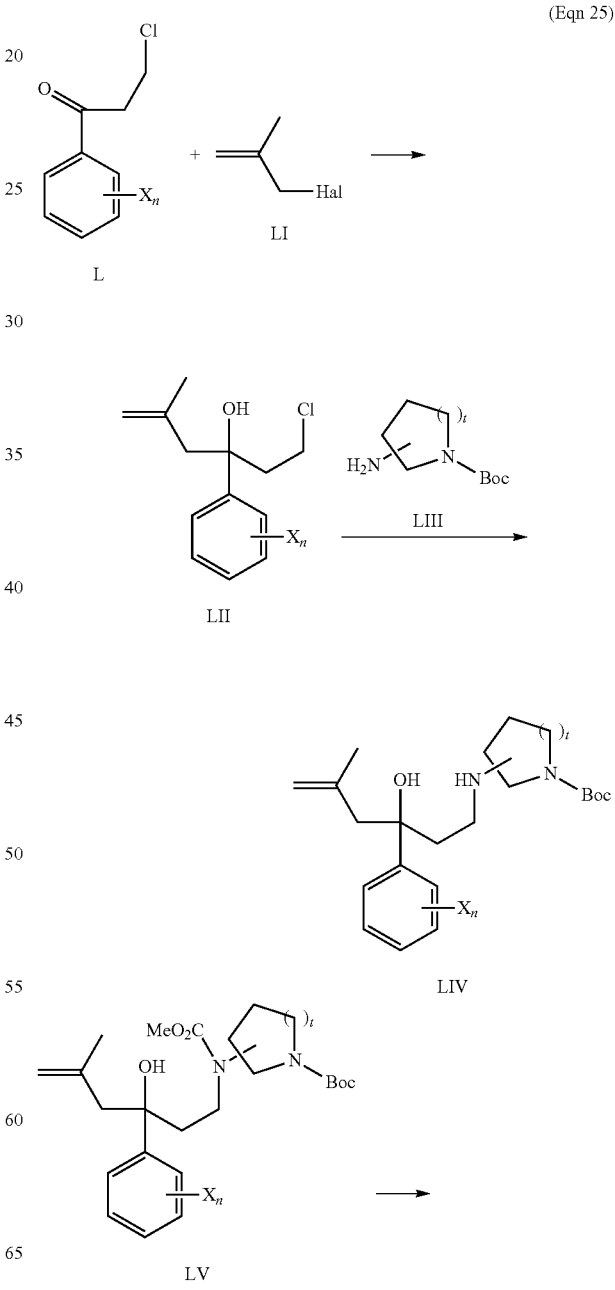

(Eqn 25)

-continued

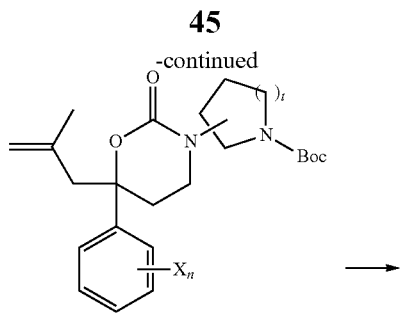

LVI

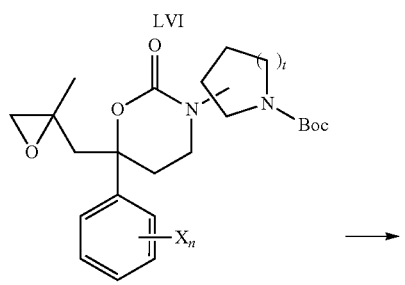

LVII

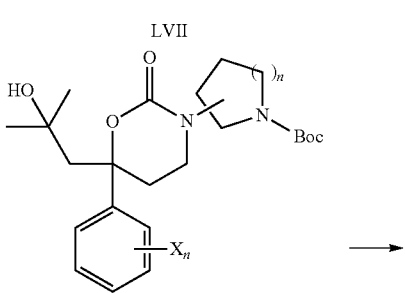

LVIII

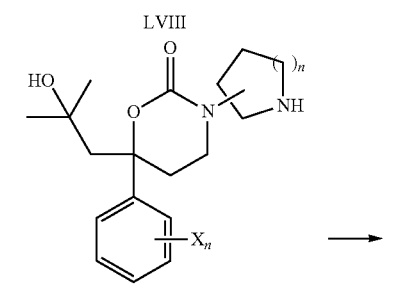

LIX

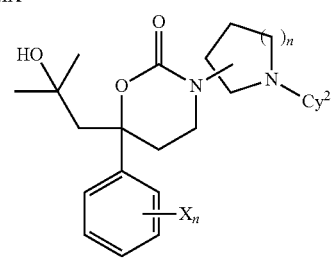

I**

LC-MS Methods

Method 1 [LC-MS (3 min)]
Column: Chromolith SpeedRod, RP-18e, 50×4.6 mm; Mobil phase: A:
0.01% TFA/water, B: 0.01% TFA/CH₃CN; Flow rate: 1 mL/min; Gradient:

| Time (min) | A% | B% |
|---|---|---|
| 0.0 | 90 | 10 |
| 2.0 | 10 | 90 |
| 2.4 | 10 | 90 |
| 2.5 | 90 | 10 |
| 3.0 | 90 | 10 |

Method 2 (10-80)

| Column | YMC-PACK ODS-AQ, 50 × 2.0 mm 5 μm |
| Mobile Phase | A: water (4 L) + TFA (1.5 mL)) |
| | B: acetonitrile (4 L) + TFA (0.75 mL)) |

| TIME (min) | A% | B% |
|---|---|---|
| 0 | 90 | 10 |
| 2.2 | 20 | 80 |
| 2.5 | 20 | 80 |

| Flow Rate | 1 mL/min |
| Wavelength | UV 220 nm |
| Oven Temp | 50° C. |
| MS ionization | ESI |

Method 3 (30-90)

| Column | YMC-PACK ODS-AQ, 50 × 2.0 mm 5 μm |
| Mobile Phase | A: water (4 L) + TFA (1.5 mL)) |
| | B: acetonitrile (4 L) + TFA (0.75 mL)) |

| TIME (min) | A% | B% |
|---|---|---|
| 0 | 70 | 30 |
| 2.2 | 10 | 90 |
| 2.5 | 10 | 90 |

| Flow Rate | 1 mL/min |
| Wavelength | UV 220 nm |
| Oven Temp | 50° C. |
| MS ionization | ESI |

PREPARATION 1

(S)-6-(2-hydroxy-2-methylpropyl)-6-phenyl-3-((S)-piperidin-3-yl)-1,3-oxazinan-2-one

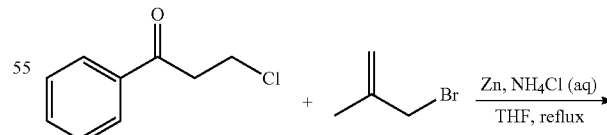

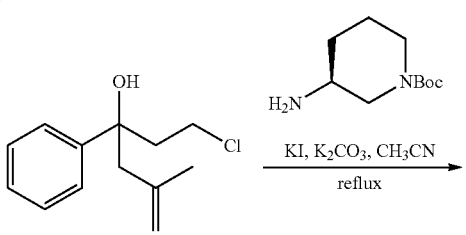

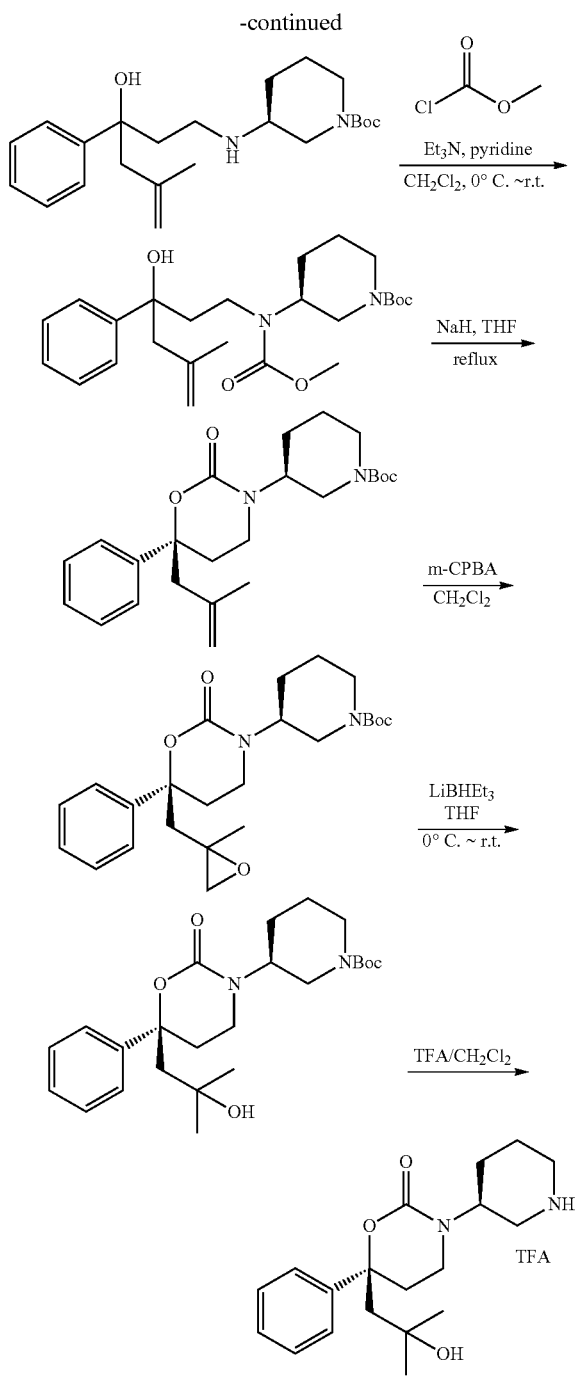

Step 1

To a well stirred mixture of 3-chloropropiophenone (10.0 g, 59.3 mmol), zinc powder (4.0 g, 1.03 equiv), satd aq NH$_4$Cl solution (150 mL), THF (70 mL), a solution of the 3-bromo-2-methylprop-1-ene (16 g, 2 equiv) was added slowly. The reaction was exothermic mildly. After the addition, the mixture was heated to reflux for 1.5 h. After being cooled to rt, the mixture was diluted with EtOAc (200 mL), separated, washed with brine (35 mL), and dried over Na$_2$SO$_4$. After filtration and concentration, the residue was purified by chromatography on a 120 g silica gel column, eluted with a 0-10% methanol in CH$_2$Cl$_2$ gradient, to afford 1-chloro-5-methyl-3-phenylhex-5-en-3-ol (8.67 g product, 65% yield).

Step 2

A mixture of 1-chloro-5-methyl-3-phenylhex-5-en-3-ol (5.16 g, 23 mmol), (S)-tert-butyl 3-aminopiperidine-1-carboxylate (6.9 g, 1.5 equiv), KI (4.0 g, 1.05 equiv), K$_2$CO$_3$ (4.77 g, 1.5 equiv) were mixed with acetonitrile (100 mL) and heated to reflux for 20 h. The mixture was filtered through a pad of Celite, concentrated and purified by chromatography on a 120 g silica gel column, eluted with a 0-10% methanol in CH$_2$Cl$_2$ gradient, to afford (3S)-tert-butyl 3-(3-hydroxy-5-methyl-3-phenylhex-5-enylamino)piperidine-1-carboxylate (8.41 g, 94% yield). LC-MS Method 1 $t_R$=1.56 min., m/z 389 (M+1).

Step 3

A solution of (3S)-tert-butyl 3-(3-hydroxy-5-methyl-3-phenylhex-5-enylamino)piperidine-1-carboxylate (8.41 g, 21.65 mmol), triethylamine (4.53 mL, 1.5 equiv), pyridine (1.75 mL, 1 equiv) in dichloromethane (250 mL) was cooled to 0° C. Methyl chloroformate (3.35 mL, 2 equiv) was added slowly during a 10 min period. After 15 min, the mixture was warmed to it slowly and stirred 3 h. The mixture was diluted with ether (350 mL), washed with 5% aq HCl solution (2×30 mL), satd aq NaHCO$_3$ solution (25 mL), brine (25 mL), and dried over Na$_2$SO$_4$. After filtration and concentration, the residue was purified by chromatography on a 120 g silica gel column, eluted with a 30-85% EtOAc in hexanes gradient, to afford (3S)-tert-butyl 3-((3-hydroxy-5-methyl-3-phenylhex-5-enyl)(methoxycarbonyl)amino)piperidine-1-carboxylate (5.80 g, 60%). LC-MS Method 1 $t_R$=2.08 min., m/z 447 (M+1).

Step 4

To a solution of (3S)-tert-butyl 3-((3-hydroxy-5-methyl-3-phenylhex-5-enyl)(methoxycarbonyl)amino)piperidine-1-carboxylate (5.80 g, 13 mmol) in dry THF (200 mL) was added NaH (60% in mineral oil, 1.04 g, 2 equiv). The mixture was heated to reflux for 2 h. After being cooled down to rt, the mixture was diluted with ether (200 mL), quenched with satd aq NH$_4$Cl solution (25 mL), washed with 1% HCl solution (50 mL), brine (35 mL), and dried over Na$_2$SO$_4$. After filtration and concentration, the residue was purified by chromatography on a 120 g silica gel column, eluted with a 40-70% EtOAc in hexanes gradient to afford (5)-tert-butyl 3-((R)-6-(2-methylallyl)-2-oxo-6-phenyl-1,3-oxazinan-3-yl)piperidine-1-carboxylate (2.98 g, 55% yield). LC-MS Method 1 $t_R$=1.92 min., m/z 437 (M+Na).

Step 5

To a solution of (S)-tert-butyl 3-((R)-6-(2-methylallyl)-2-oxo-6-phenyl-1,3-oxazinan-3-yl)piperidine-1-carboxylate (2.98 g, 7.2 mmol) in dichloromethane (200 mL) was added m-CPBA (77% maximum, 3.3 g, 2 equiv). The mixture was stirred 3 h at rt before being diluted by dichloromethane (150 mL), washed by 5% NaOH solution (2×40 mL), 30% aq sodium thiosulfate solution (30 mL), satd aq NaHCO$_3$ (30 mL), 30% aq sodium thiosulfate solution (30 mL), satd aq NaHCO$_3$ (30 mL), brine (30 mL), and dried over Na$_2$SO$_4$. Filtration and concentration gave crude (3S)-tert-butyl 3-((6S)-6-((2-methyloxiran-2-yl)methyl)-2-oxo-6-phenyl-1,3-oxazinan-3-yl)piperidine-1-carboxylate (2.98 g 93% yield) which was used for next steps without further purification. LC-MS Method 1 $t_R$=1.68 min., m/z 431 (M+1).

Step 6

A solution of (3S)-tert-butyl 3-((6S)-6-((2-methyloxiran-2-yl)methyl)-2-oxo-6-phenyl-1,3-oxazinan-3-yl)piperidine-1-carboxylate (2.87 g, 6.67 mmol) in dry THF (50 mL) was cooled to 0° C. After 20 min, the mixture was allowed to warm up to rt slowly. The mixture was stirred 2 h at rt, before being cooled to 0° C. again. The mixture was quenched with water (10 mL), 1% aq HCl (25 mL), diluted with EtOAc (120 mL).

After separation, the organic layer was washed with brine (20 mL), dried over Na₂SO₄. After filtration and concentration, the residue was purified by chromatography on a 120 g silica gel column, eluted with a 50-100% EtOAc in hexanes gradient, to afford (S)-tert-butyl 3-((S)-6-(2-hydroxy-2-methylpropyl)-2-oxo-6-phenyl-1,3-oxazinan-3-yl)piperidine-1-carboxylate (0.55 g, 19% yield). LC-MS Method 1 $t_R$=1.64 min., m/z 455 (M+Na).

Step 7

(S)-tert-butyl 3-((S)-6-(2-hydroxy-2-methylpropyl)-2-oxo-6-phenyl-1,3-oxazinan-3-yl)piperidine-1-carboxylate (25 mg, 0.058 mmol) was dissolved in 20% TFA/CH₂Cl₂ (8 mL) solution and stirred 30 min at rt. The mixture was concentrated, redissolved in CH₂Cl₂ (25 mL), washed with satd aq NaHCO₃ solution (10 mL), brine (8 mL), dried over Na₂SO₄. After filtration and concentration, the crude (S)-6-(2-hydroxy-2-methylpropyl)-6-phenyl-3-((S)-piperidin-3-yl)-1,3-oxazinan-2-one as its TFA salt which was used without further purification. LC-MS Method 1 $t_R$=0.86 min., m/z 333 (M+1).

PREPARATION 2

(S)-6-(2-hydroxy-2-methylpropyl)-6-phenyl-3-((S)-pyrrolidin-3-yl)-1,3-oxazinan-2-one

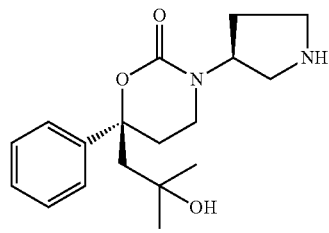

The title compound was prepared following procedures analogous to those described in Preparation 1 using (S)-tert-butyl 3-aminopyrrolidine-1-carboxylate in Step 2.

PREPARATION 3

(S)-tert-butyl 3-((R)-6-(4-fluorophenyl)-6-(3-hydroxypropyl)-2-oxo-1,3-oxazinan-3-yl)piperidine-1-carboxylate

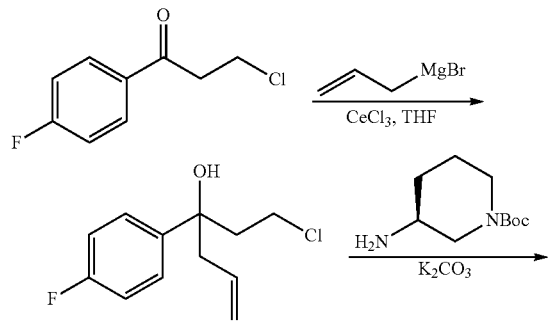

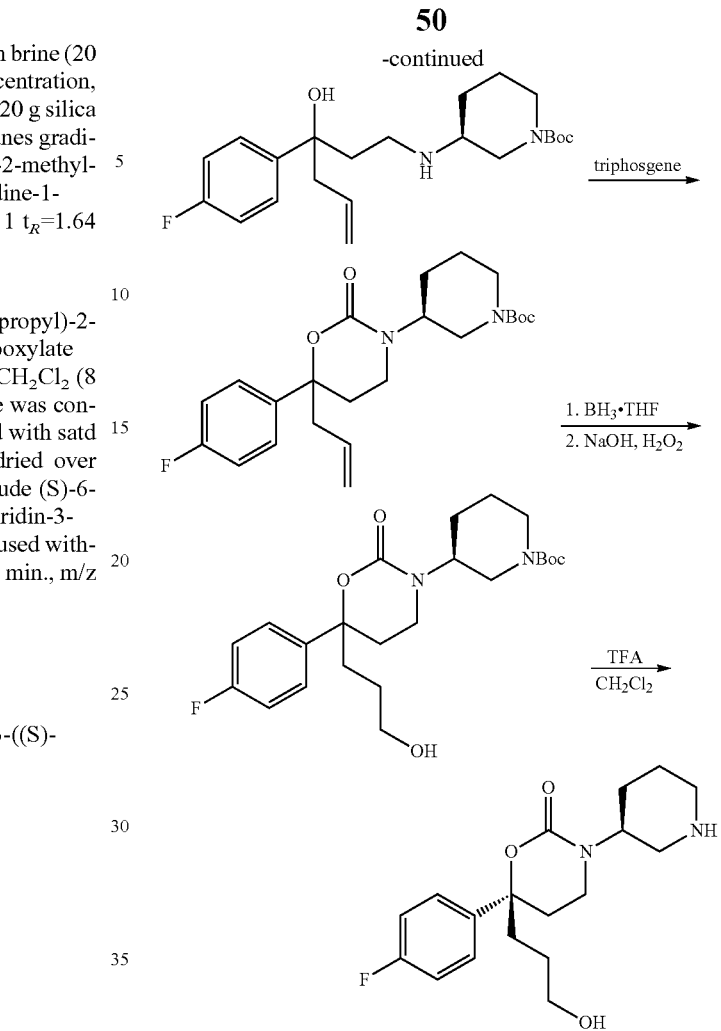

Step 1. 1-chloro-3-(4-fluorophenyl)hex-5-en-3-ol

A 250-mL flask was charged with anhydrous CeCl₃ (5.58 g, 22.6 mmol) and THF (40 mL). The mixture was vigorously stirred for 3.5 h at rt. The suspension was then cooled to −78 °C. and a solution of allylmagnesium bromide (1.0 M in THF, 21 mL, 21.0 mmol) was added. After stirring for 2 h at −78 °C., a solution of 3-chloro-1-(4-fluorophenyl)propan-1-one (2.522 g, 13.5 mmol) in THF (30 mL) was added via cannula. The reaction mixture was allowed to slowly warm to 8° C. while stirring overnight (18 h). The reaction was then quenched with satd aq NaHCO₃, extracted with EtOAc, and dried over Na₂SO₄. After the solvents were evaporated, the residue was purified by chromatography on silica gel eluted with hexanes/EtOAc to afford of 1-chloro-3-(4-fluorophenyl)hex-5-en-3-ol (3.0049 g, 97%) as an oil. LC-MS Method 1 $t_R$=1.79 min, m/z 213, 211 (M-OH)⁺; ¹H NMR (400 MHz, CDCl₃) δ 7.37-7.32 (m, 2H), 7.07-7.02 (m, 2H), 5.57-5.47 (m, 1H), 5.20-5.19 (m, 1H), 5.16 (m, 1H), 3.59-3.52 (m, 1H), 3.24-3.18 (m, 1H), 2.70 (dd, J=13.8, 5.9 Hz, 1H), 2.50 (dd, J=13.8, 8.5 Hz, 1H), 2.29 (t, J=7.9 Hz, 2H), 2.22 (s, 1H); ¹⁹F NMR (376 MHz, CDCl₃) δ−116.52 (m).

Step 2

A mixture of 1-chloro-3-(4-fluorophenyl)hex-5-en-3-ol (760 mg, 3.3 mmol), (S)-tert-butyl 3-aminopiperidine-1-carboxylate (1.0 g, 5 mmol), KI (1.1 g, 6.7 mmol) and K₂CO₃ (920 mg, 6.7 mmol) in acetonitrile (33 mL) was heated to reflux overnight. The reaction mixture was filtered. The filtrate was condensed to give the crude product, which was purified by preparative TLC to afford (3S)-tert-butyl-3-(3-(4-fluorophenyl)-3-hydroxyhex-5-enylamino)piperidine-1-carboxylate (500 mg, 38%). ¹H NMR: (CDCl₃): 1.23 (m, 1H), 1.38 (d, 9H), 1.57 (m, 1H), 1.75 (broad, 1H), 1.94 (m, 2H), 2.37 (m, 1H), 2.43 (m, 2H), 2.56 (m, 1H), 2.80 (broad, 3H), 3.49 (broad, 1H), 3.71 (broad, 3H), 4.95 (d, 2H), 5.56 (m, 1H), 6.95 (t, 2H), 7.32 (m, 2H).

Step 3

To a solution of (3S)-tert-butyl 3-(3-(4-fluorophenyl)-3-hydroxyhex-5-enylamino)-piperidine-1-carboxylate (500 mg, 1.27 mmol) and triethylamine (515 mg, 5.1 mmol) in dried methylene chloride (13 mL) at 0° C. was added triphosgene (126 mg, 0.42 mmol). The mixture was stirred at room temperature till the reaction was over. Water was added, and the layers were separated. The aqueous layer was extracted with methylene chloride. The combined organic layer was washed with water, dried over Na₂SO₄, and condensed to give the crude product, which was purified by column chromatography on silica gel to afford (3S)-tert-butyl 3-(6-allyl-6-(4-fluorophenyl)-2-oxo-1,3-oxazinan-3-yl)piperidine-1-carboxylate (70 mg, 13%). ¹H NMR: (CDCl₃): 1.37 (d, 9H), 1.43 (m, 1H), 1.64 (m, 1H), 2.22 (m, 2H), 2.64 (m, 5H), 3.11 (m, 1H), 3.91 (broad, 3H), 5.00 (q, 2H), 5.65 (m, 1H), 6.99 (t, 3H), 7.20 (m, 2H).

Step 4

The two diastereomers of (3S)-tert-butyl 3-(6-(4-fluorophenyl)-6-(3-hydroxypropyl)-2-oxo-1,3-oxazinan-3-yl) piperidine-1-carboxylate were prepared from (3S)-tert-butyl 3-(6-allyl-6-(4-fluorophenyl)-2-oxo-1,3-oxazinan-3-yl)piperidine-1-carboxylate by treatment with (i) BH₃ in THF and (ii) H₂O₂ and NaOH.

Isomer 1: (S)-tert-butyl 3-((R)-6-(4-fluorophenyl)-6-(3-hydroxypropyl)-2-oxo-1,3-oxazinan-3-yl)piperidine-1-carboxylate. LC-MS Method 2 $t_R$=1.308 min, m/z=459; ¹H NMR (CDCl₃) 1.24 (m, 1H), 1.34 (s, 9H), 1.42 (m, 2H), 1.62 (m, 3H), 1.80-1.97 (m, 2H), 2.10 (m, 1H), 2.24 (m, 1H), 2.34-2.48 (m, 1H), 2.57 (m, 1H), 2.67 (m, 1H), 3.10 (m, 1H), 3.48 (t, 2H), 3.55-4.06 (m, 3H), 6.98 (t, 2H), 7.18 (m, 2H).

Isomer 2: (S)-tert-butyl 3-((S)-6-(4-fluorophenyl)-6-(3-hydroxypropyl)-2-oxo-1,3-oxazinan-3-yl)piperidine-1-carboxylate. LC-MS Method 2 $t_R$=1.313 min, m/z=337; ¹H NMR (CDCl₃) 1.27 (m, 1H), 1.39 (s, 9H), 1.41-1.52 (m, 4H), 1.56 (m, 2H), 1.59-1.61 (m, 1H), 1.83-2.00 (m, 2H), 2.09-2.20 (m, 1H), 2.25 (m, 1H), 2.39-2.57 (m, 1H), 2.69-2.83 (m, 2H), 3.01 (m, 1H), 3.50 (t, 2H), 3.70-3.88 (s, 1H), 3.89-4.00 (m, 2H), 6.94-7.03 (t, 2H), 7.18-7.29 (m, 2H).

Step 5

A solution of (S)-tert-butyl 3-((R)-6-allyl-6-(4-fluorophenyl)-2-oxo-1,3-oxazinan-3-yl)piperidine-1-carboxylate (150 mg, 0.359 mmol) in 20% TFA/CH₂Cl₂ (5 mL) was stirred at 0° C. for 2 h. The mixture was concentrated to give (R)-6-allyl-6-(4-fluorophenyl)-3-((S)-piperidin-3-yl)-1,3-oxazinan-2-one (112 mg, crude), which was used for the next without further purification.

EXAMPLE 1

(S)-3-((S)-1-(3-fluoropyridin-2-yl)piperidin-3-yl)-6-(2-hydroxy-2-methylpropyl)-6-phenyl-1,3-oxazinan-2-one

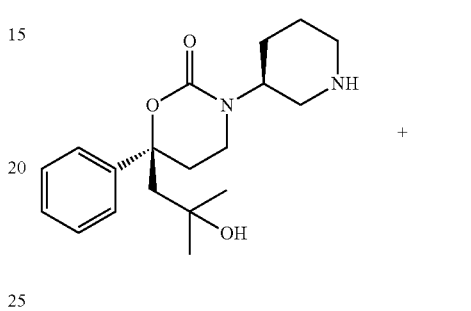

+

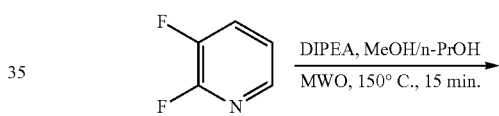

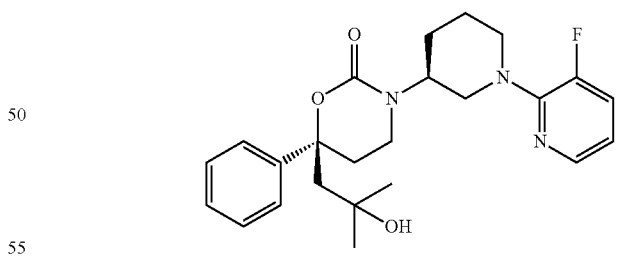

A solution of (S)-6-(2-hydroxy-2-methylpropyl)-6-phenyl-3-((S)-piperidin-3-yl)-1,3-oxazinan-2-one TFA salt (12 mg, 0.036 mmol), 2,3-difluoropyridine (6 mg, 2equiv), and i-Pr₂NEt (30 μL, 5 equiv) in 1:6 MeOH/n-Propanol (2 mL) was heated in the microwave oven for 15 min. at 150° C. After being cooled to rt, the mixture was acidified with 5% aq HCl solution and purified by prep HPLC to afford (S)-3-((S)-1-(3-fluoropyridin-2-yl)piperidin-3-yl)-6-(2-hydroxy-2-methylpropyl)-6-phenyl-1,3-oxazinan-2-one (5.8 mg, 50% yield). LC-MS Method 1 $t_R$=1.51 min, m/z=428(M+1); ¹H NMR (CD₃OD) 7.92(dd, 1H), 7.51-7.28(m, 6H), 6.88(m, 1H), 4.10 (m, 1H), 3.91(m, 2H), 3.06(td, 1H), 2.51(m, 2H), 2.19(s, 2H), 1.24(s, 3H), 0.94(s, 3H).

EXAMPLE 2

(S)-6-(2-hydroxy-2-methylpropyl)-6-phenyl-3-((S)-1-(3-(trifluoromethyl)pyridin-2-yl)piperidin-3-yl)-1,3-oxazinan-2-one

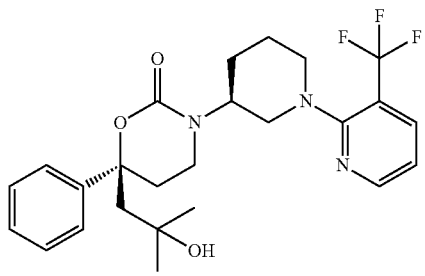

The title compound was prepared following a procedure analogous to that described in Example 1 using 2-chloro-3-trifluoromethylpyridine at 160° C. for 35 min. LC-MS Method 1 $t_R$=1.8 min, m/z=478(M+1); ¹H NMR (CD₃OD) 8.44(d, 1H), 7.99(d, 1H), 7.44-7.28(m, 5H), 7.15(m, 1H), 3.05(t, 1H), 2.48(m, 2H), 2.18(s, 2H), 1.72(m, 2H), 1.57(m, 2H), 1.23(s, 3H), 0.94(s, 3H).

EXAMPLE 3

(S)-6-(2-hydroxy-2-methylpropyl)-6-phenyl-3-((S)-1-(4-(trifluoromethyl)pyridin-2-yl)piperidin-3-yl)-1,3-oxazinan-2-one

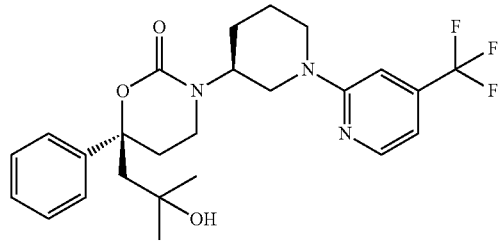

The title compound was prepared following a procedure analogous to that described in Example 1 using 2-bromo-4-trifluoromethylpyridine at 150° C. for 20 min. LC-MS Method 1 $t_R$=1.76 min, m/z=478(M+1); ¹H NMR (CD₃OD) 8.23(d, 1H), 7.41(m, 4H), 7.33(m, 1H), 6.93((s, 1H), 6.80(d, 1H), 4.26(d, 1H), 4.06(d, 1H), 3.90(m, 1H), 2.78(m, 3H), 2.51(m, 2H), 2.19(s, 2H), 1.83(m, 3H), 1.58(m, 1H), 1.24(s, 3H), 0.94(s, 3H).

EXAMPLE 4

(S)-6-(2-hydroxy-2-methylpropyl)-6-phenyl-3-((S)-1-(5-(trifluoromethyl)Pyridin-2-yl)piperidin-3-yl)-1,3-oxazinan-2-one

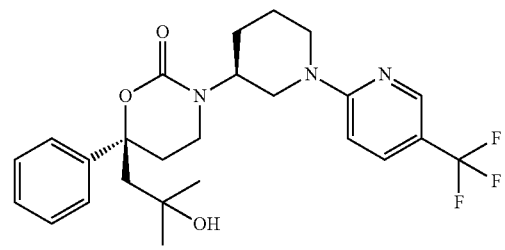

The title compound was prepared following a procedure analogous to that described in Example 1 using 2-chloro-5-(trifluoromethyl)pyridine at 120° C. for 20 min. LC-MS Method 1 $t_R$=1.82 min, m/z=478(M+1); ¹H NMR (CD₃OD) 8.29(d, 1H), 8.78(m, 1H), 7.46-7.29(m, 5H), 6.97(dt, 1H), 4.35-4.12(m, 2H), 3.92(m, 1H), 2.87(t, 1H), 2.77(m, 1H), 2.52(m, 2H), 2.19(s, 2H), 1.25(d, 3H), 0.96(d, 3H).

EXAMPLE 5

(S)-6-(2-hydroxy-2-methylpropyl)-6-phenyl-3-((S)-1-(6-(trifluoromethyl)pyridin-2-yl)piperidin-3-yl)-1,3-oxazinan-2-one The title compound was prepared following a procedure analogous to that described in Example 1 using 2-fluoro-6-(trifluoromethyl)pyridine at 120° C. for 30 min. LC-MS Method 1 $t_R$=1.84 min, m/z=478(M+1); ¹H NMR (CD₃OD)

7.64(t, 1H), 7.45-7.30(m, 5H), 6.92(m, 2H), 2.74(m, 3H), 2.49(m, 2H), 2.20(s, 2H), 1.82(m, 2H), 1.24(s, 3H), 0.96(s, 3H).

EXAMPLE 6

(S)-6-(2-hydroxy-2-methylpropyl)-3-((S)-1-(6-methoxypyridin-3-yl)piperidin-3-yl)-6-phenyl-1,3-oxazinan-2-one

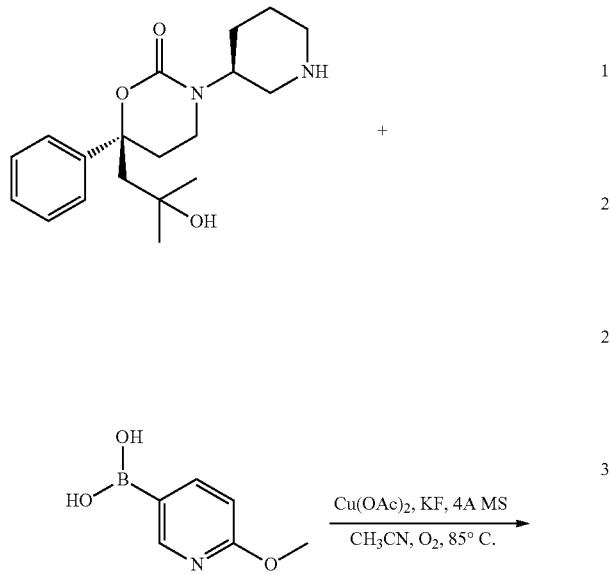

A suspension of 6-methoxypyridin-3-ylboronic acid (4 mg, 1.5equiv), Cu(OAc)$_2$ (1 mg, cat. amount), potassium fluoride (1.1 mg, 1.05 equiv), and powdered activated 4 Å Molecular Sieves (15 mg) in acetonitrile (1.5 mL) was stirred in a test tube at ambient conditions for 10 min. A solution of (S)-6-(2-hydroxy-2-methylpropyl)-6-phenyl-3-((S)-piperidin-3-yl)-1,3-oxazinan-2-one TFA salt (6 mg, 0.018 mmol) in acetonitrile (1 mL) was added. The test tube was sealed with a septum and a balloon of oxygen gas was attached to maintain the oxygen atmosphere. The mixture was heated overnight at 85° C. LC-MS found the product peak. The mixture was filtered and purified by prep HPLC to afford (S)-6-(2-hydroxy-2-methylpropyl)-3-((S)-1-(6-methoxypyridin-3-yl)piperidin-3-yl)-6-phenyl-1,3-oxazinan-2-one (4.5 mg, 76% yield). LC-MS Method 1 t$_R$=1.37 min, m/z=440(M+1); $^1$H NMR (CD$_3$OD) 7.82(m, 2H), 7.43-7.29(m, 5H), 7.11(m, 1H), 4.14(m, 1H), 4.00(s, 3H), 3.56(t, 1H), 2.77(m, 3H), 2.52(m, 2H), 2.19(s, 2H), 1.23(s, 3H), 0.95(s, 3H).

EXAMPLE 7

(S)-3-((S)-1-(5-fluoropyrimidin-2-yl)piperidin-3-yl)-6-(2-hydroxy-2-methylpropyl)-6-phenyl-1,3-oxazinan-2-one

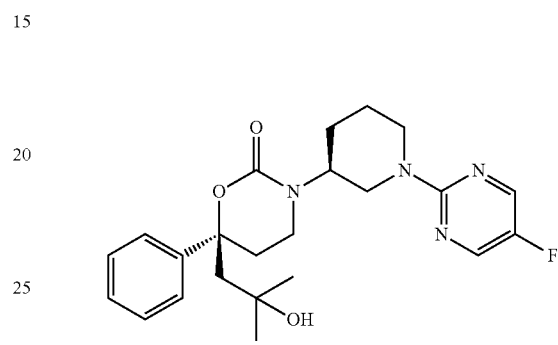

The title compound was prepared following a procedure analogous to that described in Example 1 using 2-chloro-5-fluoropyrimidine at 100° C. for 10 min. LC-MS Method 1 t$_R$=1.6 min, m/z=429(M+1); $^1$H NMR (CD$_3$OD) 8.23(s, 2H), 7.45-7.30(m, 5H), 4.57(d, 1H), 4.40(dd, 1H), 3.85(m, 1H), 2.81(t, 1H), 2.70(m, 2H), 2.48(m, 2H), 2.18(s, 2H), 1.90-1.75 (m, 3H), 1.54(m, 1H), 1.23(s, 3H), 0.94(s, 3H).

EXAMPLE 8

(S)-3-((S)-1-(5-chloropyrimidin-2-yl)piperidin-3-yl)-6-(2-hydroxy-2-methylpropyl)-6-phenyl-1,3-oxazinan-2-one

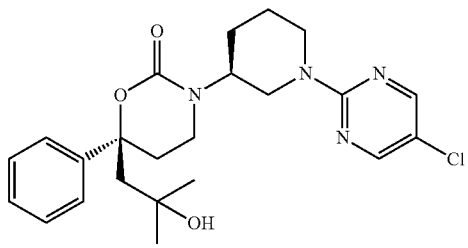

The title compound was prepared following a procedure analogous to that described in Example 1 using 2,5-dichloropyrimidine at 150° C. for 15 min. LC-MS Method 1 tR=1.72 min, m/z=445, 447(M+1); 1H NMR (CD30D) 8.22 (s, 2H), 7.41(q, 2H), 7.33(m, 3H), 7.26(s, 2H), 4.56(m, 2H), 3.21(m, 1H), 2.94(m, 1H), 2.72(m, 2H), 2.45-2.28(m, 2H), 2.24(s, 2H), 1.83(m, 2H), 1.17(s, 3H), 1.06(s, 3H).

EXAMPLE 9

(S)-3-((S)-1-(2,6-dimethylpyrimidin-4-yl)piperidin-3-yl)-6-(2-hydroxy-2-methylpropyl)-6-phenyl-1,3-oxazinan-2-one

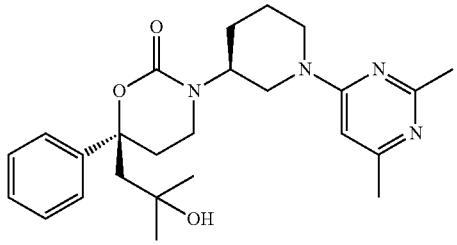

The title compound was prepared following a procedure analogous to that described in Example 1 using 4-chloro-2,6-dimethylpyrimidine at 100° C. for 10 min. LC-MS Method 1 $t_R$=4.04 min, m/z=439(M+1); $^1$H NMR (CD$_3$OD) 7.48-7.31 (m, 5H), 6.79(d, 1H), 2.53(s, 3H), 2.42(d, 3H), 2.20(s,2H), 1.56(m, 1H), 1.24(s, 3H), 0.94(s, 3H).

EXAMPLE 10

Methyl 2-((S)-34(S)-6-(2-hydroxy-2-methylpropyl)-2-oxo-6-phenyl-1,3-oxazinan-3-yl)piperidin-1-yl)pyrimidine-5-carboxylate

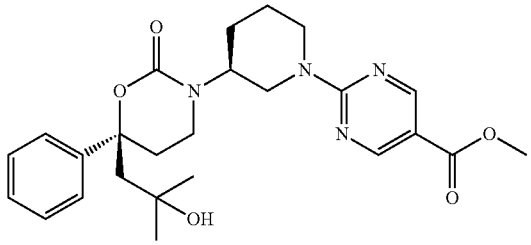

The title compound was prepared following a procedure analogous to that described in Example 1 using methyl 2-chloropyrimidine-5-carboxylate in CH$_2$Cl$_2$/n-PrOH at rt. LC-MS Method 1 $t_R$=1.56 min, m/z=469(M+1); $^1$H NMR (CDCl$_3$) 8.88(s, 2H), 7.43(t, 2H), 7.33(m, 3H), 4.73(dd, 3H), 3.89(s, 3H), 3.68(m, 1H), 3.26(dt, 1H), 3.17(t, 1H), 2.84(t, 1H), 2.74(td, 1H), 2.28(d, 2H), 2.00(m, 1H), 1.87(t, 2H), 1.56(m, 1H), 1.20(s, 3H), 1.06(s, 3H).

EXAMPLE 11

(S)-6-(2-hydroxy-2-methylpropyl)-6-phenyl-3-((S)-1-(2-(trifluoromethyl)pyrimidin-4-yl)piperidin-3-yl)-1,3-oxazinan-2-one

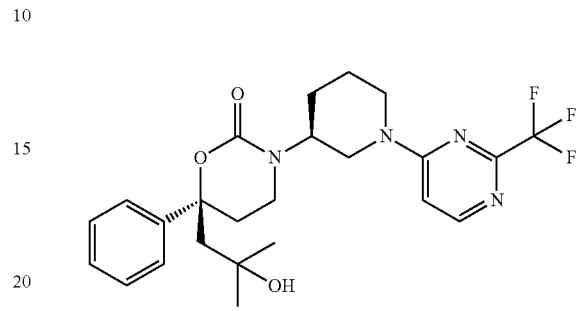

LC-MS Method 1 tR=1.59 min, m/z=479(M+1); 1H NMR (CD3OD) 8.22(d, 1H), 7.45-7.31(m, 5H), 6.86(d, 1H), 3.83 (m, 1H), 2.97-2.70(m, 3H), 2.51(m, 2H), 2.19(s, 2H), 1.57(m, 1H), 1.27(m, 1H), 1.25(s, 3H), 0.95(s, 3H).

EXAMPLE 12

(S)-6-(2-hydroxy-2-methylpropyl)-3-((S)-1-(5-methoxypyrimidin-2-yl)piperidin-3-yl)-6-phenyl-1,3-oxazinan-2-one

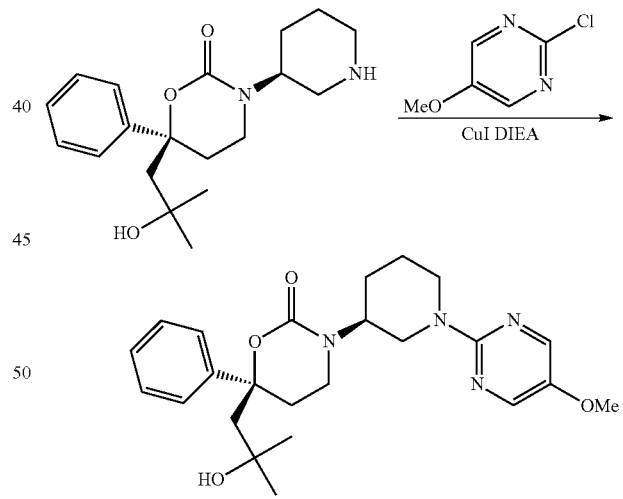

A round-bottom-flask containing S-6-(2-hydroxy-2-methylpropyl)-6-phenyl-3-(S-piperidin-3-yl)-1,3-oxazinan-2-one (50 mg, 0.15 mmol) in i-Pr$_2$NEt (5 mL) was charged with 2-chloro-5-methoxypyrimidine (30 mg, 0.207 mmol) and CuI (0.57 mg, 0.003 mmol). The reaction solution was heated at 80° C. for 4 h under nitrogen. After the reaction was finished, the reaction mixture was concentrated and purified by prep HPLC to give (S)-6-(2-hydroxy-2-methylpropyl)-3-((S)-1-(5-methoxypyrimidin-2-yl)piperidin-3-yl)-6-phenyl-1,3-oxazinan-2-one (7.2 mg, 10.8%) $^1$H NMR (CD$_3$OD): δ0.91 (s, 3H), 1.22 (s, 3H), 1.26 (m, 1H), 1.31 (m, 1H), 1.53 (m, 2H), 1.77 (m, 3H), 2.00 (s, 2H), 2.46 (m, 2H), 2.73 (m, 3H), 3.77 (s, 2H), 3.82 (m, 1H), 4.30 (m, 1H), 4.45 (m, 1H), 7.37 (m, 5H), 7.29 (s, 2H).

EXAMPLE 13

(S)-6-(2-hydroxy-2-methylpropyl)-3-((S)-1-(5-methylthiazol-2-yl)piperidin-3-yl)-6-phenyl-1,3-oxazinan-2-one

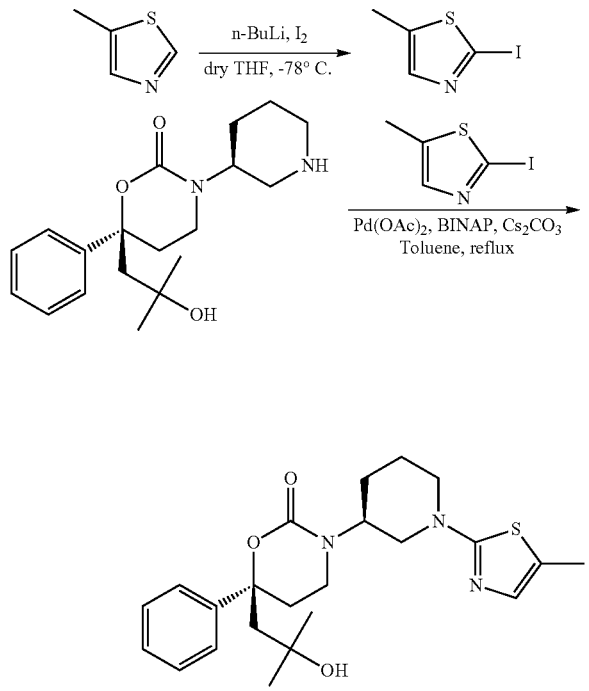

Step 1

To a solution of 5-methylthiazole (200 mg, 2.02 mmol) in 3 mL of dry THF was added 1.62 mL of n-BuLi (2.5 M, 4.04 mmol) at −78° C. dropwise under nitrogen. The reaction was stirred for 30 min at −78° C., and a solution of iodine (620 mg, 2.42 mmol) in 2 mL of THF was added. The solution was stirred overnight at rt. Satd aqueous $NH_4Cl$ (3 mL) was added to quench the reaction, and the mixture was extracted with EtOAc. The combined organic layer was evaporated, and the residue was purified by chromatography on silica gel to afford 2-iodo-5-methylthiazole (60 mg, 12%).

Step 2

To a mixture of S-6-(2-hydroxy-2-methylpropyl)-3-(S-1-(5-methylthiazol-2-yl)piperidin-3-yl)-6-phenyl-1,3-oxazinan-2-one (31 mg, 0.092 mmol), 2-iodo-5-methylthiazole (25 mg, 0.11 mmol) and $Cs_2CO_3$ (152 mg, 0.47 mmol) in 3 mL of dry toluene were added $Pd(OAc)_2$ (2.1 mg, 0.0093 mmol) and BINAP (5.8 mg, 0.0093 mmol) under nitrogen. The mixture was heated at reflux for 3 h. The solvent was evaporated, and the residue was purified by prep HPLC to afford S-6-(2-hydroxy-2-methylpropyl)-3-((S)-1-(5-methylthiazol-2-yl)piperidin-3-yl)-6-phenyl-1,3-oxazinan-2-one (8 mg, 20%). $^1$H NMR ($CD_3OD$): δ 0.88 (s, 3H), 1.17 (s, 3H), 1.65 (m, 1H), 1.90 (m, 3H), 2.14 (s, 2H), 2.26 (s, 3H), 2.48 (m, 2H), 2.75 (m, 1H), 3.00 (m, 2H), 3.39 (m, 1H), 3.60 (m, 1H), 3.72 (m, 1H), 3.96 (m, 1H), 6.78 (s, 1H), 7.31-7.41 (m, 5H).

EXAMPLE 14

(S)-3-((S)-1-(5-chloropyrimidin-2-yl)pyrrolidin-3-yl)-6-(2-hydroxy-2-methylpropyl)-6-phenyl-1,3-oxazinan-2-one

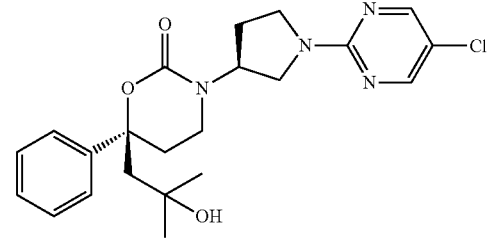

The title compound was prepared following a procedure analogous to that described in Example 1 using (S)-6-(2-hydroxy-2-methylpropyl)-6-phenyl-3-((S)-pyrrolidin-3-yl)-1,3-oxazinan-2-one and 2,5-dichloropyrimidine at 150° C. for 20 min. LC-MS Method 1 $t_R$=1.51 min, m/z=431,433(M+1); $^1$H NMR ($CD_3OD$) 8.24(s, 2H), 7.41-7.27(m, 5H), 4.78 (m, 1H), 3.71-3.57(m, 2H), 2.73(m, 1H), 2.52(m, 2H), 2.17(s, 2H), 1.24(s, 3H), 0.93(s, 3H).

EXAMPLE 15

(S)-6-(2-hydroxy-2-methylpropyl)-6-phenyl-3-((S)-1-(5-(trifluoromethyl)pyridin-2-yl)pyrrolidin-3-yl)-1,3-oxazinan-2-one

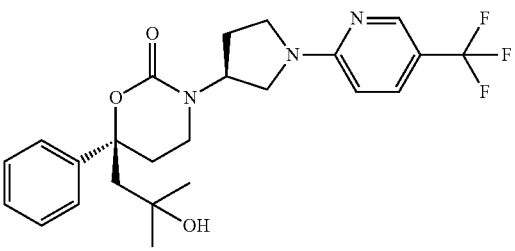

The title compound was prepared following a procedure analogous to that described in Example 1 using (S)-6-(2-hydroxy-2-methylpropyl)-6-phenyl-3-((S)-pyrrolidin-3-yl)-1,3-oxazinan-2-one and 2-fluoro-5-trifluoromethylpyridine at 150° C. for 20 min. LC-MS Method 1 $t_R$=1.51 min, m/z=464(M+1); $^1$H NMR ($CD_3OD$) 8.26(s, 1H), 8.00(d, 1H), 7.38(m, 4H), 7.29(m, 1H), 7.01(m, 1H), 4.74(m, 1H), 3.77(m, 2H), 3.58(q, 1H), 3.47(m, 1H), 2.83(m, 1H), 2.55(m, 2H), 2.18(s, 2H), 1.24(s, 3H), 0.94(s, 3H).

EXAMPLE 16

4108.1002-007 EXAMPLE 508

(R)-6-(4-fluorophenyl)-6-(3-hydroxypropyl)-3-((S)-1-(5-(trifluoromethyl)pyridin-2-yl)piperidin-3-yl)-1,3-oxazinan-2-one

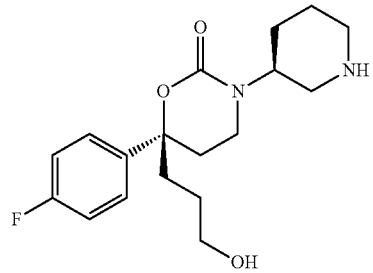

+

A mixture of (R)-6-(4-fluorophenyl)-6-(3-hydroxypropyl)-3-((S)-piperidin-3-yl)-1,3-oxazinan-2-one (100 mg, 0.30 mmol), 2-bromo-5-(trifluoromethyl)pyridine (67 mg, 0.36 mmol), and triethylamine (91 mg, 0.90 mmol) in acetonitrile was heated to reflux for 3 h. The reaction mixture was concentrated. The residue was purified by preparative TLC and preparative HPLC to afford (R)-6-(4-fluorophenyl)-6-(3-hydroxypropyl)-3-((S)-1-(5-(trifluoromethyl)pyridin-2-yl)piperidin-3-yl)-1,3-oxazinan-2-one (10.09 mg, 7%). LC-MS Method 2 $t_R$=1.34 min, m/z=482. $^1$H NMR (400MHz, CDCl$_3$): 1.28 (m, 1H), 1.64 (m, 2H), 1.76 (m, 3H), 1.92 (m, 2H), 2.18 (m, 1H), 2.27 (m, 1H), 2.77 (m, 3H), 3.21 (m, 1H), 3.52 (t, 2H), 3.83 (broad, 1H), 4.11 (d, 1H), 4.25 (d, 1H), 6.57 (d, 1H), 7.03 (t, 2H), 7.23 (m, 2H), 7.54 (d, 1H), 8.29 (s, 1H).

EXAMPLE 17

4108.1002-007 EXAMPLE 611

6((S)-3-((R)-6-(4-fluorophenyl)-6-(3-hydroxypropyl)-2-oxo-1,3-oxazinan-3-yl)piperidin-1-yl)nicotinonitrile

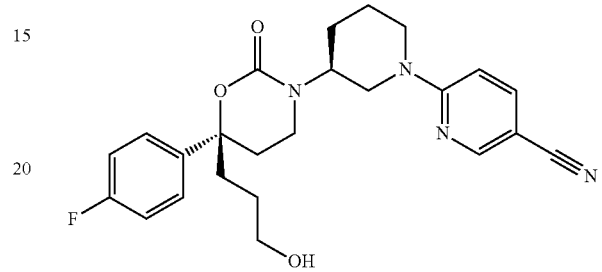

The title compound was prepared from (R)-6-(4-fluorophenyl)-6-(3-hydroxypropyl)-3-((S)-piperidin-3-yl)-1,3-oxazinan-2-one and 2-bromo-5-cyanopyridine following a procedure analogous to that described in Example 16. LC-MS Method 2 $t_R$=1.218 min, m/z=439.1; $^1$H NMR (CDCl$_3$) 1.21-1.36 (m, 1H), 1.62 (m, 1H), 1.78 (m, 3H), 1.56 (m, 2H), 1.86-2.00 (m, 2H), 2.19 (m, 1H), 2.29 (m, 1H), 2.67-2.86 (m, 3), 3.20 (m, 1H), 3.50 (t, 2H), 3.79 (m, 1H), 4.12 (m, 1H), 4.30 (d, 1H), 6.53 (m, 1H), 7.01 (t, 2H), 7.24 (m, 2H), 7.51 (d, 1H), 8.30 (s, 1H).

EXAMPLE 18

4108.1002-007 EXAMPLE 584

6-((S)-3-((R)-6-(4-fluorophenyl)-6-(3-hydroxypropyl)-2-oxo-1,3-oxazinan-3-yl)piperidin-1-yl)nicotinamide

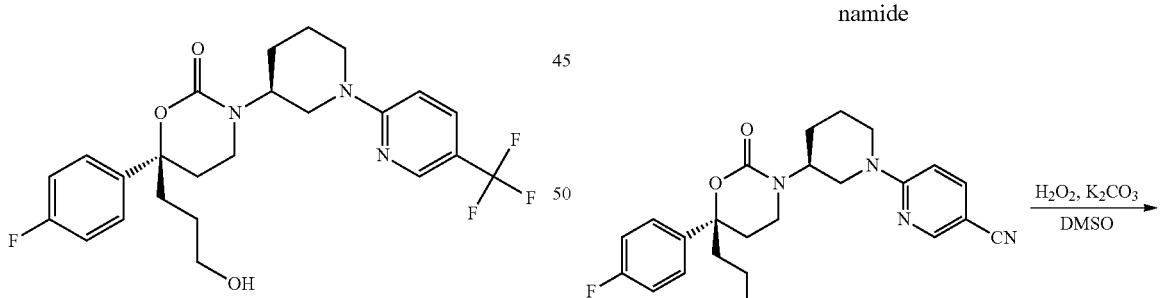

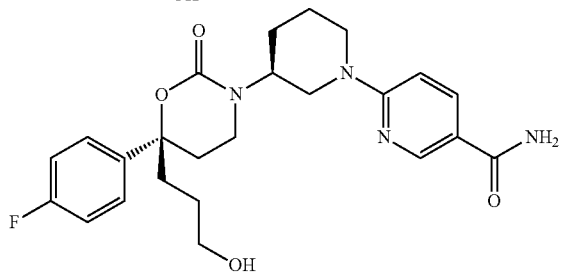

To a solution of 6-((S)-3-((R)-6-(4-fluorophenyl)-6-(3-hydroxypropyl)-2-oxo-1,3-oxazinan-3-yl)piperidin-1-yl)nicotinonitrile (520 mg, 1.19 mmol) in DMSO (10 mL) was added $H_2O_2$ (30%, 1 mL) and $K_2CO_3$ (82 mg, 0.59 mmol). The mixture was stirred at rt for 1 d. After water and EtOAc were added, the mixture was extracted with EtOAc. The organic layers were dried and concentrated to give 6-((S)-3-((R)-6-(4-fluorophenyl)-6-(3-hydroxypropyl)-2-oxo-1,3-oxazinan-3-yl)piperidin-1-yl)nicotinamide (430 mg, 79%). LC-MS Method 2 $t_R$=0.99 min, m/z=457. $^1$H NMR (400 MHz, $CDCl_3$): 1.29-1.30 (m, 1H), 1.58-1.63 (m, 2H), 1.82-1.86 (m, 2H), 1.91-2.00 (m, 3H), 2.21-2.32 (m, 1H), 2.49-2.52 (m, 1H), 2.65-2.71 (m, 1H), 2.81-2.96 (m, 3H), 3.39 (m, 1H), 3.42-4.48 (m, 2H), 3.87(m, 1H), 4.21-4.24 (m, 1H), 4.30 (s, 1H), 6.75-6.78 (d, 1H), 7.39-7.72 (t, 2H), 7.94-7.97 (m,1H), 8.59-8.60 (s, 1H).

EXAMPLE 19

4108.1002-007 EXAMPLE 596

6-((S)-3-((R)-6-(4-fluorophenyl)-6-(3-hydroxypropyl)-2-oxo-1,3-oxazinan-3-yl)piperidin-1-yl)-N-methylnicotinamide

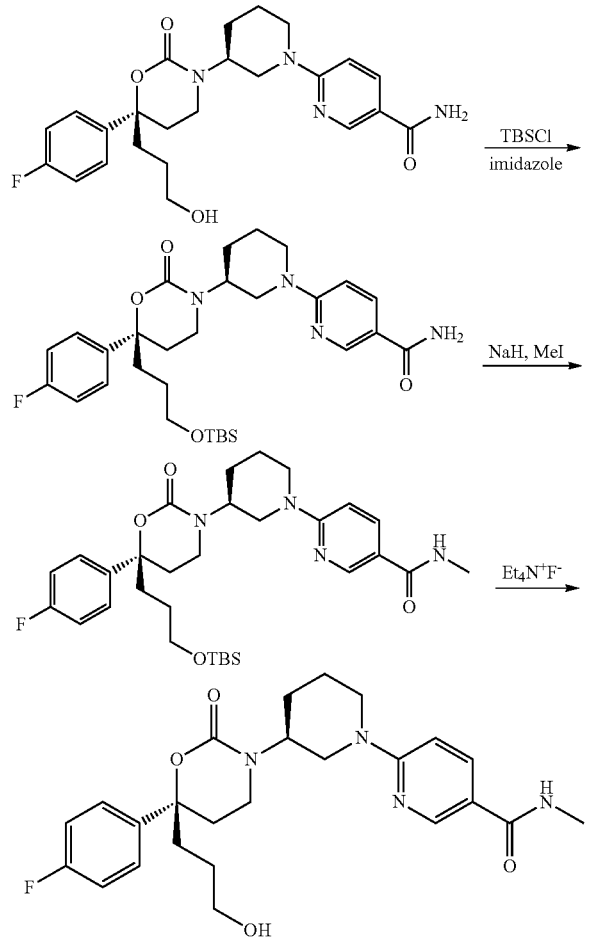

The title compound was prepared from 6-((S)-3-((R)-6-(4-fluorophenyl)-6-(3-hydroxypropyl)-2-oxo-1,3-oxazinan-3-yl)piperidin-1-yl)nicotinamide following the steps indicated in the scheme immediately above. LC-MS Method 2 $t_R$=0.96, m/z=471.1; $^1$H NMR ($CDCl_3$) 0.83 (m, 1H), 1.20-1.33 (m, 2H), 1.58 (m, 1H), 1.70-1.81 (m, 3H), 1.83-2.00 (m, 2H), 2.18 (m, 1H), 2.28 (m, 1H), 2.68 (m, 1H), 2.79 (m, 2H), 2.91 (d, 3H), 34.20 (m, 1H), 3.51 (t, 2H), 3.84 (m, 1H), 4.12 (m, 1H), 4.24 (m, 1H), 6.00 (m, 1H), 6.52 (d, 1H), 7.02 (t, 2H), 7.25 (m, 2H), 7.80 (dd, 1H), 8.42 (d, 1H).

EXAMPLE 20

4108.1002-007 EXAMPLE 600

6-((S)-3-((R)-6-(4-fluorophenyl)-6-(3-hydroxpropyl)-2-oxo-1,3-oxazinan-3-yl)piperidin-1-yl)-N,N-dimethylnicotinamide

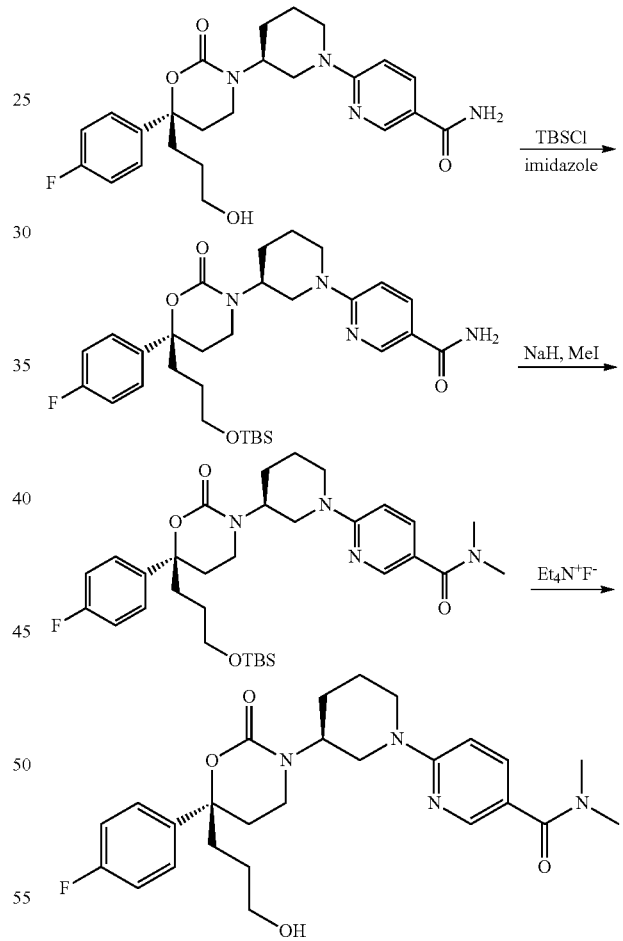

The title compound was prepared from 6-((S)-3-((R)-6-(4-fluorophenyl)-6-(3-hydroxypropyl)-2-oxo-1,3-oxazinan-3-yl)piperidin-1-yl)nicotinamide following the steps indicated in the scheme immediately above. LC-MS Method 2 $t_R$=1.012, m/z=485.1; $^1$H NMR ($CDCl_3$) 0.79 (m, 1H), 1.19 (m, 2H), 1.76 (m, 3H), 1.92 (m, 2H), 2.17 (m, 1H), 2.28 (m, 1H), 2.68 (m, 1H), 2.79 (m, 2H), 3.00 (s, 6H), 3.20 (m, 1H), 3.51 (t, 2H), 3.84 (m, 1H), 4.12 (dd, 1H), 4.24 (m, 1H), 6.52 (d, 1H), 7.02 (t, 2H), 7.22 (m, 2H), 7.53 (dd, 1H), 8.19 (d, 1H).

EXAMPLE 21

N-tert-butyl-2-((S)-3-((S)-6-(2-hydroxy-2-methyl-propyl)-2-oxo-6-phenyl-1,3-oxazinan-3-yl)piperidin-1-yl)thiazole-5-carboxamide

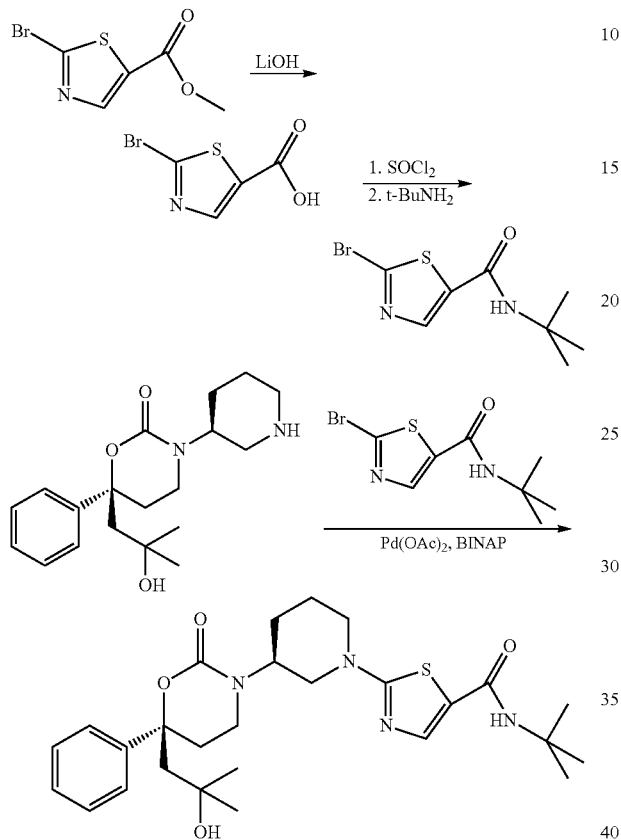

The title compound was prepared from (S)-6-(2-hydroxy-2-methylpropyl)-6-phenyl-3-((S)-piperidin-3-yl)-1,3-oxazinan-2-one and 2-bromo-N-tert-butylthiazole-5-carboxamide following a procedure analogous to that described in Example 13. LC-MS Method 2 $t_R$=1.23 min, m/z=515.

EXAMPLE 22

(S)-3-((S)-1-(5-chloro-6-methylpyridazin-3-yl)piperidin-3-yl)-6-(2-hydroxy-2-methylpropyl)-6-phenyl-1,3-oxazinan-2-one

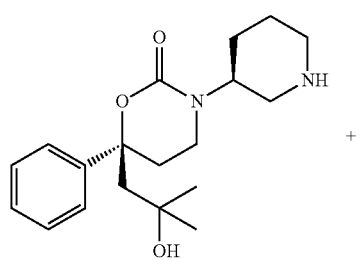

+

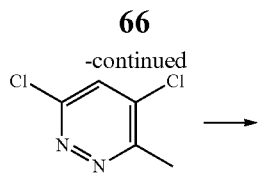

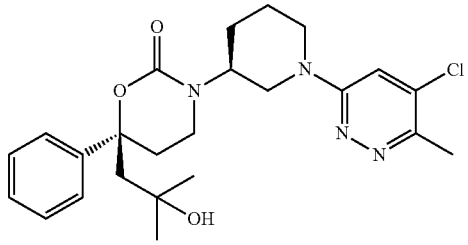

The title compound was prepared from (S)-6-(2-hydroxy-2-methylpropyl)-6-phenyl-3-((S)-piperidin-3-yl)-1,3-oxazinan-2-one and 4,6-dichloro-3-methylpyridazine following a procedure analogous to that described in Example 1. LC-MS Method 1 $t_R$=1.37 min, m/z=459, 461(M+1).

4,6-dichloro-3-methylpyridazine was prepared following the procedure described in WO 2003/041712 (Intermediate A3, p 12).

EXAMPLE 23

(S)-6-(2-hydroxy-2-methylpropyl)-6-phenyl-3-((S)-1-(4-(trifluoromethyl)pyrimidin-2-yl)pyrrolidin-3-yl)-1,3-oxazinan-2-one

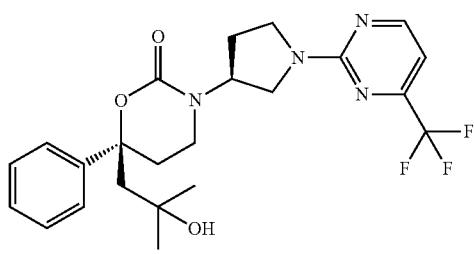

The title compound was prepared from (S)-6-(2-hydroxy-2-methylpropyl)-6-phenyl-3-((S)-pyrrolidin-3-yl)-1,3-oxazinan-2-one and 2-chloro-4-(trifluoromethyl)pyrimidine following a procedure analogous to that described in Example 1 heating at 150° C. for 20 min. LC-MS Method 1 $t_R$=1.66 min. min, m/z=465(M+1); $^1$H NMR (CD$_3$OD) 8.51(d, 1H), 7.36(m, 4H), 7.28(m, 1H), 6.86(d, 1H), 4.81(m, 1H), 3.73(m, 1H), 3.66(m, 1H), 3.51(q, 1H), 2.75(m, 1H), 2.51(m, 2H), 2.22(m, 2H), 2.19(s, 2H), 1.25(s, 3H), 0.94(s, 3H).

EXAMPLE 24

(S)-6-(2-hydroxy-2-methylpropyl)-3-((S)-1-(5-methoxypyrimidin-2-yl)pyrrolidin-3-yl)-6-phenyl-1,3-oxazinan-2-one

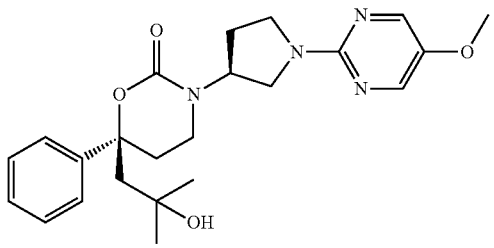

The title compound was prepared from (S)-6-(2-hydroxy-2-methylpropyl)-6-phenyl-3-((S)-pyrrolidin-3-yl)-1,3-oxazinan-2-one and 2-chloro-5-methoxypyrimidine following a procedure analogous to that described in Example 1 heating at 150° C. for 20 min. LC-MS Method 1 $t_R$=1.27 min. min, m/z=427(M+1); $^1$H NMR (CD$_3$OD) 8.17(d, 2H), 7.37(m, 5H), 4.79(m, 1H), 3.82(s, 3H), 3.67(m, 2H), 3.49(m, 1H), 3.78(m, 1H), 2.52(m, 2H), 2.24(m, 2H), 2.18(s, 2H), 1.24(s, 3H), 0.94(s, 3H).

BIOLOGICAL TEST EXAMPLE 1

The inhibition of a microsomal preparation of 11β-HSD1 by compounds of the invention was measured essentially as previously described (K. Solly, S. S. Mundt, H. J. Zokian, G. J. Ding, A. Hermanowski-Vosatka, B. Strulovici, and W. Zheng, High-Throughput Screening of 11-Beta-Hydroxyseroid Dehydrogenase Type 1 in Scintillation Proximity Assay Format. Assay Drug Dev Technol 3 (2005) 377-384). All reactions were carried out at rt in 96 well clear flexible PET Microbeta plates (PerkinElmer). The assay begins by dispensing 49 µl of substrate solution (50 mM HEPES, pH 7.4, 100 mM KCl, 5 mM NaCl, 2 mM MgCl$_2$, 2 mM NADPH and 160 nM [$^3$H]cortisone (1 Ci/mmol)) and mixing in 1 µL of the test compounds in DMSO previously diluted in half-log increments (8 points) starting at 0.1 mM. After a 10 minute pre-incubation, 50 µL of enzyme solution containing microsomes isolated from CHO cells overexpressing human 11β-HSD1 (10-20 µg/ml of total protein) was added, and the plates were incubated for 90 minutes at rt. The reaction was stopped by adding 50 µl of the SPA beads suspension containing 10 µM 18β-glycyrrhetinic acid, 5 mg/ml protein A coated YSi SPA beads (GE Healthcare) and 3.3 µg/ml of anti-cortisol antibody (East Coast Biologics) in Superblock buffer (Bio-Rad). The plates were shaken for 120 minutes at rt, and the SPA signal corresponding to [$^3$H]cortisol was measured on a Microbeta plate reader.

BIOLOGICAL TEST EXAMPLE 2

The inhibition of 11β-HSD1 by compounds of this invention was measured in whole cells as follows. Cells for the assay were obtained from two sources: fully differentiated human omental adipocytes from Zen-Bio, Inc.; and human omental pre-adipocytes from Lonza Group Ltd. Pre-differentiated omental adipocytes from Zen-Bio Inc. were purchased in 96-well plates and were used in the assay at least two weeks after differentiation from precursor preadipocytes. Zen-Bio induced differentiation of pre-adipocytes by supplementing medium with adipogenic and lipogenic hormones (human insulin, dexamethasone, isobutylmethylxanthine and PPAR-gamma agonist). The cells were maintained in full adipocyte medium (DMEM/Ham's F-12 (1:1, v/v), HEPES pH 7.4, fetal bovine serum, penicillin, streptomycin and Amphotericin B, supplied by Zen-Bio, Inc.) at 37° C., 5% CO$_2$.

Pre-adipocytes were purchased from Lonza Group Ltd. and placed in culture in Preadipocyte Growth Medium-2 supplemented with fetal bovine serum, penicillin, and streptomycin (supplied by Lonza) at 37° C., 5% CO$_2$. Pre-adipocytes were differentiated by the addition of insulin, dexamethasone, indomethacin and isobutyl-methylxanthine (supplied by Lonza) to the Preadipocyte Growth Medium-2. Cells were exposed to the differentiating factors for 7 days, at which point the cells were differentiated and ready for the assay. One day before running the assay, the differentiated omental adipocytes were transferred into serum- and phenol-red-free medium for overnight incubation. The assay was performed in a total volume of 200 µL. The cells were pre-incubated with serum-free, phenol-red-free medium containing 0.1% (v/v) of DMSO and various concentrations of the test compounds at least 1 h before [$^3$H] cortisone in ethanol (50 Ci/mmol, ARC, Inc.) was added to achieve a final concentration of cortisone of 100 nM. The cells were incubated for 3-4 hrs at 37° C., 5% CO$_2$. Negative controls were incubated without radioactive substrate and received the same amount of [$^3$H] cortisone at the end of the incubation. Formation of [$^3$H] cortisol was monitored by analyzing 25 µL of each supernatant in a scintillation proximity assay (SPA). (Solly, K.; Mundt, S. S.; Zokian, H. J.; Ding, G. J.; Hermanowski-Vosatka, A.; Strulovici, B.; Zheng, W. Assay Drug Dev. Technol. 2005, 3, 377-384). Many compounds of the invention showed significant activity in this assay.

| TABLE OF BIOLOGICAL ASSAY RESULTS | | |
|---|---|---|
| | Biological Test Example 1 | |
| Compound | IC$_{50}$ Range$^a$ | Average % inhibition at 100 nM |
| EXAMPLE 1 | ++ | 85.5 |
| EXAMPLE 2 | ++ | 77.8 |
| EXAMPLE 3 | ++ | 91.3 |
| EXAMPLE 4 | ++ | 89.8 |
| EXAMPLE 5 | ++ | 86.0 |
| EXAMPLE 6 | ++ | 83.0 |
| EXAMPLE 7 | ++ | 89.5 |
| EXAMPLE 8 | ++ | 91.3 |
| EXAMPLE 9 | ++ | 40.2 |
| EXAMPLE 10 | ++ | 85.8 |
| EXAMPLE 11 | ++ | 75.3 |
| EXAMPLE 12 | ++ | 91.7 |
| EXAMPLE 13 | ++ | 90.4 |
| EXAMPLE 14 | ++ | 93.8 |
| EXAMPLE 15 | ++ | 92.2 |
| EXAMPLE 16 | ++ | 94.9 |
| EXAMPLE 17 | ++ | 94.7 |
| EXAMPLE 18 | ++ | 81.6 |
| EXAMPLE 19 | ++ | 55.2 |
| EXAMPLE 20 | ++ | 72.5 |
| EXAMPLE 21 | +190 | 27.3 |
| EXAMPLE 22 | +190 | 20.9 |

-continued

TABLE OF BIOLOGICAL ASSAY RESULTS

| | Biological Test Example 1 | |
|---|---|---|
| Compound | IC$_{50}$ Range$^a$ | Average % inhibition at 100 nM |
| EXAMPLE 23 | ++ | 94.1 |
| EXAMPLE 24 | ++ | 67.8 |

$^a$++ means IC$_{50}$ = <100 nM, + means IC$_{50}$ = 100 – 1000 nM, # means IC$_{50}$ >100 nM, – means IC$_{50}$ >1000 nM.

BIOLOGICAL TEST EXAMPLE 4

The inhibition of a microsomal preparation of 11β-HSD1 in the presence of 50% human plasma by compounds of the invention was measured as follows. Microsomes from CHO cells overexpressing human 11β-HSD1 were diluted into reaction buffer consisting of 25 mM HEPES, pH 7.4, 50 mM KCl, 2.5 mM NaCl, 1 mM MgCl2, and 50% (v/v) human plasma (BioChemed). The assay began by dispensing 49 µl of microsome solution into 96-well polypropylene plates and adding 1 µl of the test compounds in DMSO, previously diluted in half-log increments (8 points) starting at 1.0 mM. The reaction was initiated with the addition of 50 µl substrate solution consisting of reaction buffer with 2 mM NADPH and 160 nM [$^3$-H]cortisone (1 Ci/mmol). The plates were incubated for 120 minutes at rt, and the reaction was quenched with the addition of 100 µl acetonitrile with 20 mM cortisone and 20 mM cortisol. After a ten minute incubation at rt, 100 µl of each well was filtered through a MultiScreen HTS, HV filter plate (Millipore) and diluted with 100 µl of reaction buffer without human plasma. [$^3$-H]cortisone and [$^3$-H]cortisol were separated by HPLC on a Zorbax SB-C8 column (4.6×250 mm, Agilent) with an isocratic elution at 25% acetonitrile in water with 0.01% trifluoroacetic acid, and radioactivity was quantified with an in-line β-RAM (IN/US Systems, Inc.).

BIOLOGICAL TEST EXAMPLE 3

In vitro inhibition of 11 β-HSD1 by test compounds was determined with HTRF (Homogeneous Time-Resolved Fluorescence) technology (cisbio international, France) detecting cortisol generated from cortisterone by human liver microsomes. Briefly, compounds were incubated for 1 hour at 37° C. in Tris buffer (20 mM tris, 5 mM EDTA, pH 6.0) containing NADPH (200 µM) and cortisone (80 nM). Cortisol generated in the reaction was then detected with a competitive immunoassay, involving two HTRF conjugates: cortisol linked to XL665 and anti-cortisol antibody labeled with Europium cryptate. The incubation period for detection reaction was typically 2 hours. The amount of cortisol was determined by reading the time-resolved fluorescence of the wells (Ex 320/75 nm; Em 615/8.5 nm and 665/7.5 nm). The ratio of the two emission signals was then calculated (Em665*10000/Em615). Each assay contained incubations with vehicle controls instead of compound as controls for non-inhibited cortisol generation (100% CTL; 'high values') and incubations with carbenoxolone as controls for fully inhibited enzyme and cortisol background (0% CTL; 'low values'). Each assay also contained a calibration curve with cortisol to transform the fluorescent data into cortisol concentrations. Percent inhibition of each compound was determined relative to the carbenoxolone signal.

BIOLOGICAL TEST EXAMPLE 4

The inhibition of a microsomal preparation of 11β-HSD1 in the presence of 50% human plasma by compounds of the invention was measured as follows. Microsomes from CHO cells overexpressing human 11β-HSD1 were diluted into reaction buffer consisting of 25 mM HEPES, pH 7.4, 50 mM KCl, 2.5 mM NaCl, 1 mM MgCl2, and 50% (v/v) human plasma (BioChemed). The assay began by dispensing 49 µl of microsome solution into 96-well polypropylene plates and adding 1 µl of the test compounds in DMSO, previously diluted in half-log increments (8 points) starting at 1.0 mM. The reaction was initiated with the addition of 50 µl substrate solution consisting of reaction buffer with 2 mM NADPH and 160 nM [$^3$-H]cortisone (1 Ci/mmol). The plates were incubated for 120 minutes at rt, and the reaction was quenched with the addition of 100 µl acetonitrile with 20 mM cortisone and 20 mM cortisol. After a ten minute incubation at rt, 100 µl of each well was filtered through a MultiScreen HTS, HV filter plate (Millipore) and diluted with 100 µl of reaction buffer without human plasma. [$^3$-H]cortisone and [$^3$-H]cortisol were separated by HPLC on a Zorbax SB-C8 column (4.6×250 mm, Agilent) with an isocratic elution at 25% acetonitrile in water with 0.01% trifluoroacetic acid, and radioactivity was quantified with an in-line 8-RAM (IN/US Systems, Inc.).

BIOLOGICAL TEST EXAMPLE 5

Fraction Unbound in Human Plasma

Plasma protein binding of compounds was determined with Equilibrium Dialysis of spiked plasma against compound free dextrane buffer using a dialysis membrane with mass cutoff of 5000 Da. Compound concentrations in plasma and buffer after incubation were measured using HPLC/Mass spectrometry.

BIOLOGICAL TEST EXAMPLE 6

CYP3A4 Inhibition

The assay was based on a method published by Moody et al. (Xenobiotica 1999). The inhibition of cytochrome P450 3A4-isoenzyme catalysed N-demethylation of [N-methyl-14C]-Erythromycin by the test compound was assayed at 37° C. with human recombinant cytochrome P450 3A4. All assays were carried out on a robotic system in 96 well plates. The final incubation volume of 200 µl contains TRIS buffer (0.1 M), MgCl$_2$ (5 mM), recombinant protein (40 pmol/ml), Erythromycin (50 µM) and the test compound either at four different concentrations in duplicate (e.g. highest concentration 10-50 µM with subsequent serial 1:5 dilutions) or at a concentration of 10 µM in triplicate. Following a short pre-incubation period, reactions were started with the cofactor (NADPH, 1 mM) and stopped by addition of 50 µl aqueous trichloroacetic acid (10%;w/v). An aliquot of the incubate was transferred to 96 well solid phase extraction (SPE) plates and extracted on the cartridge. The resultant [$^{14}$C]-formaldehyde/formic acid was not retained on the cartridge and was therefore separated from the unmetabolized substrate by washing the SPE plates with water. An aliquot of the eluates was transferred into well plates suitable for liquid scintillation counting. The rate of formation of [$^{14}$C]-formaldehyde/formic acid in these incubations was compared to a control activity containing no test compound. If the compound was tested at four concentrations, experimental $IC_{50}$ values were calculated.

BIOLOGICAL TEST EXAMPLE 7

CYP2C9 Inhibition

Using a procedure similar to that described in Biological Test Example 6, the inhibition of cytochrome P450 2C9-isoenzyme catalysed 0-demethylation of [O-methyl-$^{14}$C]-Naproxen by the test compound was assayed at 37° C. with human recombinant cytochrome P450 2C9. The experimental $IC_{50}$ was calculated based on % control at four different concentrations.

BIOLOGICAL TEST EXAMPLE 8

CYP2C19 Inhibition

Using a procedure similar to that described in Biological Test Example 6, the inhibition of cytochrome P450 2C19-isoenzyme catalysed N-demethylation of [N-methyl-$^{14}$C]-Diazepam by the test compound was assayed at 37° C. with human recombinant cytochrome P450 2C19. The experimental $IC_{50}$ was calculated based on % control at four different concentrations.

BIOLOGICAL TEST EXAMPLE 9

CYP2C9 Inhibition

The inhibition of recombinant CYP2C9 by compounds of the invention was measured using a commercial kit from Invitrogen (cat #2859). Supplied microsomes isolated from insect cells infected with a baculovirus engineered to express human CYP2C9 were diluted to 10 mM in reaction buffer (100 mM potassium phosphate buffer, pH 8.0) with an NADPH generation system (3.33 mM glucose-6-phosphate and 0.4 U/ml glucose-6-phosphate dehydrogenase). 89 µl of this dilution were dispensed to each well of a 96-well, black, polystyrene plate and mixed with 1 µl of test compound previously diluted in DMSO in half log increments starting at 3 mM. The assay was initiated by adding 10 µl of fluorogenic substrate n-octyloxymethylresorufin (OOMR, 20 µM.) with NADP (100 µM) diluted in reaction buffer. The plate was immediately placed in a Perkin Elmer Fusion plate reader. Reaction progress was monitored by measuring fluorescence every two minutes for a total of twenty minutes (530 nM excitation filter/605 nM emission filter).

TABLE OF BIOLOGICAL ASSAY RESULTS FOR BIOLOGICAL TESTS 1, 4 AND 5

| EXAMPLE | Biological Test Example 1 $IC_{50}$ (nM) | Biological Test Example 4[a] $IC_{50}$ (nM) | Shift[b] | Biological Test Example 5 (%) |
|---|---|---|---|---|
| 1 | 12.7 | nt | | |
| 2 | 22.6 | 209.6 | 9.3 | |
| 3 | 4.4 | 68.7 | 15.6 | |
| 4 | 4.1 | 21.6 | 5.3 | |
| 5 | 11.8 | nt | | |
| 6 | 9.0 | 67.2 | 7.5 | |
| 7 | 6.1 | 14.8 | 2.4 | |
| 8 | 1.7 | 14.6 | 8.6 | |
| 9 | 84.3 | nt | | |
| 10 | 5.5 | 69.2 | 12.7 | |
| 11 | 19.1 | nt | | |
| 12 | 4.3 | 10.4 | 2.4 | |
| 13 | 13.5 | nt | | |
| 14 | 3.5 | 7.8 | 2.2 | |
| 15 | 4.3 | 37.6 | 8.7 | |
| 16 | 1.4 | 14.4 | 10.0 | |
| 18 | 26.4 | nt | | |
| 19 | 65.6 | nt | | |
| 20 | 27.4 | nt | | |
| 21 | >100 | nt | | |
| 22 | >100 | nt | | |
| 23 | 5.8 | 52.8 | 9.2 | |
| 24 | 42.3 | nt | | |

TABLE OF BIOLOGICAL ASSAY RESULTS FOR COMPARATOR COMPOUNDS IN BIOLOGICAL TESTS 1, 4 AND 5

| Comparator Compound | Biological Test Example 1 $IC_{50}$ (nM) | Biological Test Example 4a $IC_{50}$ (nM) | Shift[b] | Biological Test Example 5 (%) |
|---|---|---|---|---|
| 1 | 0.77 | 11.97 | 15.51 | |
| 2 | 1.80 | 14.16 | 7.88 | |
| 3 | 0.75 | 17.74 | 23.63 | 0.3 |
| 4 | 1.44 | 15.24 | 10.57 | |

-continued

TABLE OF BIOLOGICAL ASSAY RESULTS FOR COMPARATOR COMPOUNDS IN BIOLOGICAL TESTS 1, 4 AND 5

| Comparator Compound | Biological Test Example 1 $IC_{50}$ (nM) | Biological Test Example 4a $IC_{50}$ (nM) | Shift[b] | Biological Test Example 5 (%) |
|---|---|---|---|---|
| 5 | 0.51 | 18.50 | 36.10 | |
| 6 | 1.48 | 37.58 | 25.39 | |
| 7 | 0.99 | 41.90 | 42.43 | |
| 8 | 0.72 | 17.85 | 24.74 | |
| 9 | 0.55 | 11.86 | 21.45 | 0.3 |
| 10 | 1.79 | 53.49 | 29.91 | |
| 11 | 0.55 | 13.40 | 24.59 | 0.7 |
| 12 | 1.08 | 19.54 | 18.12 | 0.4 |
| 13 | 0.76 | 6.32 | 8.30 | |
| 14 | 1.30 | 8.94 | 6.90 | |
| 15 | 0.79 | 8.94 | 11.32 | |

[a]nt means not tested; [b]Shift is the $IC_{50}$ determined in Biological Test Example 4 divided by the 1050 determined in Biological Test Example 1.

TABLE OF BIOLOGICAL ASSAY RESULTS FOR COMPARATOR COMPOUNDS IN BIOLOGICAL TESTS 6-9

| Comparator Compound | Biological Test Example 6 CYP3A4, $IC_{50}$ [μM] | Biological Test Example 7 CYP2C9, $IC_{50}$ [μM] | Biological Test Example 8 CYP2C19, $IC_{50}$ [μM] | Biological Test Example 9 CYP2C9 $IC_{50}$ [μM] |
|---|---|---|---|---|
| 1 | | | | 27.0 |
| 2 | | | | 1.4 |
| 3 | 7.4 | 4.1 | 5.7 | 4.9 |
| 4 | | | | 5.1 |
| 5 | 9.9 | 5.1 | 8.3 | 3.7 |
| 6 | 4.4 | 2.3 | 8.6 | 5.0 |
| 7 | | | | 4.0 |
| 8 | 5.3 | 2.4 | 5.6 | 3.0 |
| 9 | 7.0 | 3.1 | 9.3 | 2.5 |
| 10 | | | | 3.6 |
| 11 | 14.1 | 6.3 | 12.5 | 5.5 |
| 12 | 4.9 | 4.6 | 9.5 | 2.5 |
| 12 | 4.9 | 3.9 | 10.1 | |
| 13 | 4.4 | 5.6 | <0.4 | 7.3 |
| 14 | 19.7 | 25.9 | 6.4 | 24.6 |
| 15 | 3.1 | 7.7 | <0.4 | 9.5 |

Comparator 1

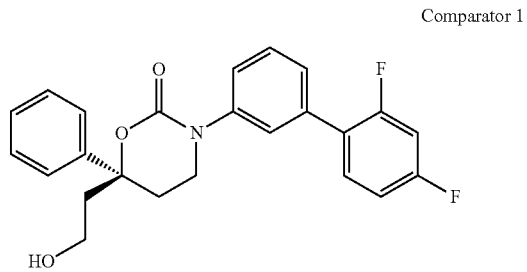

Comparator 2

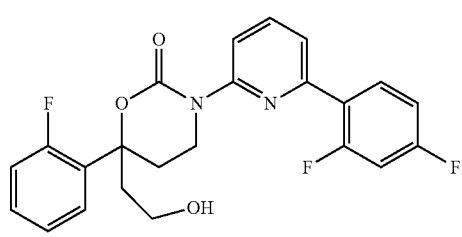

Comparator 3

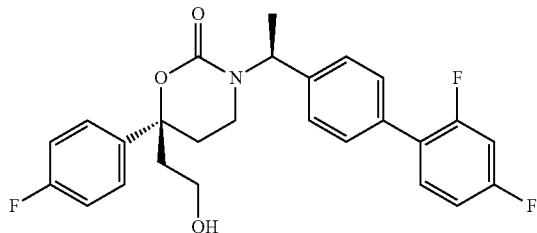

Comparator 4

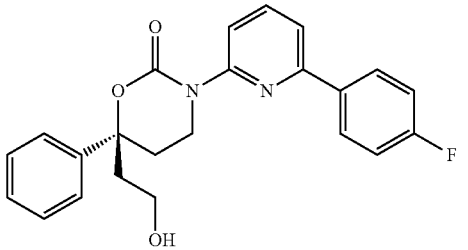

Comparator 5

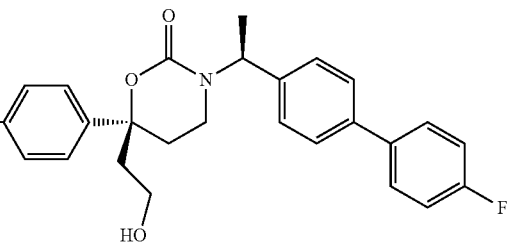

Comparator 6

Comparator 7
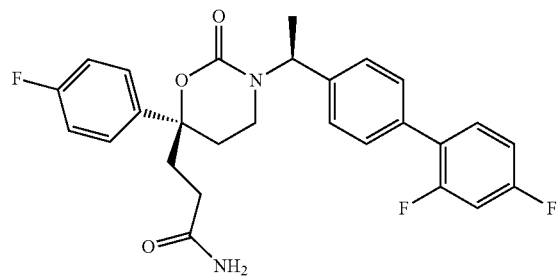

Comparator 8
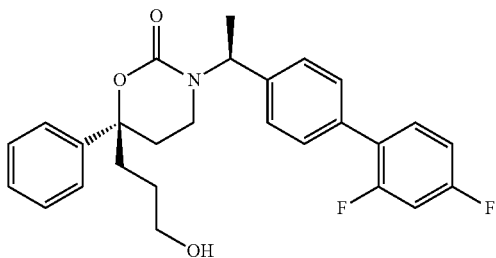

Comparator 9
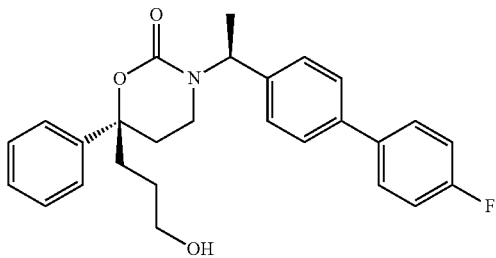

Comparator 10
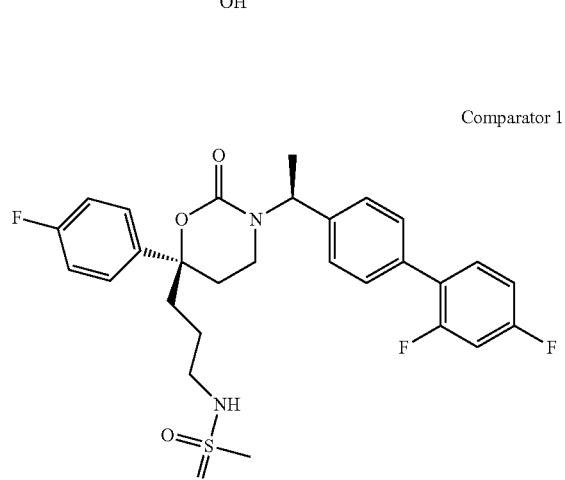

Comparator 11
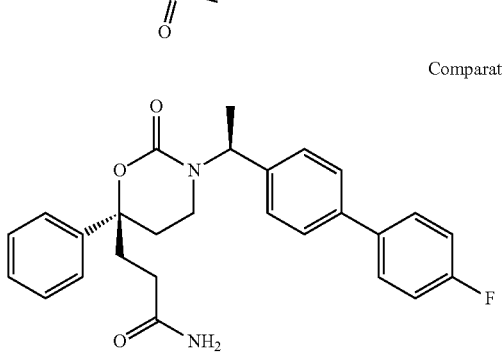

Comparator 12
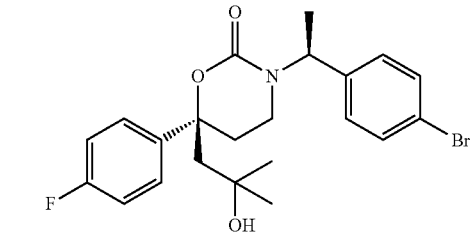

Comparator 13
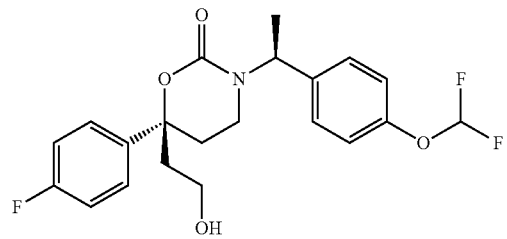

Comparator 14
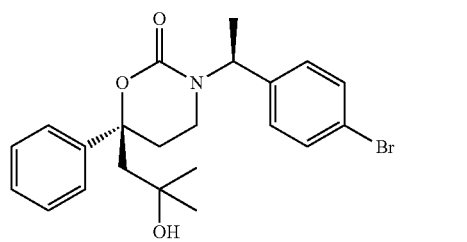

Comparator 15
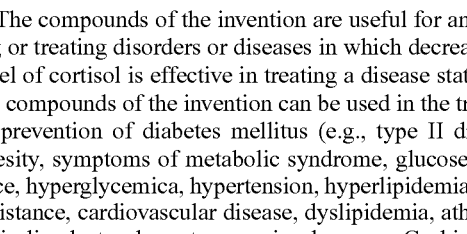

The compounds of the invention are useful for ameliorating or treating disorders or diseases in which decreasing the level of cortisol is effective in treating a disease state. Thus, the compounds of the invention can be used in the treatment or prevention of diabetes mellitus (e.g., type II diabetes), obesity, symptoms of metabolic syndrome, glucose intolerance, hyperglycemica, hypertension, hyperlipidemia, insulin resistance, cardiovascular disease, dyslipidemia, atherosclerosis, lipodystrophy, osteoporosis, glaucoma, Cushing's syndrome, Addison's Disease, visceral fat obesity associated with glucocorticoid therapy, depression, anxiety, Alzheimer's disease, dementia, cognitive decline (including age-related cognitive decline), polycystic ovarian syndrome, infertility and hypergonadism. The compounds of the invention can be used as therapeutic agents for pseudo Cushing's Syndrome associated with alcoholic liver disease. In addition, the compounds modulate the function of B and T cells of the immune system and can therefore be used to treat diseases such as tuberculosis, leprosy and psoriasis. They can also be used to promote wound healing, particularly in diabetic patients.

Additional diseases or disorders that are related to 11β-HSD1 activity include those selected from the group consisting of lipid disorders, hypretriglyceridemia, hypercholesterolemia, low HDL levels, high LDL levels, vascular restenosis, pancreatitis, abdominal obesity, neurodegenerative disease, retinopathy, nephropathy, neuropathy, diabetes, coronary heart disease, stroke, peripheral vascular disease, Cushing's syndrome, hyperinsulinemia, viral diseases, and Syndrome X. A further disease related to 11β-HSD1 activity is pseudo Cushing's Syndrome associated with alcoholic liver disease.

A pharmaceutical composition of the invention may, alternatively or in addition to an 11β-HSD1 inhibitor of the invention, comprise a pharmaceutically acceptable salt of a an 11β-HSD1 inhibitor of the invention and one or more pharmaceutically acceptable carriers therefore. Alternatively, a pharmaceutical composition of the invention may comprise a compound of an 11β-HSD1 inhibitor of the invention or a pharmaceutical salt thereof as the only pharmaceutically active agent in the pharmaceutical composition. The disclosed 11β-HSD1 inhibitors can be used alone or in a combination therapy with one or more additional agents for the treatment of diabetes, dyslipidemia, cardiovascular disease, hypertension, obesity, cancer or glaucoma.

The compositions of the invention are 11β-HSD1 inhibitors. Said compositions contain compounds having a mean inhibition constant ($IC_{50}$) against 11β-HSD1 of below about 1,000 nM; preferably below about 100 nM; more preferably below about 50 nM; even more preferably below about 5 nM; and most preferably below about 1 nM.

The invention includes a therapeutic method for treating or ameliorating an 11β-HSD1 mediated disorder in a subject in need thereof comprising administering to a subject in need thereof an effective amount of an 11β-HSD1 inhibitor of the invention, or an enantiomer, diastereomer, or pharmaceutically acceptable salt thereof or composition thereof. As used herein, "treating" or "treatment" includes both therapeutic and prophylactic treatment. Therapeutic treatment includes reducing the symptoms associated with a disease or condition and/or increasing the longevity of a subject with the disease or condition. Prophylactic treatment includes delaying the onset of a disease or condition in a subject at risk of developing the disease or condition or reducing the likelihood that a subject will then develop the disease or condition in a subject that is at risk for developing the disease or condition.

An embodiment of the invention includes administering an 11β-HSD1 inhibiting compound of the invention or composition thereof in a combination therapy with one or more additional agents for the treatment of diabetes, dyslipidemia, cardiovascular disease, hypertension, obesity, cancer or glaucoma. Agents for the treatment of diabetes include insulins, such as Humulin® (Eli Lilly), Lantus® (Sanofi Aventis), Novolin (Novo Nordisk), and Exubera® (Pfizer); PPAR gamma agonists, such as Avandia® (rosiglitizone maleate, GSK) and Actos® (pioglitazone hydrochloride, Takeda/Eli Lilly); sulfonylureas, such as Amaryl® (glimepiride, Sanofi Aventis), Diabeta® (glyburide, Sanofi Aventis), Micronase®/Glynase® (glyburide, Pfizer), and Glucotrol®/Glucotrol XL® and (glipizide, Pfizer); meglitinides, such as Prandin®/NovoNorm® (repaglinide, Novo Nordisk), Starlix® (nateglinide, Novartis), and Glufast® (mitiglinide, Takeda); biguanides, such as Glucophase®/Glucophase XR® (metformin HCl, Bristol Myers Squibb) and Glumetza (metformin HCl, Depomed); thiazolidinediones; amylin analogs, GLP-1 analogs; DPP-IV inhibitors; PTB-1B inhibitors; protein kinase inhibitors (including AMP-activated protein kinase inhibitors); glucagon antagonists, glycogen synthase kinase-3 beta inhibitors; glucose-6-phoshatase inhibitors; glycogen phosphorylase inhibitors; sodium glucose co-transporter inhibitors, and alpha-glucosidase inhibitors, such as Precose®/Glucobay®/Prandase®/Glucor® (acarbose, Bayer) and Glyset® (miglitol, Pfizer). Agents for the treatment of dyslipidemia and cardiovascular disease include statins, fibrates, and ezetimbe. Agents for the treatment of hypertension include alpha-blockers, beta-blockers, calcium channel blockers, diuretics, angiotensin converting enzyme (ACE) inhibitors, dual ACE and neutral endopeptidase (NEP) inhibitors, angiotensin-receptor blockers (ARBs), aldosterone synthase inhibitors, aldosterone-receptor antagonists, or endothelin receptor antagonist. Agents for the treatment of obesity include orlistat, phentermine, sibutramine and rimonabant.

An embodiment of the invention includes administering an 11β-HSD1 inhibiting compound of the invention or composition thereof in a combination therapy with one or more other 11β-HSD1 inhibitors, or with combination products, such as Avandamet® (metformin HCl and rosiglitazone maleate, GSK); Avandaryl® (glimepiride and rosiglitazone maleate, GSK); Metaglip® (glipizide and metformin HCl, Bristol Myers Squibb); and Glucovance® (glyburide and metformin HCl, Bristol Myers Squibb).

The compounds of the present invention can be prepared and administered in a wide variety of oral and parenteral dosage forms. Thus, the compounds of the present invention can be administered by injection, that is, intravenously, intramuscularly, intracutaneously, subcutaneously, intraduodenally, or intraperitoneally. Additionally, the compounds of the present invention can be administered intranasally or transdermally. It will be obvious to those skilled in the art that the following dosage forms may comprise as the active ingredient, either compounds or a corresponding pharmaceutically acceptable salt of a compound of the present invention.

For preparing pharmaceutical compositions from the compounds of the present invention, pharmaceutically acceptable carriers can either be solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material. In powders, the carrier is a finely divided solid which is in a mixture with the finely divided active ingredient.

In tablets, the active ingredient is mixed with the carrier having the necessary binding properties in suitable proportions and compacted in the shape and size desired.

The powders and tablets preferably contain from about one to about seventy percent of the active ingredient. Suitable carriers are magnesium carbonate, magnesium stearate, talc, sugar, lactose, pectin, dextrin, starch, gelatin, tragacanth, methylcellulose, sodium caboxymethylcellulose, a low-melting wax, cocoa butter, and the like. Tablets, powders, cachets, lozenges, fast-melt strips, capsules and pills can be used as solid dosage forms containing the active ingredient suitable for oral administration.

For preparing suppositories, a low-melting wax, such as a mixture of fatty acid glycerides or cocoa butter, is first-melted and the active ingredient is dispersed homogeneously therein, as by stirring. The molten homogeneous mixture is then poured into convenient sized molds, allowed to cool, and thereby to solidify.

Liquid form preparations include solutions, suspensions, retention enemas, and emulsions, for example, water or water propylene glycol solutions. For parenteral injection, liquid preparations can be formulated in solution in aqueous polyethylene glycol solution.

Aqueous solutions suitable for oral administration can be prepared by dissolving the active ingredient in water and adding suitable colorants, flavors, stabilizing, and thickening agents as desired. Aqueous suspensions for oral administration can be prepared by dispersing the finely divided active ingredient in water with viscous material, such as natural or synthetic gums, resins, methylcellulose, sodium carboxymethylcellulose, and other well-known suspending agents.

The pharmaceutical composition is preferably in unit dosage form. In such form, the composition is subdivided into unit doses containing appropriate quantities of the active ingredient. The unit dosage form can be a packaged preparation, the package containing discrete quantities of, for example, tablets, powders, and capsules in vials or ampules. Also, the unit dosage form can be a tablet, cachet, capsule, or lozenge itself, or it can be the appropriate amount of any of these in packaged form.

The quantity of active ingredient in a unit dose preparation may be varied or adjusted from about 0.1 mg to about 1000.0 mg, preferably from about 0.1 mg to about 100 mg. The dosages, however, may be varied depending upon the requirements of the patient, the severity of the condition being treated, and the compound being employed. Determination of the proper dosage for a particular situation is within the skill in the art. Also, the pharmaceutical composition may contain, if desired, other compatible therapeutic agents.

In therapeutic treatment or as a method-of-use as an inhibitor of 11β-HSD1 or an inhibitor in the production of cortisol in the cell, the active ingredient is preferably administered orally in a solid dosage form as disclosed above in an amount of about 0.1 mg to about 100 mg per daily dose where the dose is administered once or more than once daily.

All publications, patents and patent applications mentioned in this specification are herein incorporated by reference to the same extent as if each individual publication or patent application were specifically and individually designated as having been incorporated by reference. It is understood that the examples and embodiments described herein are for illustrative purposes only, and it will be appreciated that the invention is susceptible to modification, variation and change without departing from the proper scope or fair meaning of the appended claims.

While this invention has been particularly shown and described with references to example embodiments thereof, it will be understood by those skilled in the art that various changes in form and details may be made therein without departing from the scope of the invention encompassed by the appended claims.

What is claimed is:

1. A compound of Formula (Iu$^1$)

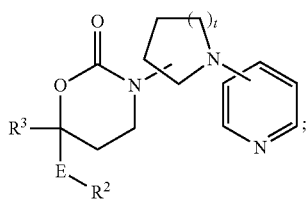

wherein:
t is 1, 2 or 3;
the pyrrolidine, piperidine or azepane ring is optionally substituted with 1 or 2 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclylsulfonyl, ($C_1$-$C_6$)alkylcarbonylamino, ($C_1$-$C_6$)alkyl-carbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy, ($C_1$-$C_6$)alkylcarbonyl, ($C_3$-$C_6$)cycloalkylcarbonyl, ($C_3$-$C_6$)cycloalkylaminocarbonyl, {($C_3$-$C_6$)cycloalkyl}{($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$)cycloalkyl}{($C_1$-$C_6$)alkyl}aminosulfonyl, di($C_3$-$C_6$)cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$)alkyl, ($C_3$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl and di($C_3$-$C_6$)cycloalkylaminocarbonyl($C_1$-$C_6$)alkyl;

the pyridine ring in Formula Iu$^1$ is optionally substituted with 1 to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkylalkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclylsulfonyl, $(C_1-C_6)$alkylcarbonylamino, $(C_1-C_6)$alkylcarbonylamino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, $(C_3-C_6)$cycloalkylcarbonyl, $(C_3-C_6)$cycloalkylaminocarbonyl, $\{(C_3-C_6)\text{cycloalkyl}\}\{(C_1-C_6)\text{alkyl}\}$aminocarbonyl, di$(C_3-C_6)$cycloalkylaminocarbonyl, $(C_3-C_6)$cycloalkylaminosulfonyl, $\{(C_3-C_6)\text{cycloalkyl}\}\{(C_1-C_6)\text{alkyl}\}$aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, $\{(C_3-C_6)\text{cycloalkyl}\}\{(C_1-C_6)\text{alkyl}\}$aminocarbonyl$(C_1-C_6)$alkyl and di$(C_3-C_6)$cycloalkylaminocarbonyl$(C_1-C_6)$alkyl;

E is (a) a bond or (b) $(C_1-C_3)$alkylene or $(C_1-C_2)$alkylenyloxy, wherein the O is attached to $R^2$, each of which is optionally substituted with 1 to 4 groups independently selected from methyl, ethyl, trifluoromethyl or oxo;

$R^2$ is $(C_1-C_6)$alkyl, aryl, heteroaryl, cycloalkyl or heterocyclyl and optionally substituted with up to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$alkenyl, $(C_2-C_6)$alkynyl, $(C_3-C_6)$cycloalkyl$(C_2-C_4)$alkynyl, halo$(C_1-C_6)$alkyl, halo$(C_3-C_6)$cycloalkyl, halo$(C_4-C_7)$cycloalkylalkyl, $(C_1-C_6)$alkoxy, $(C_3-C_6)$cycloalkoxy, $(C_4-C_7)$cycloalkylalkoxy, halo$(C_1-C_6)$alkoxy, halo$(C_3-C_6)$cycloalkoxy, halo$(C_4-C_7)$cycloalkylalkoxy, $(C_1-C_6)$alkylthio, $(C_3-C_6)$cycloalkythio, $(C_4-C_7)$cycloalkylalkylthio, halo$(C_1-C_6)$alkylthio, halo$(C_3-C_6)$cycloalkythio, halo$(C_4-C_7)$cycloalkylalkylthio, $(C_1-C_6)$alkanesulfinyl, $(C_3-C_6)$cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$alkanesulfonyl, $(C_3-C_6)$cycloalkanesulfonyl, $(C_4-C_7)$cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$alkylamino, $(C_1-C_6)$alkoxy$(C_1-C_6)$alkoxy, halo$(C_1-C_6)$alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclylsulfonyl, $(C_1-C_6)$alkylcarbonylamino, $(C_1-C_6)$alkylcarbonyl-amino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy$(C_1-C_6)$alkyl, halo$(C_1-C_6)$alkoxy$(C_1-C_6)$alkyl, hydroxy$(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino$(C_1-C_6)$alkyl amino$(C_2-C_6)$alkoxy, $(C_1-C_6)$alkylamino$(C_2-C_6)$alkoxy, di$(C_1-C_6)$alkylamino$(C_2-C_6)$alkoxy, $(C_1-C_6)$alkylcarbonyl, $(C_3-C_6)$cycloalkylcarbonyl, $(C_3-C_6)$cycloalkylaminocarbonyl, $\{(C_3-C_6)\text{cycloalkyl}\}\{(C_1-C_6)\text{alkyl}\}$aminocarbonyl, di$(C_3-C_6)$cycloalkylaminocarbonyl, $(C_3-C_6)$cycloalkylaminosulfonyl, $\{(C_3-C_6)\text{cycloalkyl}\}\{(C_1-C_6)\text{alkyl}\}$aminosulfonyl, di$(C_3-C_6)$cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$alkyl, $(C_3-C_6)$cycloalkylaminocarbonyl$(C_1-C_6)$alkyl, $\{(C_3-C_6)\text{cycloalkyl}\}\{(C_1-C_6)\text{alkyl}\}$aminocarbonyl$(C_1-C_6)$alkyl and di$(C_3-C_6)$cycloalkylaminocarbonyl$(C_1-C_6)$alkyl;

$R^3$ is selected from $(C_1-C_6)$alkyl, $(C_2-C_6)$alkenyl, $(C_2-C_6)$alkynyl, $(C_3-C_5)$cycloalkyl$(C_1-C_4)$alkyl, $(C_1-C_3)$alkoxy$(C_1-C_3)$alkoxy, or $(C_1-C_3)$alkoxy$(C_1-C_3)$alkyl and is optionally substituted with up to four groups independently selected from fluorine, cyano, oxo, $R^4$, $R^4O-$, $(R^4)_2N-$, $R^4O_2C-$, $R^4C(=O)O-$, $R^4S$, $R^4S(=O)-$, $R^4S(=O)_2-$, $R^4C(=O)NR^4-$, $(R^4)_2NC(=O)-$, $(R^4)_2NC(=O)O-$, $(R^4)_2NC(=O)NR^4-$, $R^4OC(=O)NR^4-$, $(R^4)_2NC(=NCN)NR^4-$, $(R^4O)_2P(=O)O-$, $(R^4O)_2P(=O)NR^4-$, $R^4OS(=O)_2NR^4-$, $(R^4)_2NS(=O)_2O-$, $(R^4)_2NS(=O)_2NR^4-$, $R^4S(=O)_2NR^4-$, $R^4S(=O)_2NHC(=O)-$, $R^4S(=O)_2NHC(=O)O-$, $R^4S(=O)_2NHC(=O)NR^4-$, $R^4OS(=O)_2NHC(=O)-$, $R^4OS(=O)_2NHC(=O)O-$, $R^4OS(=O)_2NHC(=O)NR^4-$, $(R^4)_2NS(=O)_2NHC(=O)-$, $(R^4)_2NS(=O)_2NHC(=O)O-$, $(R^4)_2NS(=O)_2NHC(=O)NR^4-$, $R^4C(=O)NHS(=O)_2-$, $R^4C(=O)NHS(=O)_2O-$, $R^4C(=O)NHS(=O)_2NR^4-$, $R^4OC(=O)NHS(=O)_2-$, $R^4OC(=O)NHS(=O)_2O-$, $R^4OC(=O)NHS(=O)_2NR^4-$, $(R^4)_2NC(=O)NHS(=O)_2-$, $(R^4)_2NC(=O)NHS(=O)_2O-$, $(R^4)_2NC(=O)NHS(=O)_2NR^4-$, spirocycloalkyl; heterocyclyl (optionally substituted with alkyl, haloalkyl, halogen or oxo), heteroaryl (optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo); and $R^4$ is independently selected from H, $(C_1-C_6)$alkyl, halo$(C_1-C_6)$alkyl, amino$(C_1-C_6)$alkyl, $(C_1-C_6)$alkylamino$(C_1-C_6)$alkyl, di$(C_1-C_6)$alkylamino$(C_1-C_6)$alkyl, hydroxy$(C_1-C_6)$alkyl and $(C_1-C_6)$alkoxy$(C_1-C_6)$alkyl;

or a pharmaceutically acceptable salt, enantiomer or diastereomer thereof.

2. The compound of claim 1, wherein the compound is of Formula (Iw¹):

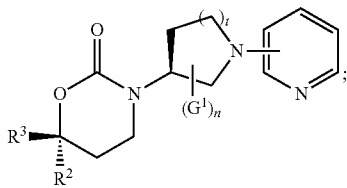

or a pharmaceutically acceptable salt thereof;
wherein:
n is 0, 1 or 2; and
G¹ is oxo, (C₁-C₄)alkyl, (C₁-C₄)alkoxy, (C₁-C₄)haloalkyl, (C₁-C₄)haloalkoxy, halogen, cyano or nitro;
the ring carbon atoms in the pyridine ring in Formula Iw¹ are independently optionally substituted with fluorine, chlorine, cyano, amino, (C₁-C₄)alkyl, (C₃-C₄)cycloalkyl, (C₃-C₄)cycloalkyl(C₁-C₂)alkyl, halo(C₁-C₄)alkyl, (C₁-C₄)alkoxy, (C₁-C₄)haloalkoxy, CONH₂, (C₁-C₄)alkylaminocarbonyl, di(C₁-C₄)alkylaminocarbonyl, (C₃-C₄)cycloalkylaminocarbonyl, {(C₁-C₄)alkyl}{(C₃-C₄)cycloalkyl}aminocarbonyl or (C₁-C₄)alkylcarbonylamino; and
the ring nitrogen in the pyridine ring of Formula Iw¹ is optionally substituted by oxo;
R² is phenyl optionally substituted with 1, 2 or 3 substituents selected from halo, cyano, CONH₂, (C₁-C₄)alkyl, (C₁-C₄)haloalkyl and SO₂Me; and
R³ is MeSO₂NHCH₂CH₂CH₂, H₂NC(=O)CH₂CH₂, H₂NC(=O)CMe₂CH₂, 3-hydroxypropyl, 3-hydroxy-3-methylbutyl, 2-hydroxyethyl, 2-hydroxy-2-methylpropyl or 2-cyano- 2-methylpropyl.

3. The compound of claim 2, wherein t is 2; R² is phenyl or fluorophenyl; R³ is 2-hydroxy-2-methylpropyl or 2-cyano-2-methylpropyl; one or two ring carbon atoms in the pyridine ring of Formula Iw¹ are optionally substituted with fluoro, chloro, cyano, CONH₂, CONHMe, CONMe₂, CONHc-Pr, methyl, ethyl or CF₃; and the ring nitrogen in the pyridine ring in Formula Iw¹ is optionally substituted by oxo.

4. The compound of claim 2, wherein the compound is of Formula (Ix¹)

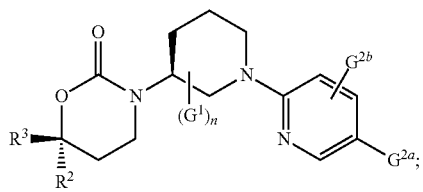

or a pharmaceutically acceptable salt thereof; and
wherein:
G¹ is oxo, (C₁-C₄)alkyl, (C₁-C₄)alkoxy, (C₁-C₄)haloalkyl, (C₁-C₄)haloalkoxy, halogen, cyano or nitro;
G²ᵃ and G²ᵇ are independently selected from hydrogen, fluorine, chlorine, cyano, amino, (C₁-C₄)alkyl, (C₃-C₄)cycloalkyl, (C₃-C₄)cycloalkyl(C₁-C₂)alkyl, halo(C₁-C₄)alkyl, (C₁-C₄)alkoxy, (C₁-C₄)haloalkoxy, CONH₂, (C₁-C₄)alkylaminocarbonyl, di(C₁-C₄)alkylaminocarbonyl, (C₃-C₄)cycloalkylaminocarbonyl, {(C₁-C₄)alkyl}{(C₃-C₄)cycloalkyl}aminocarbonyl and (C₁-C₄)alkylcarbonylamino.

5. The compound of claim 4, wherein R² is phenyl optionally substituted with 1, 2 or 3 substituents selected from halo, cyano, CONH₂, (C₁-C₄)alkyl, (C₁-C₄)haloalkyl and SO₂Me;
and R³ is MeSO₂NHCH₂CH₂CH₂, H₂NC(=O)CH₂CH₂, H₂NC(=O)CMe₂CH₂, 3-hydroxypropyl, 3-hydroxy-3-methylbutyl, 2-hydroxyethyl, 2-hydroxy-2-methylpropyl or 2-cyano-2-methylpropyl.

6. The compound of claim 4, wherein R² is phenyl or fluorophenyl; and R³ is 2-hydroxy-2-methylpropyl or 2-cyano-2-methylpropyl.

7. The compound of claim 4, wherein the compound is represented by one of the following Formulas:

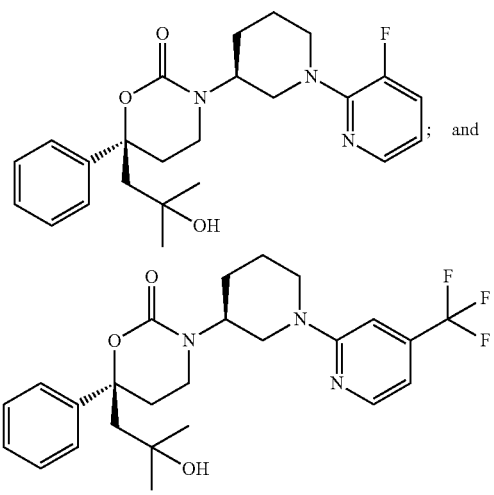

or a pharmaceutically acceptable salt thereof.

8. A compound of Formula (Iu⁸)

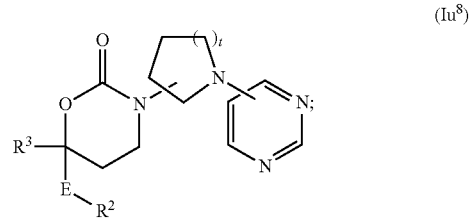

wherein:
t is 1, 2 or 3;
the pyrrolidine, piperidine or azepane ring is optionally substituted with 1 or 2 groups independently selected from fluorine, chlorine, bromine, iodine, cyano, nitro, amino, hydroxy, carboxy, (C₁-C₆)alkyl, hydroxy(C₁-C₆)alkyl, (C₃-C₆)cycloalkyl, hydroxy(C₃-C₆)cycloalkyl, (C₄-C₇)cycloalkylalkyl, (C₂-C₆)alkenyl, halo(C₂-C₆)alkenyl, hydroxy(C₂-C₆)alkenyl, (C₂-C₆)alkynyl, (C₃-C₆)cycloalkyl(C₂-C₄)alkynyl, halo(C₁-C₆)alkyl, halo(C₃-C₆)cycloalkyl, halo(C₄-C₇)cycloalkylalkyl, (C₁-C₆)alkoxy, (C₃-C₆)cycloalkoxy, (C₄-C₇)cycloalkylalkoxy, halo(C₁-C₆)alkoxy, halo(C₃-C₆)cycloalkoxy, halo(C₄-C₇)cycloalkylalkoxy, (C₁-C₆)alkylthio, (C₃-C₆)cycloalkylthio, (C₄-C₇)cycloalkylalkylthio, halo(C₁-C₆)alkylthio, halo(C₃-C₆)

cycloalkythio, halo($C_4$-$C_7$)cycloalkylalkylthio, ($C_1$-$C_6$) alkanesulfinyl, ($C_3$-$C_6$)cycloalkanesulfinyl, ($C_4$-$C_7$) cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$) cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$) alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclylsulfonyl, ($C_1$-$C_6$)alkylcarbonylamino, ($C_1$-$C_6$)alkyl-carbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy ($C_1$-$C_6$)alkyl, halo($C_1$-$C_6$)alkoxy($C_1$-$C_6$)alkyl, hydroxy ($C_1$-$C_6$)alkoxy, heteroaryl oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy, ($C_1$-$C_6$)alkylcarbonyl, ($C_3$-$C_6$)cycloalkylcarbonyl, ($C_3$-$C_6$)cycloalkylaminocarbonyl, {($C_3$-$C_6$)cycloalkyl}{($C_1$-$C_6$)alkyl}aminocarbonyl, di($C_3$-$C_6$) cycloalkylaminocarbonyl, ($C_3$-$C_6$) cycloalkylaminosulfonyl, {($C_3$-$C_6$)cycloalkyl}{($C_1$-$C_6$)alkyl}aminosulfonyl, di($C_3$-$C_6$) cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$) alkyl, ($C_3$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl and di($C_3$-$C_6$)cycloalkylaminocarbonyl($C_1$-$C_6$)alkyl;

the pyrimidine ring in Formula Iu$^8$ is optionally substituted with 1 to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$) cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$) cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo ($C_1$-$C_6$)alkoxy, halo($C_3$-$C_6$)cycloalkoxy, halo($C_4$-$C_7$) cycloalkylalkoxy, ($C_1$-$C_6$)alkylthio, ($C_3$-$C_6$)cycloalkythio, ($C_4$-$C_7$)cycloalkylalkylthio, halo($C_1$-$C_6$) alkylthio, halo($C_3$-$C_6$)cycloalkythio, halo($C_4$-$C_7$) cycloalkylalkylthio, ($C_1$-$C_6$)alkanesulfinyl, ($C_3$-$C_6$) cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$) alkanesulfonyl, ($C_3$-$C_6$)cycloalkanesulfonyl, ($C_4$-$C_7$) cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$) alkylamino, ($C_1$-$C_6$)alkoxy($C_1$-$C_6$)alkoxy, halo($C_1$-$C_6$) alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylamino- sulfonyl, heterocyclylsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy ($C_1$-$C_6$)alkyl, halo($C_1$-$C_6$)alkoxy($C_1$-$C_6$)alkyl, hydroxy ($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino ($C_1$-$C_6$)alkyl amino($C_2$-$C_6$)alkoxy, ($C_1$-$C_6$)alkylamino ($C_2$-$C_6$)alkoxy, di($C_1$-$C_6$)alkylamino($C_2$-$C_6$)alkoxy, ($C_1$-$C_6$)alkylcarbonyl, ($C_3$-$C_6$)cycloalkylcarbonyl, ($C_3$-$C_6$)cycloalkylaminocarbonyl, {($C_3$-$C_6$)cycloalkyl}{ ($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$) cycloalkyl}{($C_1$-$C_6$)alkyl}aminosulfonyl, di($C_3$-$C_6$) cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$) alkyl, ($C_3$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl and di($C_3$-$C_6$)cycloalkylaminocarbonyl($C_1$-$C_6$)alkyl;

E is (a) a bond or (b) ($C_1$-$C_3$)alkylene or ($C_1$-$C_2$)alkylenyloxy, wherein the O is attached to $R^2$, each of which is optionally substituted with 1 to 4 groups independently selected from methyl, ethyl, trifluoromethyl or oxo;

$R^2$ is ($C_1$-$C_6$)alkyl, aryl, heteroaryl, cycloalkyl or heterocyclyl and optionally substituted with up to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$) alkenyl, ($C_2$-$C_6$)alkynyl, ($C_3$-$C_6$)cycloalkyl($C_2$-$C_4$) alkynyl, halo($C_1$-$C_6$)alkyl, halo($C_3$-$C_6$)cycloalkyl, halo ($C_4$-$C_7$)cycloalkylalkyl, ($C_1$-$C_6$)alkoxy, ($C_3$-$C_6$) cycloalkoxy, ($C_4$-$C_7$)cycloalkylalkoxy, halo($C_1$-$C_6$) alkoxy, halo($C_3$-$C_6$)cycloalkoxy, halo($C_4$-$C_7$) cycloalkylalkoxy, ($C_1$-$C_6$)alkylthio, ($C_3$-$C_6$) cycloalkythio, ($C_4$-$C_7$)cycloalkylalkylthio, halo($C_1$-$C_6$) alkylthio, halo($C_3$-$C_6$)cycloalkythio, halo($C_4$-$C_7$) cycloalkylalkylthio, ($C_1$-$C_6$)alkanesulfinyl, ($C_3$-$C_6$) cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$) alkanesulfonyl, ($C_3$-$C_6$)cycloalkanesulfonyl, ($C_4$-$C_7$) cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$) alkylamino, ($C_1$-$C_6$)alkoxy($C_1$-$C_6$)alkoxy, halo($C_1$-$C_6$) alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclylsulfonyl, ($C_1$-$C_6$)alkylcarbonylamino, ($C_1$-$C_6$)alkylcarbonyl-amino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy ($C_1$-$C_6$)alkyl, halo($C_1$-$C_6$)alkoxy($C_1$-$C_6$)alkyl, hydroxy ($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino ($C_1$-$C_6$)alkyl amino($C_2$-$C_6$)alkoxy, ($C_1$-$C_6$)alkylamino ($C_2$-$C_6$)alkoxy, di($C_1$-$C_6$)alkylamino($C_2$-$C_6$)alkoxy, ($C_1$-$C_6$)alkylcarbonyl, ($C_3$-$C_6$)cycloalkylcarbonyl, ($C_3$-$C_6$)cycloalkylaminocarbonyl, {($C_3$-$C_6$)cycloalkyl}{ ($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$) cycloalkyl}{($C_1$-$C_6$)alkyl}aminosulfonyl, di($C_3$-$C_6$) cycloalkylaminosulfonyl, cyano($C_1$-$C_6$)alkyl, aminocarbonyl(C$_1$-C$_6$)alkyl, (C$_1$-C$_6$)alkylaminocarbonyl(C$_1$-C$_6$)alkyl, di(C$_1$-C$_6$)alkylaminocarbonyl(C$_1$-C$_6$)alkyl, (C$_3$-C$_6$)cycloalkylaminocarbonyl(C$_1$-C$_6$)alkyl, {(C$_3$-C$_6$)cycloalkyl}{(C$_1$-C$_6$)alkyl}aminocarbonyl(C$_1$-C$_6$)alkyl and di(C$_3$-C$_6$)cycloalkylaminocarbonyl(C$_1$-C$_6$)alkyl;

R$^3$ is selected from (C$_1$-C$_6$)alkyl, (C$_2$-C$_6$)alkenyl, (C$_2$-C$_6$)alkynyl, (C$_3$-C$_5$)cycloalkyl(C$_1$-C$_4$)alkyl, (C$_1$-C$_3$)alkoxy(C$_1$-C$_3$)alkoxy, or (C$_1$-C$_3$)alkoxy(C$_1$-C$_3$)alkyl and is optionally substituted with up to four groups independently selected from fluorine, cyano, oxo, R$^4$, R$^4$O—, (R$^4$)$_2$N—, R$^4$O$_2$C—, R$^4$C(=O)O—, R$^4$S, R$^4$S(=O)—, R$^4$S(=O)$_2$—, R$^4$C(=O)NR$^4$—, (R$^4$)$_2$NC(=O)—, (R$^4$)$_2$NC(=O)O—, (R$^4$)$_2$NC(=O)NR$^4$—, R$^4$OC(=O)NR$^4$—, (R$^4$)$_2$NC(=NCN)NR$^4$—, (R$^4$O)$_2$P(=O)O—, (R$^4$O)$_2$P(=O)NR$^4$—, R$^4$OS(=O)$_2$NR$^4$—, (R$^4$)$_2$NS(=O)$_2$O—, (R$^4$)$_2$NS(=O)$_2$NR$^4$—, R$^4$S(=O)$_2$NR$^4$—, R$^4$S(=O)$_2$NHC(=O)—, R$^4$S(=O)$_2$NHC(=O)O—, R$^4$S(=O)$_2$NHC(=O)NR$^4$—, R$^4$OS(=O)$_2$NHC(=O)—, R$^4$OS(=O)$_2$NHC(=O)O—, R$^4$OS(=O)$_2$NHC(=O)NR$^4$—, (R$^4$)$_2$NS(=O)$_2$NHC(=O)—, (R$^4$)$_2$NS(=O)$_2$NHC(=O)O—, (R$^4$)$_2$NS(=O)$_2$NHC(=O)NR$^4$—, R$^4$C(=O)NHS(=O)$_2$—, R$^4$C(=O)NHS(=O)$_2$O—, R$^4$C(=O)NHS(=O)$_2$NR$^4$—, R$^4$OC(=O)NHS(=O)$_2$—, R$^4$OC(=O)NHS(=O)$_2$O—, R$^4$OC(=O)NHS(=O)$_2$NR$^4$—, (R$^4$)$_2$NC(=O)NHS(=O)$_2$—, (R$^4$)$_2$NC(=O)NHS(=O)$_2$O—, (R$^4$)$_2$NC(=O)NHS(=O)$_2$NR$^4$—, spirocycloalkyl; heterocyclyl (optionally substituted with alkyl, haloalkyl, halogen or oxo), heteroaryl (optionally substituted with alkyl, haloalkyl, alkoxy, alkylthio, alkylsulfonyl, halogen, trifluoromethyl, dialkylamino, nitro, cyano, CO$_2$H, CONH$_2$, N-monoalkyl-substituted amido, N,N-dialkyl-substituted amido, or oxo), arylamino (optionally substituted with alkyl, alkoxy, alkylthio, alkylsulfonyl, halogen, trifluoromethyl, dialkylamino, nitro, cyano, CO$_2$H, CONH$_2$, N-monoalkyl-substituted amido and N,N-dialkyl-substituted amido) and heteroarylamino (optionally substituted with alkyl, haloalkyl, alkoxy, alkylthio, alkylsulfonyl, halogen, trifluoromethyl, dialkylamino, nitro, cyano, CO$_2$H, CONH$_2$, N-monoalkyl-substituted amido, N,N-dialkyl-substituted amido, or oxo); and R$^4$ is independently selected from H, (C$_1$-C$_6$)alkyl, halo(C$_1$-C$_6$)alkyl, amino(C$_1$-C$_6$)alkyl, (C$_1$-C$_6$)alkylamino(C$_1$-C$_6$)alkyl, di(C$_1$-C$_6$)alkylamino(C$_1$-C$_6$)alkyl, hydroxy(C$_1$-C$_6$)alkyl and (C$_1$-C$_6$)alkoxy(C$_1$-C$_6$)alkyl;

or a pharmaceutically acceptable salt, enantiomer or diastereomer thereof.

9. The compound of claim 8, wherein the compound is of Formula (Iw$^8$):

(Iw$^8$)

or a pharmaceutically acceptable salt thereof;

wherein:

n is 0, 1 or 2;

G$^1$ is oxo, (C$_1$-C$_4$)alkyl, (C$_1$-C$_4$)alkoxy, (C$_1$-C$_4$)haloalkyl, (C$_1$-C$_4$)haloalkoxy, halogen, cyano or nitro;

the ring carbon atoms in the pyrimidine ring in Formula Iw$^8$ are independently optionally substituted with fluorine, chlorine, cyano, amino, (C$_1$-C$_4$)alkyl, (C$_3$-C$_4$)cycloalkyl, (C$_3$-C$_4$)cycloalkyl(C$_1$-C$_2$)alkyl, halo(C$_1$-C$_4$)alkyl, (C$_1$-C$_4$)alkoxy, (C$_1$-C$_4$)haloalkoxy, CONH$_2$, (C$_1$-C$_4$)alkylaminocarbonyl, di(C$_1$-C$_4$)alkylaminocarbonyl, (C$_3$-C$_4$)cycloalkylaminocarbonyl, {(C$_1$-C$_4$)alkyl}{(C$_3$-C$_4$)cycloalkyl}aminocarbonyl or (C$_1$-C$_4$)alkylcarbonylamino;

R$^2$ is phenyl optionally substituted with 1, 2 or 3 substituents selected from halo, cyano, CONH$_2$, (C$_1$-C$_4$)alkyl, (C$_1$-C$_4$)haloalkyl and SO$_2$Me; and R$^3$ is MeSO$_2$NHCH$_2$CH$_2$CH$_2$, H$_2$NC(=O)CH$_2$CH$_2$, H$_2$NC(=O)CMe$_2$CH$_2$, 3-hydroxypropyl, 3-hydroxy-3-methylbutyl, 2-hydroxyethyl, 2-hydroxy-2-methylpropyl or 2-cyano-2-methylpropyl.

10. The compound of claim 9, wherein the compound is represented by one of the following Formulas:

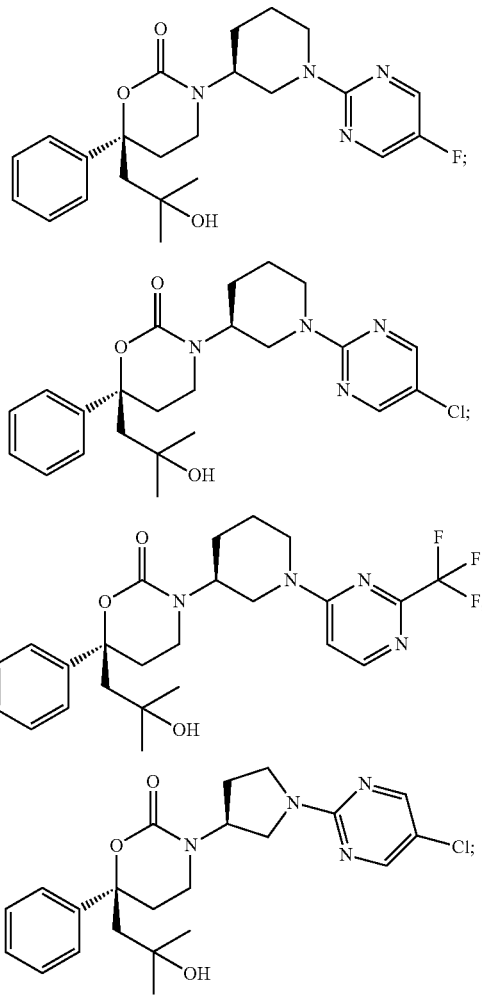

-continued

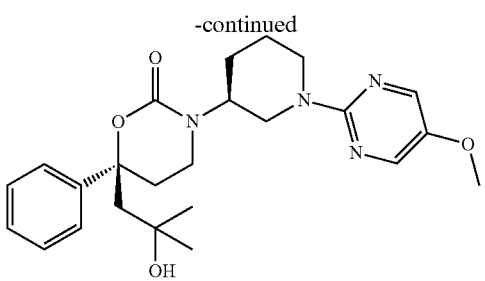

or a pharmaceutically acceptable salt thereof.

11. A compound of Formula (Iu$^{14}$)

(Iu$^{14}$)

wherein:
t is 1, 2 or 3;
the pyrrolidine, piperidine or azepane ring is optionally substituted with 1 or 2 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkylalkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclylsulfonyl, ($C_1$-$C_6$)alkylcarbonylamino, ($C_1$-$C_6$)alkyl-carbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy, ($C_1$-$C_6$)alkylcarbonyl, ($C_3$-$C_6$)cycloalkylcarbonyl, ($C_3$-$C_6$)cycloalkylaminocarbonyl, {($C_3$-$C_6$)cycloalkyl}{($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$)cycloalkyl}{($C_1$-$C_6$)alkyl}aminosulfonyl, di($C_3$-$C_6$)cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$)alkyl, ($C_3$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl and di($C_3$-$C_6$)cycloalkylaminocarbonyl($C_1$-$C_6$)alkyl;

the thiazole ring in Formula Iu$^{14}$ is optionally substituted with 1 to 4 groups independently selected from fluorine, chlorine, bromine, iodine, cyano, nitro, amino, hydroxy, carboxy, ($C_1$-$C_6$)alkyl, hydroxy($C_1$-$C_6$)alkyl, ($C_3$-$C_6$)cycloalkyl, hydroxy($C_3$-$C_6$)cycloalkyl, ($C_4$-$C_7$)cycloalkylalkyl, ($C_2$-$C_6$)alkenyl, halo($C_2$-$C_6$)alkenyl, hydroxy($C_2$-$C_6$)alkenyl, ($C_2$-$C_6$)alkynyl, ($C_3$-$C_6$)cycloalkyl($C_2$-$C_4$)alkynyl, halo($C_1$-$C_6$)alkyl, halo($C_3$-$C_6$)cycloalkyl, halo($C_4$-$C_7$)cycloalkylalkyl, ($C_1$-$C_6$)alkoxy, ($C_3$-$C_6$)cycloalkoxy, ($C_4$-$C_7$)cycloalkylalkoxy, halo($C_1$-$C_6$)alkoxy, halo($C_3$-$C_6$)cycloalkoxy, halo($C_4$-$C_7$)cycloalkylalkoxy, ($C_1$-$C_6$)alkylthio, ($C_3$-$C_6$)cycloalkythio, ($C_4$-$C_7$)cycloalkylalkylthio, halo($C_1$-$C_6$)alkylthio, halo($C_3$-$C_6$)cycloalkythio, halo($C_4$-$C_7$)cycloalkylalkylthio, ($C_1$-$C_6$)alkanesulfinyl, ($C_3$-$C_6$)cycloalkanesulfinyl, ($C_4$-$C_7$)cycloalkylalkanesulfinyl, halo($C_1$-$C_6$)alkanesulfinyl, halo($C_3$-$C_6$)cycloalkanesulfinyl, halo($C_4$-$C_7$)cycloalkylalkanesulfinyl, ($C_1$-$C_6$)alkanesulfonyl, ($C_3$-$C_6$)cycloalkanesulfonyl, ($C_4$-$C_7$)cycloalkylalkanesulfonyl, halo($C_1$-$C_6$)alkanesulfonyl, halo($C_3$-$C_6$)cycloalkanesulfonyl, halo($C_4$-$C_7$)cycloalkylalkanesulfonyl, ($C_1$-$C_6$)alkylamino, di($C_1$-$C_6$)alkylamino, ($C_1$-$C_6$)alkoxy($C_1$-$C_6$)alkoxy, halo($C_1$-$C_6$)alkoxy($C_1$-$C_6$)alkoxy, ($C_1$-$C_6$)alkoxycarbonyl, $H_2NCO$, $H_2NSO_2$, ($C_1$-$C_6$)alkylaminocarbonyl, di($C_1$-$C_6$)alkylaminocarbonyl, ($C_1$-$C_3$)alkoxy($C_1$-$C_3$)alkylaminocarbonyl, heterocyclylcarbonyl, ($C_1$-$C_6$)alkylaminosulfonyl, di($C_1$-$C_6$)alkylaminosulfonyl, heterocyclylsulfonyl, ($C_1$-$C_6$)alkylcarbonylamino, ($C_1$-$C_6$)alkylcarbonylamino($C_1$-$C_6$)alkyl, ($C_1$-$C_6$)alkylsulfonylamino, ($C_1$-$C_6$)alkylsulfonylamino($C_1$-$C_6$)alkyl, ($C_1$-$C_6$)alkoxycarbonyl($C_1$-$C_6$)alkoxy, ($C_1$-$C_6$)alkoxy($C_1$-$C_6$)alkyl, halo($C_1$-$C_6$)alkoxy($C_1$-$C_6$)alkyl, hydroxy($C_1$-$C_6$)alkoxy, heteroaryl, oxo, amino($C_1$-$C_6$)alkyl, ($C_1$-$C_6$)alkylamino($C_1$-$C_6$)alkyl, di($C_1$-$C_6$)alkylamino($C_1$-$C_6$)alkyl amino($C_2$-$C_6$)alkoxy, ($C_1$-$C_6$)alkylamino($C_2$-$C_6$)alkoxy, di($C_1$-$C_6$)alkylamino($C_2$-$C_6$)alkoxy, ($C_1$-$C_6$)alkylcarbonyl, ($C_3$-$C_6$)cycloalkylcarbonyl, ($C_3$-$C_6$)cycloalkylaminocarbonyl, {($C_3$-$C_6$)cycloalkyl}{($C_1$-$C_6$)alkyl}aminocarbonyl, di($C_3$-$C_6$)cycloalkylaminocarbonyl, ($C_3$-$C_6$)cycloalkylaminosulfonyl, {($C_3$-$C_6$)cycloalkyl}{($C_1$-$C_6$)alkyl}aminosulfonyl, di($C_3$-$C_6$)cycloalkylaminosulfonyl, cyano($C_1$-$C_6$)alkyl, aminocarbonyl($C_1$-$C_6$)alkyl, ($C_1$-$C_6$)alkylaminocarbonyl($C_1$-$C_6$)alkyl, di($C_1$-$C_6$)alkylaminocarbonyl($C_1$-$C_6$)alkyl, ($C_3$-$C_6$)cycloalkylaminocarbonyl($C_1$-$C_6$)alkyl, {($C_3$-$C_6$)cycloalkyl}{($C_1$-$C_6$)alkyl}aminocarbonyl($C_1$-$C_6$)alkyl and di($C_3$-$C_6$)cycloalkylaminocarbonyl($C_1$-$C_6$)alkyl;

E is (a) a bond or (b) ($C_1$-$C_3$)alkylene or ($C_1$-$C_2$)alkylenyloxy, wherein the 0 is attached to $R^2$, each of which is optionally substituted with 1 to 4 groups independently selected from methyl, ethyl, trifluoromethyl or oxo;

$R^2$ is ($C_1$-$C_6$)alkyl, aryl, heteroaryl, cycloalkyl or heterocyclyl and optionally substituted with up to 4 groups independently selected from fluorine, chlorine, bromine, iodine, cyano, nitro, amino, hydroxy, carboxy, $(C_1-C_6)$alkyl, hydroxy$(C_1-C_6)$alkyl, $(C_3-C_6)$cycloalkyl, hydroxy$(C_3-C_6)$cycloalkyl, $(C_4-C_7)$cycloalkylalkyl, $(C_2-C_6)$alkenyl, halo$(C_2-C_6)$alkenyl, hydroxy$(C_2-C_6)$ alkenyl, $(C_2-C_6)$alkynyl, $(C_3-C_6)$cycloalkyl$(C_2-C_4)$ alkynyl, halo$(C_1-C_6)$alkyl, halo$(C_3-C_6)$cycloalkyl, halo $(C_4-C_7)$cycloalkylalkyl, $(C_1-C_6)$alkoxy, $(C_3-C_6)$ cycloalkoxy, $(C_4-C_7)$cycloalkylalkoxy, halo$(C_1-C_6)$ alkoxy, halo$(C_3-C_6)$cycloalkoxy, halo$(C_4-C_7)$ cycloalkylalkoxy, $(C_1-C_6)$alkylthio, $(C_3-C_6)$ cycloalkythio, $(C_4-C_7)$cycloalkylalkylthio, halo$(C_1-C_6)$ alkylthio, halo$(C_3-C_6)$cycloalkythio, halo$(C_4-C_7)$ cycloalkylalkylthio, $(C_1-C_6)$alkanesulfinyl, $(C_3-C_6)$ cycloalkanesulfinyl, $(C_4-C_7)$cycloalkylalkanesulfinyl, halo$(C_1-C_6)$alkanesulfinyl, halo$(C_3-C_6)$cycloalkanesulfinyl, halo$(C_4-C_7)$cycloalkylalkanesulfinyl, $(C_1-C_6)$ alkanesulfonyl, $(C_3-C_6)$cycloalkanesulfonyl, $(C_4-C_7)$ cycloalkylalkanesulfonyl, halo$(C_1-C_6)$alkanesulfonyl, halo$(C_3-C_6)$cycloalkanesulfonyl, halo$(C_4-C_7)$cycloalkylalkanesulfonyl, $(C_1-C_6)$alkylamino, di$(C_1-C_6)$ alkylamino, $(C_1-C_6)$alkoxy$(C_1-C_6)$alkoxy, halo$(C_1-C_6)$ alkoxy$(C_1-C_6)$alkoxy, $(C_1-C_6)$alkoxycarbonyl, $H_2NCO$, $H_2NSO_2$, $(C_1-C_6)$alkylaminocarbonyl, di$(C_1-C_6)$alkylaminocarbonyl, $(C_1-C_3)$alkoxy$(C_1-C_3)$alkylaminocarbonyl, heterocyclylcarbonyl, $(C_1-C_6)$alkylaminosulfonyl, di$(C_1-C_6)$alkylaminosulfonyl, heterocyclylsulfonyl, $(C_1-C_6)$alkylcarbonylamino, $(C_1-C_6)$alkylcarbonyl-amino$(C_1-C_6)$alkyl, $(C_1-C_6)$alkylsulfonylamino, $(C_1-C_6)$alkylsulfonylamino$(C_1-C_6)$alkyl, $(C_1-C_6)$alkoxycarbonyl$(C_1-C_6)$alkoxy, $(C_1-C_6)$alkoxy $(C_1-C_6)$alkyl, halo$(C_1-C_6)$alkoxy$(C_1-C_6)$alkyl, hydroxy $(C_1-C_6)$alkoxy, heteroaryl, oxo, amino$(C_1-C_6)$alkyl, $(C_1-C_6)$alkylamino$(C_1-C_6)$alkyl, di$(C_1-C_6)$alkylamino $(C_1-C_6)$alkyl amino$(C_2-C_6)$alkoxy, $(C_1-C_6)$alkylamino $(C_2-C_6)$alkoxy, di$(C_1-C_6)$alkylamino$(C_2-C_6)$alkoxy, $(C_1-C_6)$alkylcarbonyl, $(C_3-C_6)$cycloalkylcarbonyl, $(C_3-C_6)$cycloalkylaminocarbonyl, {$(C_3-C_6)$cycloalkyl}{ $(C_1-C_6)$alkyl}aminocarbonyl, di$(C_3-C_6)$cycloalkylaminocarbonyl, $(C_3-C_6)$cycloalkylaminosulfonyl, {$(C_3-C_6)$ cycloalkyl}{$(C_1-C_6)$alkyl}aminosulfonyl, di$(C_3-C_6)$ cycloalkylaminosulfonyl, cyano$(C_1-C_6)$alkyl, aminocarbonyl$(C_1-C_6)$alkyl, $(C_1-C_6)$alkylaminocarbonyl$(C_1-C_6)$alkyl, di$(C_1-C_6)$alkylaminocarbonyl$(C_1-C_6)$ alkyl, $(C_3-C_6)$cycloalkylaminocarbonyl$(C_1-C_6)$alkyl, {$(C_3-C_6)$cycloalkyl}{$(C_1-C_6)$alkyl}aminocarbonyl$(C_1-C_6)$alkyl and di$(C_3-C_6)$cycloalkylaminocarbonyl$(C_1-C_6)$alkyl;

$R^3$ is selected from $(C_1-C_6)$alkyl, $(C_2-C_6)$alkenyl, $(C_2-C_6)$ alkynyl, $(C_3-C_5)$cycloalkyl$(C_1-C_4)$alkyl, $(C_1-C_3)$alkoxy $(C_1-C_3)$alkoxy, or $(C_1-C_3)$alkoxy$(C_1-C_3)$alkyl and is optionally substituted with up to four groups independently selected from fluorine, cyano, oxo, $R^4$, $R^4O$—, $(R^4)_2N$—, $R^4O_2C$—, $R^4C(=O)O$—, $R^4S$, $R^4S(=O)$—, $R^4S(=O)_2$—, $R^4C(=O)NR^4$—, $(R^4)_2NC(=O)$—, $(R4)_2NC(=O)O$—, $(R^4)_2NC(=O)NR^4$—, $R^4OC(=O)NR^4$—, $(R^4)_2NC(=NCN)NR^4$—, $(R^4O)_2P(=O)$ O—, $(R^4O)_2P(=O)NR^4$—, $R^4OS(=O)_2NR^4$—, $(R^4)_2 NS(=O)_2O$—, $(R^4)_2NS(=O)_2NR^4$—, $R^4S(=O)_2 NR^4$—, $R^4S(=O)_2NHC(=O)$—, $R^4S(=O)_2NHC (=O)O$—, $R^4S(=O)_2NHC(=O)NR^4$—, $R^4OS(=O)_2 NHC(=O)$—, $R^4OS(=O)_2NHC(=O)O$—, $R^4OS (=O)_2NHC(=O)NR^4$—, $(R^4)_2NS(=O)_2NHC (=O)$—, $(R^4)_2NS(=O)_2NHC(=O)O$—, $(R^4)_2NS (=O)_2NHC(=O)NR^4$—, $R^4C(=O)NHS(=O)_2$—, $R^4C(=O)NHS(=O)_2O$—, $R^4C(=O)NHS(=O)_2 NR^4$—, $R^4OC(=O)NHS(=O)_2$—, $R^4OC(=O)NHS (=O)_2O$—, $R^4OC(=O)NHS(=O)_2NR^4$—, $(R^4)_2NC (=O)NHS(=O)_2$—, $(R^4)_2NC(=O)NHS(=O)_2O$—, $(R^4)_2NC(=O)NHS(=O)_2NR^4$—, spirocycloalkyl; heterocyclyl (optionally substituted with alkyl, haloalkyl, halogen or oxo), heteroaryl (optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo), arylamino (optionally substituted with alkyl, alkoxy, alkylthio, alkylsulfonyl, halogen, trifluoromethyl, dialkylamino, nitro, cyano, $CO_2H$, $CONH_2$, N-monoalkyl-substituted amido and N,N-dialkyl-substituted amido) and heteroarylamino (optionally substituted with alkyl, haloalkyl, alkoxy, alkylthio, alkylsulfonyl, halogen, trifluoromethyl, dialkylamino, nitro, cyano, $CO_2H$, $CONH_2$, N-monoalkyl-substituted amido, N,N-dialkyl-substituted amido, or oxo); and $R^4$ is independently selected from H, $(C_1-C_6)$alkyl, halo $(C_1-C_6)$alkyl, amino$(C_1-C_6)$alkyl, $(C_1-C_6)$alkylamino $(C_1-C_6)$alkyl, di$(C_1-C_6)$alkylamino$(C_1-C_6)$alkyl, hydroxy$(C_1-C_6)$alkyl and $(C_1-C_6)$alkoxy$(C_1-C_6)$alkyl;

or a pharmaceutically acceptable salt, enantiomer or diastereomer thereof.

12. The compound of claim 11, wherein the compound is of Formula (Iw14):

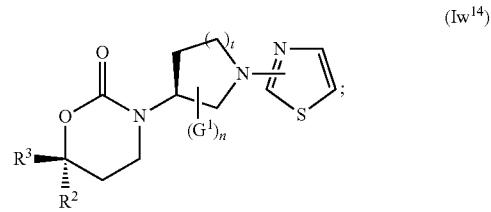

or a pharmaceutically acceptable salt thereof;
wherein:
n is 0, 1 or 2;
$G^1$ is oxo, $(C_1-C_4)$alkyl, $(C_1-C_4)$alkoxy, $(C_1-C_4)$haloalkyl, $(C_1-C_4)$haloalkoxy, halogen, cyano or nitro;
the ring carbon atoms in the thiazole ring in Formula Iw$^{14}$ are independently optionally substituted with fluorine, chlorine, cyano, amino, $(C_1-C_4)$alkyl, $(C_3-C_4)$cycloalkyl, $(C_3-C_4)$cycloalkyl$(C_1-C_2)$alkyl, halo $(C_1-C_4)$alkyl, $(C_1-C_4)$alkoxy, $(C_1-C_4)$haloalkoxy, $CONH_2$, $(C_1-C_4)$alkylaminocarbonyl, di$(C_1-C_4)$ alkylaminocarbonyl, $(C_3-C_4)$cycloalkylaminocarbonyl, {$(C_1-C_4)$alkyl}{$(C_3-C_4)$ cycloalkyl}aminocarbonyl or $(C_1-C_4)$ alkylcarbonylamino;

$R^2$ is phenyl optionally substituted with 1, 2 or 3 substituents selected from halo, cyano, $CONH_2$, $(C_1-C_4)$ alkyl, $(C_1-C_4)$haloalkyl and $SO_2Me$; and $R^3$ is $MeSO_2NHCH_2CH_2CH_2$, $H_2NC(=O)CH_2CH_2$, $H_2NC(=O)CMe_2CH_2$, 3-hydroxypropyl, 3-hydroxy-3-methylbutyl, 2-hydroxyethyl, 2-hydroxy-2-methylpropyl or 2-cyano- 2-methylpropyl.

13. The compound of claim 12, wherein t is 2; $R^2$ is phenyl or fluorophenyl; $R^3$ is 2-hydroxy-2-methylpropyl or 2-cyano-2-methylpropyl; and one or two ring carbon atoms in the thiazole ring of Formula Iw$^{14}$ are optionally substituted with fluoro, chloro, cyano, $CONH_2$, CONHMe, $CONMe_2$, CONHc-Pr, methyl, ethyl or $CF_3$.

14. The compound of claim 12, wherein the compound is of Formula (Ix⁶):

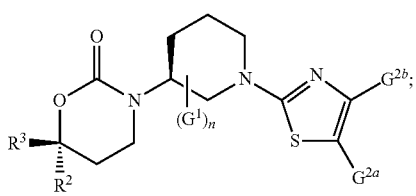
(Ix⁶)

or a pharmaceutically acceptable salt thereof; and
wherein:
$G^1$ is oxo, $(C_1-C_4)$alkyl, $(C_1-C_4)$alkoxy, $(C_1-C_4)$haloalkyl, $(C_1-C_4)$haloalkoxy, halogen, cyano or nitro; and
$G^{2a}$ and $G^{2b}$ are independently selected from hydrogen, fluorine, chlorine, cyano, amino, $(C_1-C_4)$alkyl, $(C_3-C_4)$cycloalkyl, $(C_3-C_4)$cycloalkyl$(C_1-C_2)$alkyl, halo$(C_1-C_4)$alkyl, $(C_1-C_4)$alkoxy, $(C_1-C_4)$haloalkoxy, $CONH_2$, $(C_1-C_4)$alkylaminocarbonyl, di$(C_1-C_4)$alkylaminocarbonyl, $(C_3-C_4)$cycloalkylaminocarbonyl, $\{(C_1-C_4)$alkyl$\}\{(C_3-C_4)$cycloalkyl$\}$aminocarbonyl and $(C_1-C_4)$alkylcarbonylamino.

15. The compound of claim 14, wherein $R^2$ is phenyl optionally substituted with 1, 2 or 3 substituents selected from halo, cyano, $CONH_2$, $(C_1-C_4)$alkyl, $(C_1-C_4)$haloalkyl and $SO_2Me$;
and $R^3$ is $MeSO_2NHCH_2CH_2CH_2$, $H_2NC(\!=\!O)CH_2CH_2$, $H_2NC(\!=\!O)CMe_2CH_2$, 3-hydroxypropyl, 3-hydroxy-3-methylbutyl, 2-hydroxyethyl, 2-hydroxy-2-methylpropyl or 2-cyano-2-methylpropyl.

16. The compound of claim 14, wherein $R^2$ is phenyl or fluorophenyl; and $R^3$ is 2-hydroxy-2-methylpropyl or 2-cyano-2-methylpropyl.

17. The compound of claim 14, wherein the compound is of the following Formula:

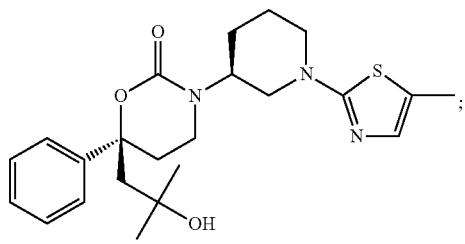

or a pharmaceutically acceptable salt thereof.

18. A method of treating a subject with a disease selected from diabetes mellitus, obesity, metabolic syndrome, glucose intolerance, hyperglycemica, hyperlipidemia, insulin resistance, hypertension caused by cardiovascular disease, dyslipidemia, atherosclerosis, lipodystrophy, osteoporosis, glaucoma, Cushing's syndrome, Addison's Disease, visceral fat obesity associated with glucocorticoid therapy, depression, anxiety, dementia, polycystic ovarian syndrome, and hypergonadism, comprising the step of administering to the subject an effective amount of the compound in claim 1.

19. A pharmaceutical composition comprising: i) a pharmaceutically acceptable carrier or diluent; and ii) the compound in claim 1; or a pharmaceutically acceptable salt, enantiomer or diastereomer thereof.

20. A method of treating a subject with a disease selected from diabetes mellitus, obesity, metabolic syndrome, glucose intolerance, hyperglycemica, hypertension, hyperlipidemia, insulin resistance, hypertension caused by cardiovascular disease, dyslipidemia, atherosclerosis, lipodystrophy, osteoporosis, glaucoma, Cushing's syndrome, Addison's Disease, visceral fat obesity associated with glucocorticoid therapy, depression, anxiety, dementia, cognitive decline, polycystic ovarian syndrome, hypergonadism, pseudo Cushing's Syndrome associated with alcoholic liver disease, tuberculosis, leprosy, psoriasis, to promote wound healing, hypertriglyceridemia, hypercholesterolemia, low HDL levels, high LDL levels, vascular restenosis, pancreatitis, coronary heart disease, peripheral vascular disease, hyperinsulinemia, viral diseases, and Syndrome X, comprising the step of administering to the subject an effective amount of the compound in claim 8.

21. A method of treating a subject with a disease selected from diabetes mellitus, obesity, metabolic syndrome, glucose intolerance, hyperglycemica, hypertension, hyperlipidemia, insulin resistance, hypertension caused by cardiovascular disease, dyslipidemia, atherosclerosis, lipodystrophy, osteoporosis, glaucoma, Cushing's syndrome, Addison's Disease, visceral fat obesity associated with glucocorticoid therapy, depression, anxiety, dementia, cognitive decline, polycystic ovarian syndrome, hypergonadism, pseudo Cushing's Syndrome associated with alcoholic liver disease, tuberculosis, leprosy, psoriasis, to promote wound healing, hypertriglyceridemia, hypercholesterolemia, low HDL levels, high LDL levels, vascular restenosis, pancreatitis, coronary heart disease, peripheral vascular disease, hyperinsulinemia, viral diseases, and Syndrome X, comprising the step of administering to the subject an effective amount of the compound in claim 11.

22. A pharmaceutical composition comprising: i) a pharmaceutically acceptable carrier or diluent; and ii) the compound in claim 8; or a pharmaceutically acceptable salt, enantiomer or diastereomer thereof.

23. A pharmaceutical composition comprising: i) a pharmaceutically acceptable carrier or diluent; and ii) the compound in claim 11; or a pharmaceutically acceptable salt, enantiomer or diastereomer thereof.

24. The method of claim 20, wherein the disease is diabetes mellitus.

* * * * *

UNITED STATES PATENT AND TRADEMARK OFFICE
CERTIFICATE OF CORRECTION

| | |
|---|---|
| PATENT NO. | : 8,242,111 B2 |
| APPLICATION NO. | : 12/990309 |
| DATED | : August 14, 2012 |
| INVENTOR(S) | : David A. Claremon et al. |

It is certified that error appears in the above-identified patent and that said Letters Patent is hereby corrected as shown below:

Column 76, line 51: delete "hyperglycemica" and insert --hyperglycemia--

In the Claims:

Column 93, Claim 18, line 55: delete "hyperglycemica" and insert --hyperglycemia--

Column 94, Claim 20, line 13: delete "hyperglycemica" and insert --hyperglycemia--

Column 94, Claim 21, line 30: delete "hyperglycemica" and insert --hyperglycemia--

Signed and Sealed this
Eighteenth Day of December, 2012

David J. Kappos
*Director of the United States Patent and Trademark Office*